United States Patent
Kato et al.

(10) Patent No.: US 8,664,221 B2
(45) Date of Patent: Mar. 4, 2014

(54) METHOD FOR TREATING AN INFLAMMATORY DISEASE BY ADMINISTERING A 1,2,3,4-TETRAHYDROQUINOXALINE COMPOUND CONTAINING A PHENYL GROUP HAVING A SULFONIC ACID ESTER STRUCTURE INTRODUCED THEREIN AS A SUBSTITUENT

(75) Inventors: Masatomo Kato, Ikoma (JP); Miwa Takai, Ikoma (JP); Takahiro Matsuyama, Ikoma (JP); Tatsuji Kurose, Ikoma (JP); Yumi Hagiwara, Ikoma (JP); Kenji Oki, Ikoma (JP); Mamoru Matsuda, Ikoma (JP); Toshiyuki Mori, Ikoma (JP)

(73) Assignee: Santen Pharmaceutical Co., Ltd., Osaka (JP)

( * ) Notice: Subject to any disclaimer, the term of this patent is extended or adjusted under 35 U.S.C. 154(b) by 203 days.

(21) Appl. No.: 13/063,186

(22) PCT Filed: Sep. 11, 2009

(86) PCT No.: PCT/JP2009/065888
§ 371 (c)(1),
(2), (4) Date: Mar. 9, 2011

(87) PCT Pub. No.: WO2010/029986
PCT Pub. Date: Mar. 18, 2010

(65) Prior Publication Data
US 2011/0166151 A1   Jul. 7, 2011

(30) Foreign Application Priority Data

Sep. 12, 2008   (JP) ................................. 2008-234105

(51) Int. Cl.
| | | |
|---|---|---|
| A01N 43/58 | (2006.01) | |
| A01N 43/60 | (2006.01) | |
| A61K 31/495 | (2006.01) | |
| A61K 31/50 | (2006.01) | |
| C07D 241/36 | (2006.01) | |

(52) U.S. Cl.
USPC ............ 514/249; 544/354; 544/355; 544/116

(58) Field of Classification Search
USPC ............................. 514/249; 544/354, 355, 116
See application file for complete search history.

(56) References Cited

U.S. PATENT DOCUMENTS 6,153,607 A * 11/2000 Pflugfelder et al. .......... 514/178
6,340,758 B1   1/2002 Kornberg et al.
(Continued)

FOREIGN PATENT DOCUMENTS

EP   1 944 290 A1   7/2008
(Continued)

OTHER PUBLICATIONS

Nagelhout et al. (J of Ocular Pharmacology and Therapeutics, 21, 2, 2005, p. 139-148).*
(Continued)

*Primary Examiner* — Sreeni Padmanabhan
*Assistant Examiner* — Uma Ramachandran
(74) *Attorney, Agent, or Firm* — Holtz Holtz Goodman & Chick PC

(57) ABSTRACT

The object aims to find a novel pharmacological activity of a novel 1,2,3,4-tetrahydroquinoxaline derivative which contains, as a substituent, a phenyl group having a sulfonic acid ester structure introduced therein. A compound represented by general formula (1) or a salt thereof is useful as a glucocorticoid receptor agonist, particularly as a therapeutic agent for diseases against which a glucocorticoid receptor agonist (e.g., a steroid) is believed to be effective, such as inflammatory bone/joint diseases, inflammatory ophthalmic diseases (inflammatory ophthalmic diseases in the anterior or posterior segment of an eye). $R^1$ represents a group represented by general formula (2a), (3a), (4a) or (5a); $R^2$ represents a lower alkyl group which may have a substituent, a lower cycloalkyl group which may have a substituent, or the like; $R^3$ represents a lower alkyl group; $R^4$, $R^5$, $R^6$ or $R^7$ represent a halogen atom, a lower alkyl group which may have a substituent, a hydroxy group, a lower alkoxy group which may have a substituent, or the like; and m, n, p or q represents a number of 0, 1 or 2.

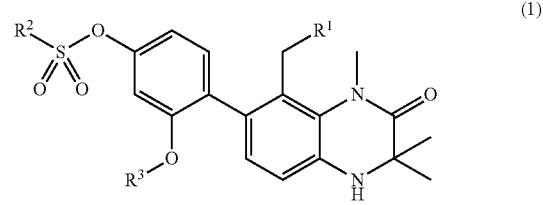

(1)

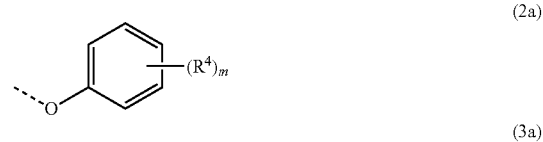

(2a)

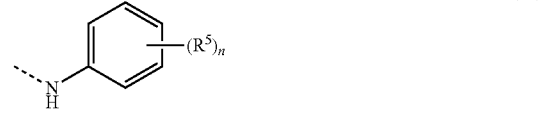

(3a)

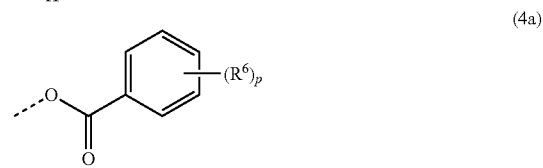

(4a)

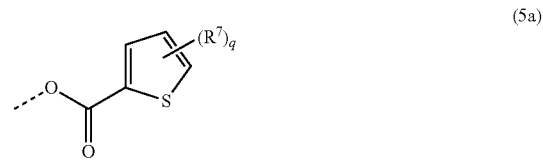

(5a)

8 Claims, No Drawings

(56) References Cited

U.S. PATENT DOCUMENTS

| | | |
|---|---|---|
| 6,369,057 B1 | 4/2002 | Billhardt et al. |
| 6,852,719 B2 | 2/2005 | Liu et al. |
| 2004/0266758 A1 | 12/2004 | Hadida-Ruah et al. |
| 2007/0249611 A1 | 10/2007 | Feng et al. |
| 2009/0111807 A1 | 4/2009 | Matsuda et al. |
| 2009/0298826 A1 | 12/2009 | Matsuda et al. |
| 2009/0298827 A1 | 12/2009 | Matsuda et al. |
| 2009/0326009 A1 | 12/2009 | Matsuda et al. |
| 2010/0056504 A1 | 3/2010 | Matsuda et al. |
| 2010/0137307 A1 | 6/2010 | Matsuda et al. |

FOREIGN PATENT DOCUMENTS

| | | |
|---|---|---|
| EP | 2151436 A1 | 2/2010 |
| JP | 2002-193955 A | 7/2002 |
| JP | 2008-74829 A | 4/2008 |
| WO | WO 2004/099192 A2 | 11/2004 |
| WO | WO 2006/015259 A2 | 2/2006 |
| WO | WO 2007/105766 A1 | 9/2007 |
| WO | WO 2008/111632 A1 | 9/2008 |
| WO | WO 2008/146871 A1 | 12/2008 |
| WO | WO 2009/035067 A1 | 3/2009 |
| WO | WO 2009/035068 A1 | 3/2009 |

OTHER PUBLICATIONS

Heath (Continuing Education and Training: 2007, p. 1-9).*

George Patani et al., "Bioisosterism: A Rational Approach in Drug Design", *Chem. Rev.* 1996, 96, 3147-3176.

Igaku Daijiten, Nanzando (Nanzando'S Medical Dictionary), The 17$^{th}$ Edition, 1038-1040 (Feb. 1, 1996).

Supplementary European Office Action dated Nov. 23, 2011 for EP 09813132.

Jeffrey N. Miner et al, "New and improved glucocorticoid receptor ligands," Expert Opinion on Investigational Drugs, Ashley Publications Ltd., London, GB, vol. 14, No. 12, Dec. 1, 2005, pp. 1527-1545.

V.C. Jordan, "Tamoxifen: A Most Unlikely Pioneering Medicine", *Nature Reviews: Drug Discovery*, 2, 2003, 205.

D.G. Hackam et al, "Translation of Research Evidence from Animals to Humans". *JAMA*, 296(14) 2006, 1731-1732.

McNaught, A.D. et al: "Aryl groups", Compendium of Chemical Terminology, 2$^{nd}$ Edition, [Online] 1997, XP-002582725, IUPAC.

McNaught, A.D. et al: "Arenes", Compendium of Chemical Terminology, 2$^{nd}$ Edition, [Online] 1997, XP-002582726, IUPAC.

Sougou Rinsyou, "New Horizons of Glucocorticoid therapy in 21$^{st}$ Century", 54(7) 1951-2076 (2005).

Igaku Daijiten, Nanzando (Nanzando'S Medical Dictionary), The 17$^{th}$ edition, 1038-1040, 1996.

* cited by examiner

METHOD FOR TREATING AN INFLAMMATORY DISEASE BY ADMINISTERING A 1,2,3,4-TETRAHYDROQUINOXALINE COMPOUND CONTAINING A PHENYL GROUP HAVING A SULFONIC ACID ESTER STRUCTURE INTRODUCED THEREIN AS A SUBSTITUENT

This application is the U.S. national phase application of International Application PCT/JP2009/065888 filed Sep. 11, 2009.

TECHNICAL FIELD

The present invention relates to glucocorticoid receptor agonists comprising 1,2,3,4-tetrahydroquinoxaline derivatives containing a phenyl group having a sulfonic acid ester structure introduced therein as a substituent, which are useful as pharmaceuticals. The glucocorticoid receptor agonists of this invention are useful as therapeutic agents for inflammatory diseases, especially as therapeutic agents for the ocular inflammatory diseases and/or the inflammatory bone-joint disorders.

BACKGROUND ART

A glucocorticoid receptor is a 94 kDa ligand-activated intracellular transcriptional regulatory factor that is a member of the nuclear receptor superfamily. This receptor is known to affect the regulation of the metabolism of carbohydrates, proteins, fats and the like, suppression of the immune or inflammatory responses, activation of the central nervous system, regulation of cardiovascular function, and basal and stress-related homeostasis and the like due to its transcriptional regulatory action (SOUGOU RINSYOU, 54(7), 1951-2076 (2005), JP-A-2002-193955).

Such drugs which bind to a glucocorticoid receptor have an action of glucocorticoid receptor agonist or glucocorticoid receptor antagonist, these actions are entirely different from each other and it is determined which action the drugs show by the slight difference of the chemical structures of them.

As typical glucocorticoid receptor agonists, glucocorticoid receptor agonists synthesized in the living body such as cortisol and corticosterone, synthetic glucocorticoid receptor agonists such as dexamethasone, prednisone and prednisolone are known (JP-A-2002-193955). These glucocorticoid receptor agonists are generally called steroids due to having a steroid structure and are applied to the treatment of various diseases.

However, it is also known there are some cases that these steroids produce the side effects such as steroid peptic ulcer, steroid purpura, steroid pancreatitis, steroid diabetes, steroid cataract, steroid-induced glaucoma by the use of them (IGAKU DAIJITEN, NANZANDO, The 17th edition, 1038-1040), therefore to prevent these side effects, it is hoped to create the drug which does not have a steroid structure.

On the other hand, the compounds having a 1,2,3,4-tetrahydroquinoxaline structure containing a phenyl group having a sulfonic acid ester structure introduced therein as a substituent are not disclosed, and as a matter of fact, the usage, that is, the effect of the glucocorticoid receptor agonist or the like of these compounds is not known at all.

DISCLOSURE OF THE INVENTION

Problems to be Solved

It is a very interesting subject to find a new pharmacological action of novel 1,2,3,4-tetrahydroquinoxaline derivatives containing a phenyl group having a sulfonic acid ester structure introduced therein as a substituent by synthesizing them.

Means of Solving Problems

The present inventors conducted the intensive studies of finding a new pharmacological action of novel 1,2,3,4-tetrahydroquinoxaline derivatives containing a phenyl group having a sulfonic acid ester structure introduced therein as a substituent, and as a result, they found that novel 1,2,3,4-tetraydroquinoxaline derivatives containing a phenyl group having a sulfonic acid ester structure introduced therein as a substituent have an excellent agonist activity to the glucocorticoid receptor and are useful as therapeutic agents for the inflammatory diseases.

In addition, they investigated the effect of the novel 1,2,3,4-tetrahydroquinoxaline derivatives containing a phenyl group having a sulfonic acid ester structure introduced therein on ocular inflammatory disease models (allergic conjunctivitis model in mice, choroidal neovascularization model in rats) and these compounds showed the excellent inhibition effect on these models, and as a result, they found that these compounds are especially useful as therpeutic agents for the ocular inflammatory diseases. Further they investigated the effect of the novel 1,2,3,4-tetrahydroquinoxaline derivatives on an inflammatory bone-joint disorder model (carrageenan paw edema model in rats) and these compounds showed the excellent inhibition effect on this model. As a result, they completed this invention.

Novel 1,2,3,4-tetraydroquinoxaline derivatives containing a phenyl group having a sulfonic acid ester structure introduced therein in this invention mean the compounds represented by the following general formula (1), and the salts thereof (hereinafter referred to as "the present compound"), and the glucocorticoid receptor agonist comprising the present compound and the pharmaceutical composition comprising at least the glucocorticoid receptor agonist as an active ingredient are this invention. Preferably a therapeutic agent for the inflammatory diseases, comprising at least the glucocorticoid receptor agonist as an active ingredient, and more preferably a therapeutic agent for the ocular inflammatory diseases and/or the inflammatory bone-joint disorders, comprising at least the glucocorticoid receptor agonist as an active ingredient are this invention.

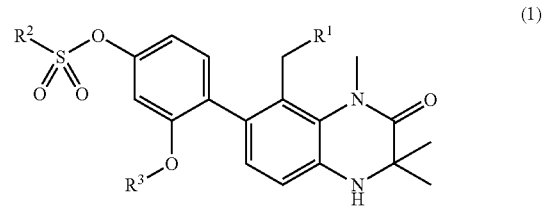

(1)

[$R^1$ represents the following general formula (2a), (3a), (4a) or (5a);

(2a)

(3a)

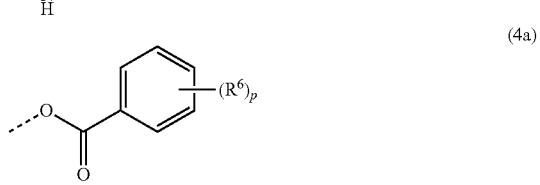

(4a)

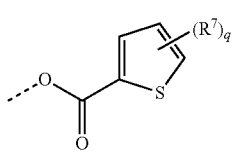
(5a)

R² represents a lower alkyl group which may have a substituent, a lower cycloalkyl group which may have a substituent or an aralkyl group which may have a substituent;

R³ represents a lower alkyl group;

R⁴, R⁵, R⁶ or R⁷ represents a halogen atom, a lower alkyl group which may have a substituent, a hydroxyl group, a lower alkoxy group which may have a substituent, a cyano group or a nitro group;

m, n, p or q represents 0, 1 or 2;

in the case where m, n, p or q is 2, each R⁴, R⁵, R⁶ or R⁷ may be the same or different. Hereinafter the same shall apply.]

Advantage of the Invention

This invention provides the glucocorticoid receptor agonists comprising the present compounds which are useful as pharmaceuticals, the pharmaceutical composition comprising at least one of the glucocorticoid receptor agonists as an active ingredient, the therapeutic agent for inflammatory diseases comprising at least one of the glucocorticoid receptor agonists as an active ingredient, and the therapeutic agent for the ocular inflammatory diseases and/or the inflammatory bone-joint disorders.

In particular, the glucocorticoid receptor agonists in this invention are useful as therapeutic agents for the ocular inflammatory diseases and/or the inflammatory bone-joint disorders, and useful as therapeutic agents for the inflammatory diseases on anterior ocular segment such as keratitis, keratoconjunctivitis, conjunctivitis, blepharitis, dry eye syndrome (dry eye), allergic conjunctivitis, anterior uvetis, inflammation on anterior ocular segment after operation and inflammation by rejection of eye organization transplant; therapeutic agents for the inflammatory diseases on posterior ocular segment such as age-related macular degeneration, diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury (including surgical operation), retinitis, uvetis, scleritis, optic neuritis, and/or therapeutic agents for the inflammatory bone-joint disorders such as rheumatoid arthritis, juvenile rheumatoid arthritis (includes still's disease), osteoarthritis, osteoporosis, spondylarthritis.

MODE FOR CARRYING OUT THE INVENTION

Definitions of terms and phrases (atoms, groups and the like) used in this specification will be described below in detail.

The "halogen atom" refers to a fluorine, chlorine, bromine or iodine atom.

The "lower alkyl group" refers to a straight-chain or branched alkyl group having 1 to 8 carbon atoms, preferably 1 to 6 carbon atoms, more preferably 1 to 4 carbon atoms. Specific examples thereof include methyl, ethyl, n-propyl, n-butyl, n-pentyl, n-hexyl, n-heptyl, n-octyl, isopropyl, isobutyl, sec-butyl, tert-butyl and isopentyl groups and the like.

The "lower cycloalkyl group" refers to a cycloalkyl group having 3 to 8 carbon atoms, preferably 3 to 6 carbon atoms. Specific examples thereof include cyclopropyl, cyclobutyl, cyclopentyl, cyclohexyl, cycloheptyl and cyclooctyl groups.

The "aryl group" refers to a residue formed by removing one hydrogen atom from a monocyclic aromatic hydrocarbon, or a bicyclic or tricyclic condensed polycyclic aromatic hydrocarbon having 6 to 14 carbon atoms. Specific examples thereof include phenyl, naphthyl, anthryl and phenanthryl groups and the like.

The "heterocyclic group" refers to a residue formed by removing one hydrogen atom from a saturated or unsaturated monocyclic heterocyclic ring having one or a plurality of heteroatoms selected from a nitrogen atom, an oxygen atom and a sulfur atom in the ring (preferred, a saturated or unsaturated monocyclic 5-membered or 6-membered heterocyclic ring having 3 to 5 carbon atoms and one or two heteroatoms in the ring), or a bicyclic or tricyclic condensed polycyclic heterocyclic ring (preferred, a bicyclic or tricyclic condensed polycyclic heterocyclic ring having 7 to 13 carbon atoms and one or two heteroatoms in the ring).

Specific examples of the "saturated monocyclic heterocyclic ring" include pyrrolidine, pyrazolidine, imidazolidine, triazolidine, piperidine, hexahydropyridazine, hexahydropyrimidine, piperazine, homopiperidine and homopiperazine rings and the like having at least a nitrogen atom in the ring, tetrahydrofuran and tetrahydropyran rings and the like having at least an oxygen atom in the ring, tetrahydrothiophene and tetrahydrothiopyran rings and the like having at least a sulfur atom in the ring, oxazolidine, isoxazolidine and morpholine rings and the like having at least a nitrogen atom and an oxygen atom in the ring, and thiazolidine, isothiazolidine and thiomorpholine rings and the like having at least a nitrogen atom and a sulfur atom in the ring.

Further, such a saturated monocyclic heterocyclic ring can be condensed with a benzene ring or the like to form a bicyclic or tricyclic condensed polycyclic heterocyclic ring such as a dihydroindole, dihydroindazole, dihydrobenzimidazole, tetrahydroquinoline, tetrahydroisoquinoline, tetrahydrocinnoline, tetrahydrophthalazine, tetrahydroquinazoline, tetrahydroquinoxaline, dihydrobenzofuran, dihydroisobenzofuran, chromane, isochromane, dihydrobenzothiophene, dihydroisobenzothiophene, thiochromane, isothiochromane, dihydrobenzoxazole, dihydrobenzisoxazole, dihydrobenzoxazine, dihydrobenzothiazole, dihydrobenzisothiazole, dihydrobenzothiazine, xanthene, 4a-carbazole or perimidine ring and the like.

Specific examples of the "unsaturated monocyclic heterocyclic ring" include dihydropyrrole, pyrrole, dihydropyrazole, pyrazole, dihydroimidazole, imidazole, dihydrotriazole, triazole, tetrahydropyridine, dihydropyridine, pyridine, tetrahydropyridazine, dihydropyridazine, pyridazine, tetrahydropyrimidine, dihydropyrimidine, pyrimidine, tetrahydropyrazine, dihydropyrazine and pyrazine rings and the like having at least a nitrogen atom in the ring, dihydrofuran, furan, dihydropyran and pyran rings and the like having at least an oxygen atom in the ring, dihydrothiophene, thiophene, dihydrothiopyran and thiopyran rings and the like having at least a sulfur atom in the ring, dihydrooxazole, oxazole, dihydroisoxazole, isoxazole, dihydrooxazine and oxazine rings and the like having at least a nitrogen atom and an oxygen atom in the ring, dihydrothiazole, thiazole, dihydroisothiazole, isothiazole, dihydrothiazine and thiazine rings and the like having at least a nitrogen atom and a sulfur atom in the ring.

Further, such an unsaturated monocyclic heterocyclic ring can be condensed with a benzene ring or the like to form a bicyclic or tricyclic condensed polycyclic heterocyclic ring such as an indole, indazole, benzimidazole, benzotriazole, dihydroquinoline, quinoline, dihydroisoquinoline, isoquinoline, phenanthridine, dihydrocinnoline, cinnoline, dihydrophthalazine, phthalazine, dihydroquinazoline, quinazoline, dihydroquinoxaline, quinoxaline, benzofuran, isobenzofuran, chromene, isochromene, benzothiophene, isobenzothiophene, thiochromene, isothiochromene, benzoxazole, benzisoxazole, benzoxazine, benzothiazole, benzisothiazole, benzothiazine, phenoxanthin, carbazole, β-carboline, phenanthridine, acridine, phenanthroline, phenazine, phenothiazine or phenoxazine ring and the like.

The "aralkyl group" refers to a group formed by replacing one or a plurality of hydrogen atoms of a lower alkyl group with an aryl group. Specific examples thereof include benzyl, phenethyl and naphthylmethyl groups and the like.

The "lower alkoxy group" refers to a group formed by replacing the hydrogen atom of a hydroxy group with a lower alkyl group. Specific examples thereof include methoxy, ethoxy, n-propoxy, n-butoxy, n-pentoxy, n-hexyloxy, n-heptyloxy, n-octyloxy, isopropoxy, isobutoxy, sec-butoxy, tert-butoxy and isopentoxy groups and the like.

The "lower alkyl group which may have a substituent", "lower alkoxy group which may have a substituent", "lower cycloalkyl group which may have a substituent" and "aralkyl group which may have a substituent" refer to a "lower alkyl group", a "lower alkoxy group", a "lower cycloalkyl group" and an "aralkyl group" which may have one or a plurality of substituents selected from the following $\alpha^1$ group, respectively.

[$\alpha^1$ Group]

A halogen atom, a lower alkyl group, a lower cycloalkyl group, an aryl group, a heterocyclic group, a hydroxy group, a lower alkoxy group and —NR$^s$R$^t$.

R$^s$ and R$^t$ are the same or different and represent a hydrogen atom, a lower alkyl group, a lower alkyl group substituted with —NR$^u$R$^v$ (R$^u$ and R$^v$ are the same or different and represent a hydrogen atom or a lower alkyl group), a lower cycloalkyl group, an aryl group, a heterocyclic group or an aralkyl group.

The term "a plurality of substituents" in this invention refers to substituents which are 2 or more than 2 and less than or equal to the maximum substitutable number, and each substituent may be the same or different, and the number of the substituents is preferably 2. Further, a hydrogen atom and a halogen atom are also included in the concept of the "substituent".

The "glucocorticoid receptor agonist" in this invention refers to an agonist that exhibits a full agonistic action or a partial agonistic action by binding to the glucocorticoid receptor.

The "therapeutic agent" in this invention means the medicines for the prevention and/or the treatment of diseases.

As a medical usage of the "glucocorticoid receptor agonist" in this invention, there is especially no limitation as long as the disease is the one which the glucocorticoid receptor agonist is effective as a therapeutic agent, and generally it is possible to apply to all of the disease that can be treated by the steroids.

For example, endocrine diseases such as chronic adrenocortical dysfunction (primary, secondary, pituitary, iatrogenic), acute adrenocortical dysfunction (adrenal crisis), adrenogenital syndrome, subacute thyroiditis, thyrotoxicosis syndrome [thyroid (poisoning) crisis], malignant exophthalmus due to thyroid disease, isolated ACTH deficiency, idiopathic hypoglycemia; collagenosis such as lupus erythematosus (systemic and chronic discoid), systemic angitis (including aortitis syndrome, periarteritis nodosa, polyarteritis, Wegener's granulomatosis), multiple myositis (dermatomyositis), scleroderma; kidney diseases such as nephrosis, nephrotic syndrome; heart diseases such as congestive heart failure; Allergic diseases such as bronchial asthma, asthmatic bronchitis (including infantile asthmatic bronchitis), allergy and poisoning caused by medicine or other chemical substances (including drug rash, toxicoderma), serum sickness; blood diseases such as purpura (thrombocytopenic and non-thrombocytopenic), aplastic anemia, leukemia (including acute leukemiam, acute inversion of chronic myeloid leukemia, chronic lymphatic leukemia, leukemia cutis), hemolytic anemia, granulocytopenia; digestive apparatus diseases such as ulcerative colitis, regional enteritis, the improvement of physical status of serious illness hectic diseases (the cancer end and sprue); liver diseases such as fulminant hepatitis, bile stagnation type acute hepatitis, chronic hepatitis, cirrhosis; pulmonary diseases such as sarcoidosis, diffuse interstitial pneumonia (the pulmonary fibrosis, the radiation pneumonitis); serious infection; tuberculous diseases such as pulmonary tuberculosis, tuberculous meningitis, tuberculous pleurisy, tuberculous peritonitis, tuberculous pericarditis; neural diseases such as encephalomyelitis (including encephalitis, myelitis), peripheral neuritis (including Guillain-Barré syndrome), mytonia, myasthenia gravis, multiple sclerosis (including neuromyelitis optica), chorea minor, paralysis of facial nerve, arachonoid of spinal cord retinitis; malignant tumors such as malignant lymphoma (lymphosarcomatosis, reticulosarcomatosis, Hodgkin's disease, cutaneous reticulosis, mycosis fungoides) and similar diseases (closely related diseases), acidophilic granuloma, relapse metastasis of breast cancer; digestive symptom (nausea, vomitus) by administering of an anti-malignant tumor agent (such as cisplatin); surgical diseases such as resection of adrenal grant, surgical invasion to the patient of adrenocortical hypofunction, lung edema after invading, transplant of organ/tissue, ophidiasis/insect venom (including serious sting), unidentified fervescence; obstetrics and gynecology diseases such as adhesion prevention after oviduct orthopedic surgery; urology diseases such as prostatic cancer, priapism; dermatology diseases such as eczema/deramatitis (acute eczema, subacute eczema, chronic eczema, contact dermatitis, mummular eczema, autosensitized dermatitis, atopic dermatitis, eczema infantum, lichen simplex chronicus Vidal, other neurodermatitis, seborrheic dermatitis, keratoderma, keratodermia tylodes Palmaris progressive, other hand/finger dermatitis, genitial/anal eczema, pinna and external auditory meatus eczema/deramatitis, eczema, ermatitis and so on around nasal vestibule and nasal ala), prurigo (including infantile strophulus, lichen urticatus, Urticaria persistens), urticaria, psoriasis and parapsoriasis (psoriasis vulgaris (severe case), psoriasis arthropathica, psoriatic erythroderma, pustular psoriasis, acrodermatitis, impetigo herpetiformis, Reiter's syndrome), pustulosis palmoplantaris, lichen planus, benigns, erythema (erythema exsudativum multiforme, erythema nodosum), anaphylactoid purpura (allergic, Schonlein, Henoch), Weber-Christian disease, oculomncocutaneous syndrome (ectdermosis erosiva pluriorificialis, Stevens-Johnson syndrome, dermatostomatitis, Fuck's syndrome, Behcet's dosease, Lipschutz' acute vulvae ulcer), Raynaud disease, alopecia areata, pemphigus (pemphigus vulgaris, pemphigus foliaceus, Senear-Usher syndrome, pemphigus vegetans), Duhring's dermatitis herpetiformis (including pemphigoid, prurigo gestationis), epidermolysis bullosa hereditaria, herpes zoster, erythroderma (including pityriasis rubra hebra), lupus miliaris disseminatus faciei, allergic angitis and the related diseases (including pityriasis lichenoides et varioliformis acute), ulcerative chronic pyoderma, sclerema neonatorum and the like; otorhinolaryngology diseases such as acute/chronic tympanitis, exudative tympanitis, tubal stenosis, Meniere's disease and Meniere's syndrome, acute sensorineural deafness, vasomotor rhinitis, allergic rhinitis, pollinosis (hay fever), progressives malignes Granulom, pharyngitis, laryngeal edema, follow-up treatment after otorhinolarygological surgical operation, dysosmia, acute/chronic (replicate) sialadenitis; oral surgery diseases such as inveterate stomatitis, glossitis; rheumatic diseases such as rheumatic fever (including rheumatic carditis), polymyalgia rheumatica, ankylosing spondylitis (rheumatoid spondylitis); and the following inflammatory diseases, are enumerated.

The "inflammatory disease" in this invention is not particularly limited as long as it is a disease with an inflammation.

For example, diseases such as the inflammatory bone-joint disorder, the ocular inflammatory disease, asthma, bronchitis, rhinitis, dermatitis, the inflammatory bowel disease and the like, preferably the inflammatory bone-joint disorder and the ocular inflammatory disease are enumerated.

The "inflammatory bone-joint disorder" in this invention is not particularly limited as long as it is a disease with an inflammation on the joint part, for example, rheumatoid arthritis, juvenile rheumatoid arthritis (includes still's disease), osteoarthritis, osteoporosis, spondylarthritis and the like, preferably rheumatoid arthritis and/or osteoarthritis are enumerated.

The "ocular inflammatory disease" in this invention is not particularly limited as long as it is a disease with an inflammation on eye part, for example, as for inflammatory diseases of anterior segment of eyeball, keratitis, keratoconjunctivitis, conjunctivitis, blepharitis, dry eye syndrome, allergic conjunctivitis, anterior uveitis, inflammation on anterior segment of eyeball after operation, inflammation by rejection of eye organization transplant and the like, preferably dry eye syndrome (dry eye) and allergic conjunctivitis are enumerated.

As for inflammatory diseases of posterior segment of eyeball, age-related macular degeneration, diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, retinitis, uvetis, scleritis, optic neuritis and the like, preferably age-related macular degeneration, diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury, retinitis and the like, more preferably age-related macular degeneration, diabetic retinopathy and diabetic macular edema are enumerated.

The "salt" of the present compound is not particularly limited as long as it is a pharmaceutically acceptable salt. Examples thereof include salts with an inorganic acid such as hydrochloric acid, hydrobromic acid, hydroiodic acid, nitric acid, sulfuric acid, phosphoric acid or the like; salts with an organic acid such as acetic acid, fumalic acid, maleic acid, succinic acid, citric acid, tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid or the like; quaternary ammonium salts with methyl bromide, methyl iodide or the like; salts with a halogen ion such as a bromine ion, a chlorine ion, an iodine ion or the like; salts with an alkali metal such as lithium, sodium, potassium or the like; salts with an alkaline earth metal such as calcium, magnesium or the like; salts with a metal such as iron, zinc or the like; salts with ammonia; salts with an organic amine such as triethylenediamine, 2-aminoethanol, 2,2-iminobis(ethanol), 1-deoxy-1-(methylamino)-2-D-sorbitol, 2-amino-2-(hydroxymethyl)-1,3-propanediol, procaine, N,N-bis (phenylmethyl)-1,2-ethanediamine or the like.

In the case where there are geometrical isomers and/or optical isomers in the present compound, these isomers are also included in the scope of the present invention.

In the case where there are proton tautomers in the present compound, these tautomers (keto-form, enol-form) are also included in the scope of the present invention.

In the case where there are hydrates and/or solvates in the present compound, these hydrates and/or solvates are also included in the scope of the present invention.

In the case where there are crystalline polymorphism and/or crystalline polymorphism group (crystalline polymorphism system) in the present compound, these crystalline polymorphism and crystalline polymorphism group (crystalline polymorphism system) are also included in the scope of the present invention. "Crystalline polymorphism group (crystalline polymorphism system)" herein means each crystal form in each step where the crystal form changes depending on conditions and/or states (the states also include a state of drug formulation) of manufacture, crystallization and preservation and the like, and the entire process.

(A) Examples of the present compound in this invention include compounds in which the respective groups are groups as defined below, and salts thereof, in the compounds represented by the general formula (1) and salts thereof.

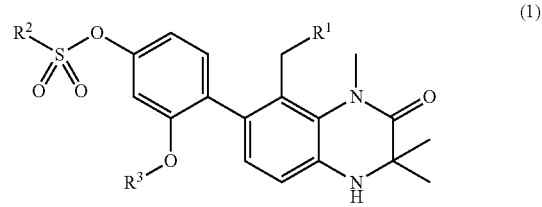

(A1) $R^1$ represents the following general formula (2a), (3a), (4a) or (5a); and/or

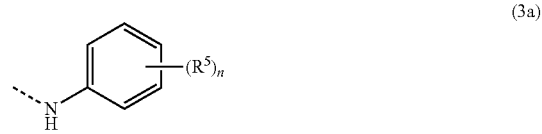

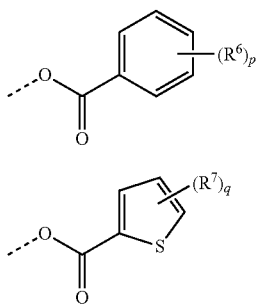
(4a)

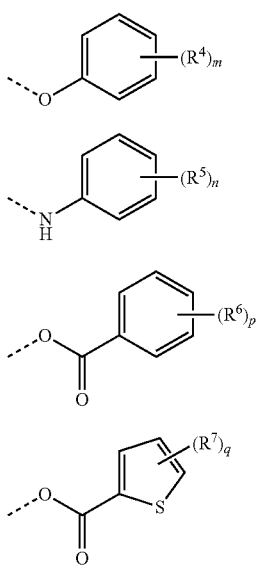
(5a)

(A2) $R^2$ represents a lower alkyl group which may have a substituent, a lower cycloalkyl group which may have a substituent or an aralkyl group which may have a substituent; and/or (A3) $R^3$ represents a lower alkyl group; and/or (A4) $R^4$, $R^5$, $R^6$ or $R^7$ represents a halogen atom, a lower alkyl group which may have a substituent, a hydroxyl group, a lower alkoxy group which may have a substituent, a cyano group or a nitro group; and/or (A5) m, n, p or q represents 0, 1 or 2;

in the case where m, n, p or q is 2, each $R^4$, $R^5$, $R^6$ or $R^7$ may be the same or different.

That is, in the compounds represented by the general formula (1) and salts thereof, examples include compounds that comprise a combination selected from the above (A1), (A2), (A3), (A4) and (A5), and salts thereof.

(B) Preferred examples of the present compound include compounds in which the respective groups are groups as defined below, and salts thereof, in the compounds represented by the general formula (1) and salts thereof.

(B1) $R^1$ represents the following general formula (2a), (3a), (4a) or (5a); and/or (2a)

(3a)

(4a)

(5a)

(B2) $R^2$ represents a lower alkyl group which may have a substituent, a lower cycloalkyl group which may have a substituent or an aralkyl group which may have a substituent; and/or (B3) $R^3$ represents a lower alkyl group; and/or (B4) $R^4$ represents a halogen atom, a lower alkyl group, a hydroxyl group, a lower alkoxy or a nitro group; and/or (B5) $R^5$ represents a halogen atom, a lower alkyl group, a hydroxyl group or a lower alkoxy group; and/or (B6) $R^6$ represents a lower alkyl group, a hydroxyl group or a lower alkoxy group; and/or (B7) $R^7$ represents a halogen atom or a lower alkyl group; and/or (B8) m, n or p represents 1 or 2;

in the case where m, n or p is 2, each $R^4$, $R^5$ or $R^6$ may be the same or different; and/or (B9) q represents 0 or 1.

That is, in the compounds represented by the general formula (1) and salts thereof, examples include compounds that comprise one or a combination of two or more selected from the above (B1), (B2), (B3), (B4), (B5), (B6), (B7), (B8) and (B9), and salts thereof.

Further, the compounds which satisfy the combination of these conditions (B) and the above conditions (A), and the salts thereof are also included in the scope of the present invention.

(C) More preferred examples of the present compound include compounds in which the respective groups are groups as defined below, and salts thereof, in the compounds represented by the general formula (1) and salts thereof.

(C1) $R^1$ represents the following general formula (2b-1), (2b-2), (2b-3), (3b-1), (3b-2), (4b-1) or (5b-1); and/or

(2b-1)

(2b-2)

(2b-3)

(3b-1)

(3b-2)

-continued

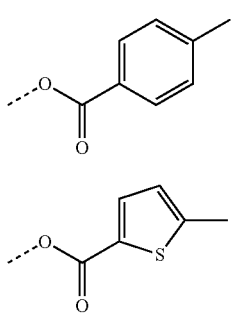

(4b-1)

(5b-1)

(C2) R² represents a lower alkyl group which may have a substituent, a lower cycloalkyl group which may have a substituent or an aralkyl group which may have a substituent; and/or (C3) R³ represents a methyl group.

That is, in the compounds represented by the general formula (1) and salts thereof, examples include compounds that comprise one or a combination of two or more selected from the above (C1), (C2) and (C3), and salts thereof.

Further, the compounds which satisfy the combination of these conditions (C) and the above conditions (A) and/or (B), and the salts thereof are also included in the scope of the present invention.

(D) Preferred specific examples of the present compound include the following compounds and salts thereof.

8-(5-Fluoro-2-methylphenoxymethyl)-7-(2-methoxy-4-methylsulfonyloxyphenyl)-1,3,3-trimethyl-3,4-dihydro-1H-quinoxalin-2-one, 8-(5-Fluoro-2-methylphenoxymethyl)-7-(2-methoxy-4-propylsulfonyloxyphenyl)-1,3,3-trimethyl-3,4-dihydro-1H-quinoxalin-2-one, 7-(2-Methoxy-4-methylsulfonyloxyphenyl)-8-(5-methylthiophen-2-ylcarbonyloxymethyl)-1,3,3-trimethyl-3,4-dihydro-1H-quinoxalin-2-one, 7-(4-Benzylsulfonyloxy-2-methoxyphenyl)-8-(5-fluoro-2-methylphenoxymethyl)-1,3,3-trimethyl-3,4-dihydro-1H-quinoxalin-2-one, 7-(4-Butylsulfonyloxy-2-methoxyphenyl)-8-(5-fluoro-2-methylphenoxymethyl)-1,3,3-trimethyl-3,4-dihydro-1H-quinoxalin-2-one, 7-(4-Ethylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-(4-isopropylsulfonyloxy-2-methoxyphenyl)-1,3,3-trimethyl-3,4-dihydro-1H-quinoxalin-2-one, 7-[4-(3-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(4-methylbenzylsulfonyloxy)phenyl]-1,3,3-trimethyl-3,4-dihydro-1H-quinoxalin-2-one, 7-[4-(4-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-(4-isobutylsulfonyloxy-2-methoxyphenyl)-1,3,3-trimethyl-3,4-dihydro-1H-quinoxalin-2-one, 8-(5-Fluoro-2-methylphenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-fluoro-2-methylphenoxymethyl)-1,3,3-trimethyl-3,4-dihydro-1H-quinoxalin-2-one, 7-[4-(2-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(2-methylbenzylsulfonyloxy)phenyl]-1,3,3-trimethyl-3,4-dihydro-1H-quinoxalin-2-one, 7-(4-Cyclopentylsulfonyloxy-2-methoxyphenyl)-8-(5-fluoro-2-methylphenoxymethyl)-1,3,3-trimethyl-3,4-dihydro-1H-quinoxalin-2-one, 7-(4-Cyclohexylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(3-methylbenzylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-[2-Methoxy-4-(3,3,3-trifluoropropylsulfonyloxy)phenyl]-8-(5-methylthiophen-2-ylcarbonyloxymethyl)-1,3,3-trimethyl-3,4-dihydro-1H-quinoxalin-2-one, 7-(4-Isobutylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-propylsulfonyloxyphenyl)-8-(5-methylthiophen-2-ylcarbonyloxymethyl)-1,3,3-trimethyl-3,4-dihydro-1H-quinoxalin-2-one, 7-(4-Isopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(4-Cyclopentylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-methylsulfonyloxyphenyl)-8-(2-methoxy-5-nitrophenoxymethyl)-1,3,3-trimethyl-3,4-dihydro-1H-quinoxalin-2-one, 8-(2-Methoxy-5-nitrophenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Isobutylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopentylsulfonyloxy-2-methoxyphenyl)-8-(2-methoxy-5-nitrophenoxymethyl)-1,3,3-trimethyl-3,4-dihydro-1H-quinoxalin-2-one, 7-(4-Isopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopropylsulfonyloxy-2-methoxyphenyl)-8-(2-methoxy-5-nitrophenoxymethyl)-1,3,3-trimethyl-3,4-dihydro-1H-quinoxalin-2-one, 8-(2-Methoxy-5-nitrophenoxymethyl)-7-(2-methoxy-4-propylsulfonyloxyphenyl)-1,3,3-trimethyl-3,4-dihydro-1H-quinoxalin-2-one, 7-(4-Cyclopropylsulfonyloxy-2-methoxyphenyl)-8-(2-methyl-5-nitrophenoxymethyl)-1,3,3-trimethyl-3,4-dihydro-1H-quinoxalin-2-one, 7-[2-Methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one, 7-(4-Isobutylsulfonyloxy-2-methoxyphenyl)-8-(2-methyl-5-nitrophenoxymethyl)-1,3,3-trimethyl-3,4-dihydro-1H-quinoxalin-2-one, 7-(4-Isopropylsulfonyloxy-2-methoxyphenyl)-8-(2-methyl-5-nitrophenoxymethyl)-1,3,3-trimethyl-3,4-dihydro-1H-quinoxalin-2-one,
7-(2-Methoxy-4-methylsulfonyloxyphenyl)-8-(2-methyl-5-nitrophenoxymethyl)-1,3,3-trimethyl-3,4-dihydro-1H-quinoxalin-2-one,
7-(4-Cyclopentylsulfonyloxy-2-methoxyphenyl)-8-(2-methyl-5-nitrophenoxymethyl)-1,3,3-trimethyl-3,4-dihydro-1H-quinoxalin-2-one,
7-(2-Methoxy-4-propylsulfonyloxyphenyl)-8-(2-methyl-5-nitrophenoxymethyl)-1,3,3-trimethyl-3,4-dihydro-1H-quinoxalin-2-one,
7-(2-Methoxy-4-propylsulfonyloxyphenyl)-8-(4-methylbenzoyloxymethyl)-1,3,3-trimethyl-3,4-dihydro-1H-quinoxalin-2-one,
7-[4-(3-Chloropropylsulfonyloxy)-2-methoxyphenyl]-8-(5-fluoro-2-methylphenoxymethyl)-1,3,3-trimethyl-3,4-dihydro-1H-quinoxalin-2-one,
7-(4-Chloromethylsulfonyloxy-2-methoxyphenyl)-8-(5-fluoro-2-methylphenoxymethyl)-1,3,3-trimethyl-3,4-dihydro-1H-quinoxalin-2-one,
7-(4-Cyclopropylsulfonyloxy-2-methoxyphenyl)-8-(5-fluoro-2-methylphenylaminomethyl)-1,3,3-trimethyl-3,4-dihydro-1H-quinoxalin-2-one,
7-(4-Cyclopentylsulfonyloxy-2-methoxyphenyl)-8-(5-fluoro-2-methylphenylaminomethyl)-1,3,3-trimethyl-3,4-dihydro-1H-quinoxalin-2-one,
8-(5-Fluoro-2-methylphenylaminomethyl)-7-(2-methoxy-4-propylsulfonyloxyphenyl)-1,3,3-trimethyl-3,4-dihydro-1H-quinoxalin-2-one,
7-(2-Methoxy-4-methylsulfonyloxyphenyl)-8-(2-methoxyphenylaminomethyl)-1,3,3-trimethyl-3,4-dihydro-1H-quinoxalin-2-one,
7-(4-Cyclopropylsulfonyloxy-2-methoxyphenyl)-8-(2-methoxyphenylaminomethyl)-1,3,3-trimethyl-3,4-dihydro-1H-quinoxalin-2-one,
8-(2-Methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one,
7-(4-Isobutylsulfonyloxy-2-methoxyphenyl)-8-(2-methoxyphenylaminomethyl)-1,3,3-trimethyl-3,4-dihydro-1H-quinoxalin-2-one,
7-(4-Isopropylsulfonyloxy-2-methoxyphenyl)-8-(2-methoxyphenylaminomethyl)-1,3,3-trimethyl-3,4-dihydro-1H-quinoxalin-2-one,
7-(4-Cyclopentylsulfonyloxy-2-methoxyphenyl)-8-(2-methoxyphenylaminomethyl)-1,3,3-trimethyl-3,4-dihydro-1H-quinoxalin-2-one,
8-(2-Methoxyphenylaminomethyl)-7-(2-methoxy-4-propylsulfonyloxyphenyl)-1,3,3-trimethyl-3,4-dihydro-1H-quinoxalin-2-one,
7-[4-(3-Benzylaminopropylsulfonyloxy)-2-methoxyphenyl]-8-(5-fluoro-2-methylphenoxymethyl)-1,3,3-trimethyl-3,4-dihydro-1H-quinoxalin-2-one,
8-(5-Fluoro-2-methylphenoxymethyl)-7-[2-methoxy-4-(3-propylaminopropylsulfonyloxy)phenyl]-1,3,3-trimethyl-3,4-dihydro-1H-quinoxalin-2-one,
8-(5-Fluoro-2-methylphenoxymethyl)-7-[2-methoxy-4-[3-(morpholin-4-yl)propylsulfonyloxy]phenyl]-1,3,3-trimethyl-3,4-dihydro-1H-quinoxalin-2-one,
8-(5-Fluoro-2-methylphenoxymethyl)-7-[2-methoxy-4-[3-(piperidin-1-yl)propylsulfonyloxyphenyl]-1,3,3-trimethyl-3,4-dihydro-1H-quinoxalin-2-one,
8-(5-Fluoro-2-methylphenoxymethyl)-7-[2-methoxy-4-[3-[N-(2-methylaminoethyl)-N-methylamino]propylsulfonyloxy]phenyl]-1,3,3-trimethyl-3,4-dihydro-1H-quinoxalin-2-one.

The present compound can be synthesized according to the following procedures. The individual concrete preparation procedures are explained in detail in the section of "Production Examples" in Examples. These examples are intended to make the present invention more clearly understandable, and do not limit the scope of the present invention. In the following synthetic routes, the hal represents a halogen atom, the Fmoc represents a 9-fluorenylmethoxycarbonyl group and PG represents a protecting group which is commonly used.

The present compound (I) can be synthesized according to the synthetic route 1. That is, the compound (I) can be given by the reaction of the compound (II) with a corresponding halide (III) in an organic solvent such as N,N-dimethylformamide (hereinafter referred to as "DMF"), tetrahydrofuran (hereinafter referred to as "THF"), 1,4-dioxane or methylene dichloride in the presence of a base such as triethylamine or potassium carbonate at 0° C. to 50° C. for 1 hour to 24 hours.

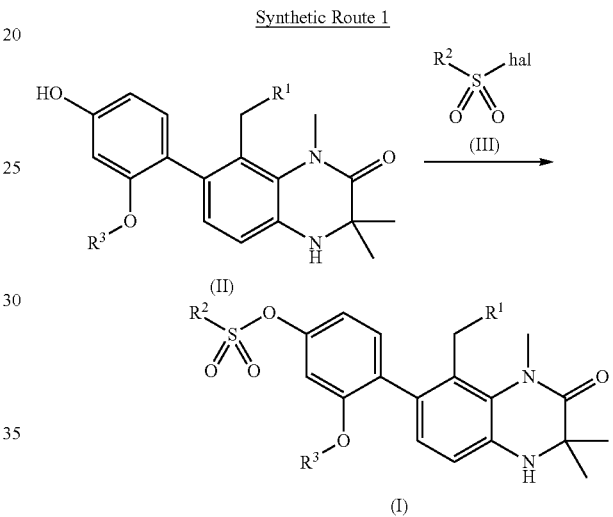

Synthetic Route 1

The present compound (I)-(a) (the compound in which $R^1$ represents (3a) in the general formula (1)) can be synthesized according to the synthetic route 2. That is, the compound (V) can be given by the reaction of the compound (IV) with a corresponding halide (III) in an organic solvent such as DMF, THF, 1,4-dioxane or methylene dichloride in the presence of a base such as triethylamine or potassium carbonate at 0° C. to 50° C. for 1 hour to 24 hours. The present compound (I)-(a) can be given by the treatment of the obtained compound (V) in an organic solvent such as DMF or methylene dichloride in the presence of a base such as piperidine at 0° C. to 50° C. for 5 minutes to 24 hours.

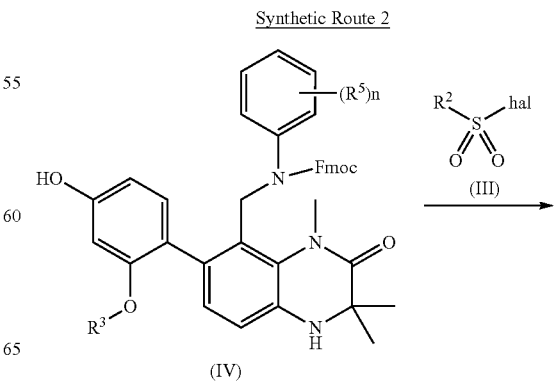

Synthetic Route 2

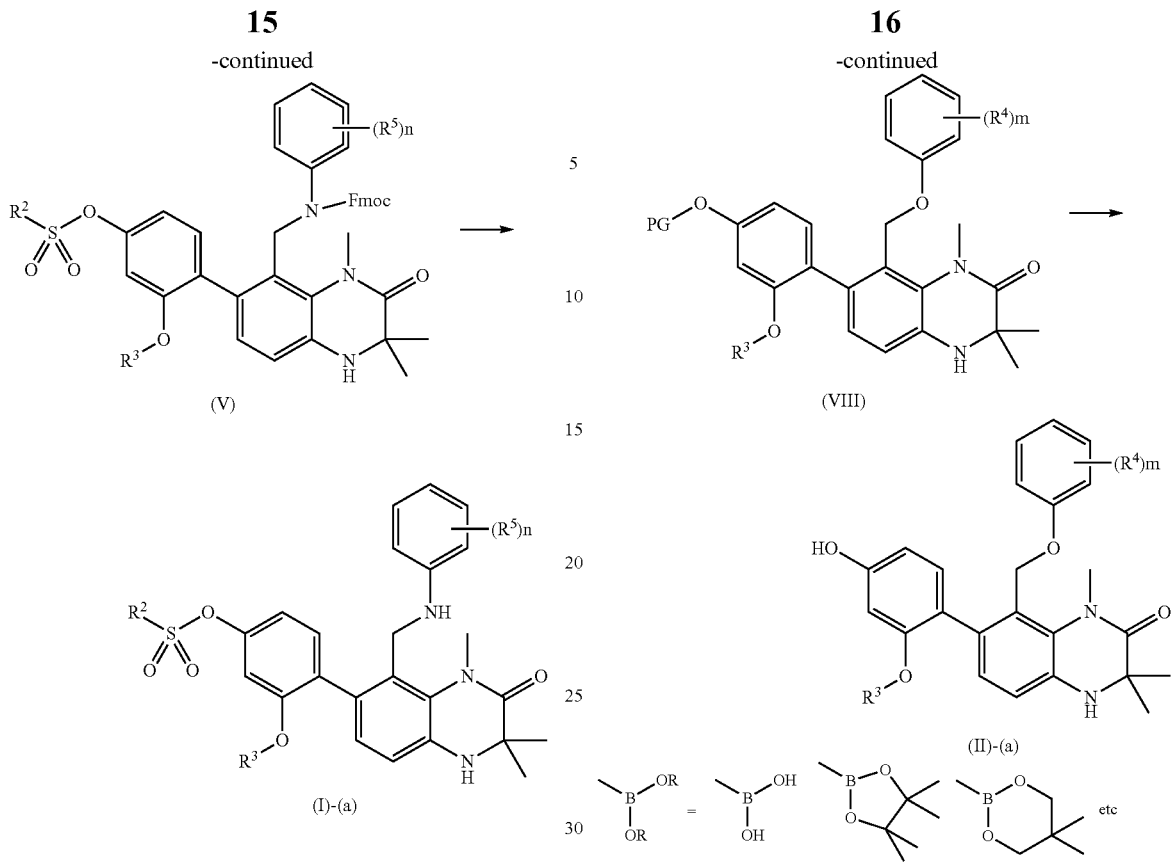

The compound (II)-(a) (the compound in which $R^1$ represents (2a) in the above compound (II)) can be synthesized according to the synthetic route 3. That is, the compound (VIII) can be given by the reaction of the compound (VI) with a corresponding boronic acid (VII) in a solvent such as DMF, 1,4-dioxane, ethanol, toluene or water in the presence of a base such as cesium carbonate, sodium carbonate, sodium hydrogen carbonate or potassium phosphate and a catalyst such as bis(triphenylphosphine)palladium (II) dichloride or tetrakis(triphenylphosphine)palladium (0) at 50° C. to 120° C. for 10 minutes to 48 hours. The compound (II)-(a) can be given by the deprotection of the protecting group in the obtained compound (VIII) in an appropriate condition.

The compound (VI) can be synthesized according to the synthetic route 4. That is, the compound (VI) can be given by the reaction of the compound (IX) with a corresponding phenol (X) in an organic solvent such as benzene or THF in the presence of a phosphine such as triphenylphosphine or tributylphosphine and a Mitsunobu reagent such as diethyl azodicarboxylate, diisopropyl azodicarboxylate or 1,1'-(azodicarbonyl)dipiperidine at room temperature for 1 hour to 2 days.

Synthetic Route 3

Synthetic Route 4

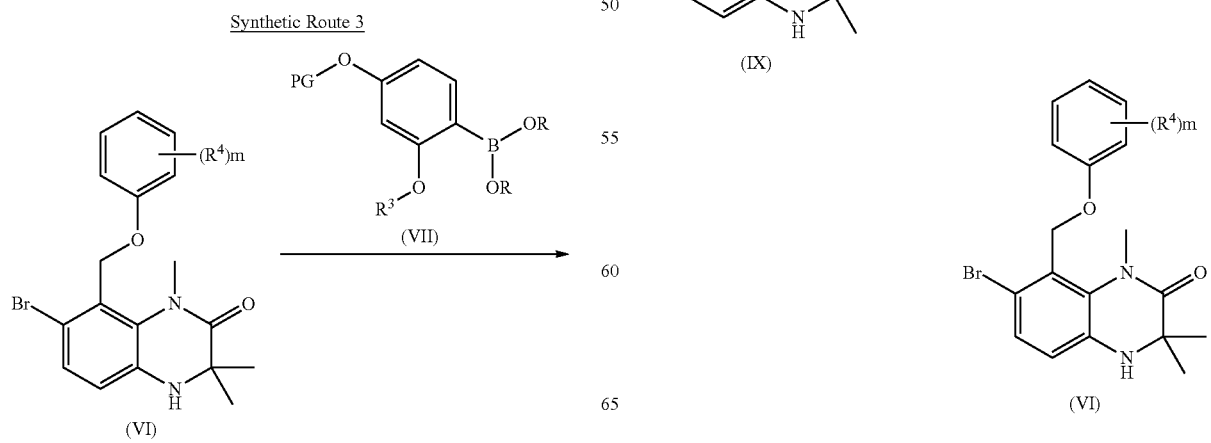

The compound (II)-(b) (the compound in which R¹ represents (4a) or (5a) in the above compound (II)) can be synthesized according to the synthetic route 5. That is, the compound (XII) can be given by the reaction of the compound (XI) with a corresponding boronic acid (VII) in a solvent such as DMF, 1,4-dioxane, ethanol, toluene or water in the presence of a base such as cesium carbonate, sodium carbonate, sodium hydrogen carbonate or potassium phosphate and a catalyst such as bis(triphenylphosphine)palladium (II) dichloride or tetrakis(triphenylphosphine)palladium (0) at 50° C. to 120° C. for 10 minutes to 48 hours. The compound (XIII) can be given by the treatment of the obtained compound (XII) in an organic solvent such as diethyl ether or THF in the presence of a reducing agent such as lithium aluminium hydride at 0° C. to 50° C. for 1 hour to 24 hours. The compound (XV) can be given by the reaction of the obtained compound (XIII) with methanesulfonyl chloride in an organic solvent such as methylene dichloride or THF in the presence of a base such as triethylamine or DIEA at 0° C. to room temperature for 30 minutes to 24 hours followed by the reaction with a corresponding carboxylic acid (XIV) in an organic solvent such as DMF, THF or ethanol in the presence of a base such as potassium carbonate, sodium hydride at 0° C. to 100° C. for 1 hour to 48 hours. The compound (XVI) can be given by the reaction of the obtained compound (XV) with methyl iodide in an organic solvent such as DMF, THF, 1,4-dioxane or methylene dichloride in the presence of a base such as cesium carbonate or potassium carbonate at 0° C. to 50° C. for 1 hour to 24 hours. The compound (II)-(b) can be given by the deprotection of the protecting group in the obtained compound (XVI) in an appropriate condition.

Synthetic Route 5

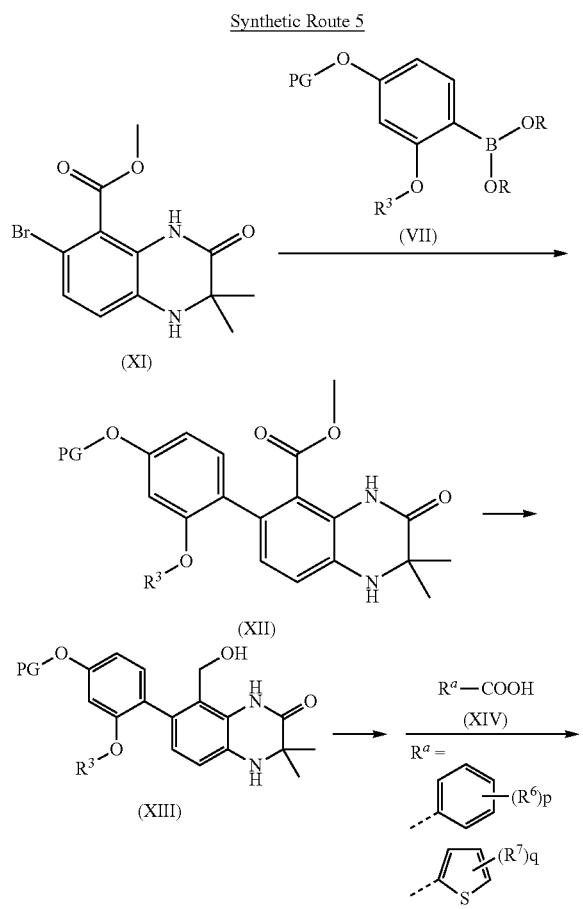

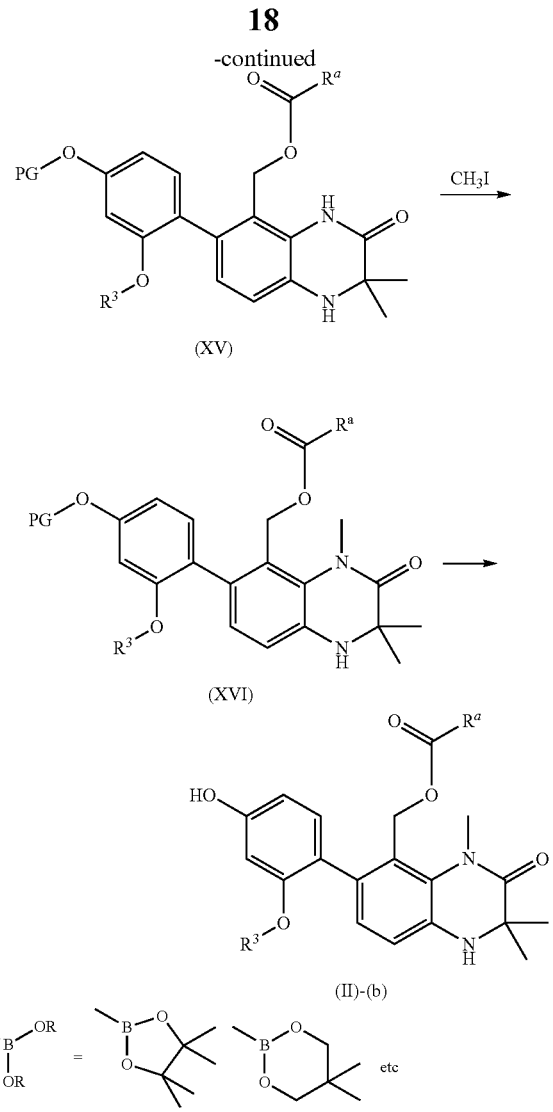

The compound (IV) can be synthesized according to the synthetic route 6. That is, the compound (XVIII) can be given by the reaction of the compound (IX) with methanesulfonyl chloride in an organic solvent such as methylene dichloride or THF in the presence of a base such as triethylamine or DIEA at 0° C. to room temperature for 30 minutes to 24 hours followed by the reaction with a corresponding amine (XVII) in an organic solvent such as DMF, THF or ethanol in the presence of a base such as potassium carbonate or sodium hydride at 0° C. to 100° C. for 1 hour to 48 hours. The compound (XIX) can be given by the reaction of the obtained compound (XVIII) with a corresponding boronic acid (VII) in a solvent such as DMF, 1,4-dioxane, ethanol, toluene or water in the presence of a base such as cesium carbonate, sodium carbonate, sodium hydrogen carbonate or potassium phosphate and a catalyst such as bis(triphenylphosphine)palladium (II) dichloride or tetrakis(triphenylphosphine)palladium (0) at 50° C. to 120° C. for 1 hour to 48 hours. The compound (XX) can be given by the reaction of the obtained compound (XIX) with 9-fluorenylmethoxycarbonyl chloride in a solvent such as 1,4-dioxane or water in the presence of a base such as sodium hydrogen carbonate at 0° C. to 50° C. for 1 hour to 24 hours. The compound (IV) can be given by the deprotection of the protective group in the obtained compound (XX) in an appropriate condition.

Synthetic Route 6

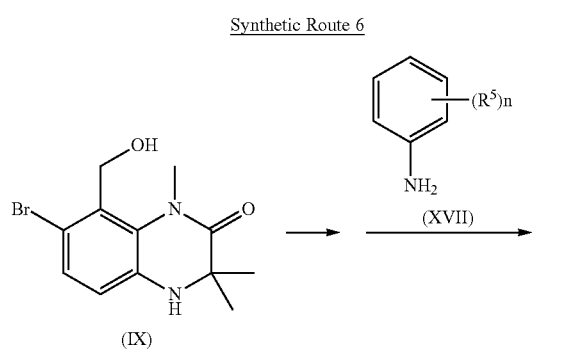

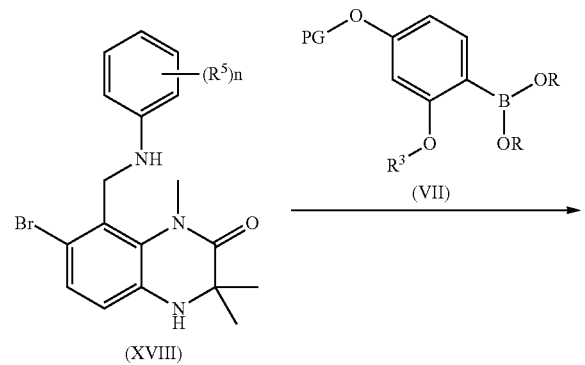

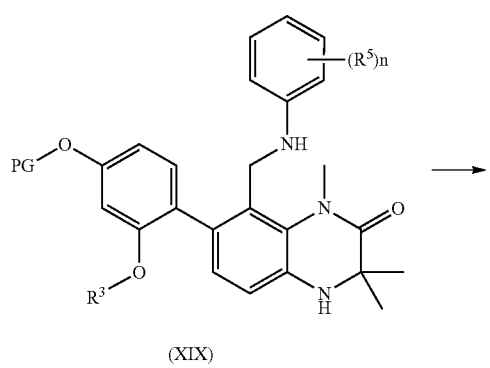

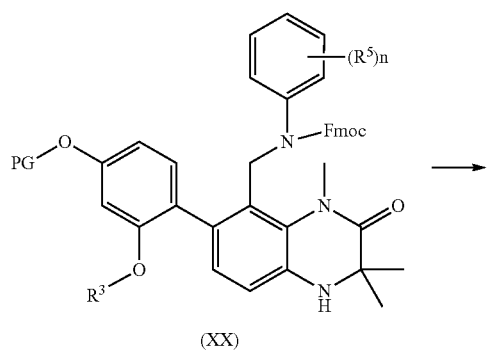

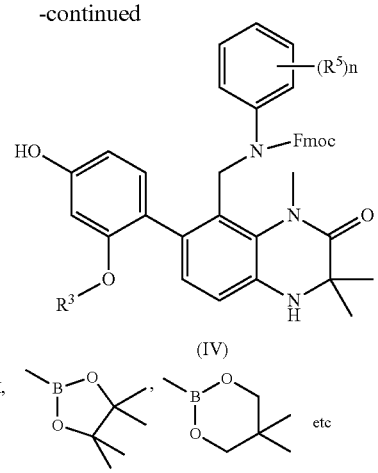

The above compound (IX) and (XI) can be synthesized according to the synthetic route 7. That is, the compound (XXII) can be given by the treatment of the compound (XXI) in an organic solvent such as methanol, ethanol or DMF in the presence of a reducing agent such as tin(II) chloride or iron at 50° C. to 120° C. for 1 hour to 12 hours. The compound (XXIII) can be given by the treatment of the obtained compound (XXII) with an acetylation agent such as acetyl chloride or acetic anhydride in an organic solvent such as methylene dichloride or THF in the presence of a base such as triethylamine or DIEA at 0° C. to 50° C. for 1 hour to 12 hours. The compound (XXIV) can be given by the reaction of the obtained compound (XXIII) with nitric acid in a solvent such as water in the presence of an acid such as sulfuric acid at −20° C. to room temperature for 30 minutes to 12 hours. The compound (XXV) can be given by the treatment of the obtained compound (XXIV) in an organic solvent such as methanol in the presence of an acid such as boron trifluoride diethylether complex at 50° C. to the temperature under reflux for 1 hour to 12 hours. The compound (XXVII) can be given by the reaction of the obtained compound (XXV) with a corresponding halide (XXVI) in the presence of a base such as cesium carbonate or potassium carbonate at 50° C. to 120° C. for 1 hour to 120 hours. The compound (XI) can be given by the treatment of the obtained compound (XXVII) in an organic solvent such as methanol, ethanol or DMF in the presence of a reducing agent such as tin(II) chloride or iron at 50° C. to 120° C. for 1 hour to 12 hours. The compound (XXVIII) can be given by the treatment of the obtained compound (XI) in an organic solvent such as diethyl ether or THF and in the presence of a reducing agent such as lithium aluminium hydride at 0° C. to 50° C. for 1 hour to 24 hours. The compound (IX) can be given by the reaction of the obtained compound (XXVIII) with methyl iodide in an organic solvent such as DMF, THF, 1,4-dioxane or methylene dichloride in the presence of a base such as cesium carbonate, potassium carbonate at 0° C. to 50° C. for 1 hour to 24 hours.

Synthetic Route 7

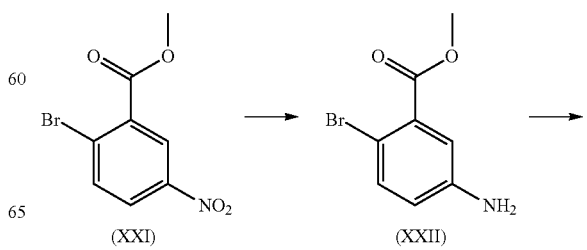

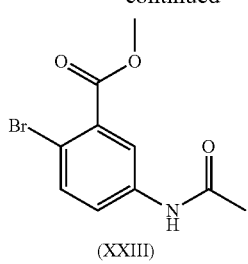

(XXIII)

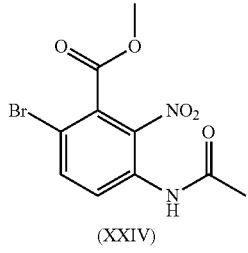

(XXIV)

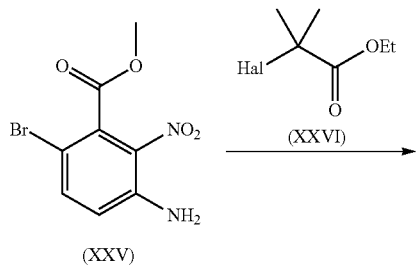

(XXV)

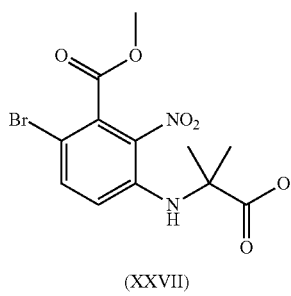

(XXVII)

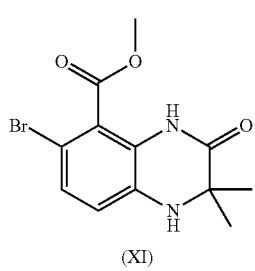

(XI)

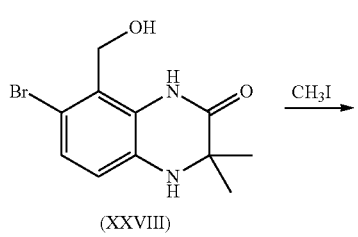

(XXVIII)

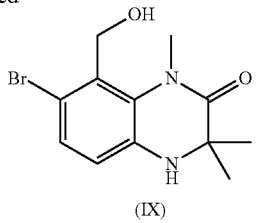

(IX)

The present compound (I)-(a) can be also synthesized according to the synthetic route 8. That is, the compound (XXI) can be given by the deprotection of the protecting group in the obtained compound (XIX) in an appropriate condition. The present compound (I)-(a) can be given by the reaction of the obtained compound (XXI) with a corresponding halide (III) in an organic solvent such as DMF, THF, 1,4-dioxane or methylene dichloride in the presence of a base such as triethylamine, potassium carbonate at 0° C. to 50° C. for 1 hour to 24 hours.

Synthetic Route 8

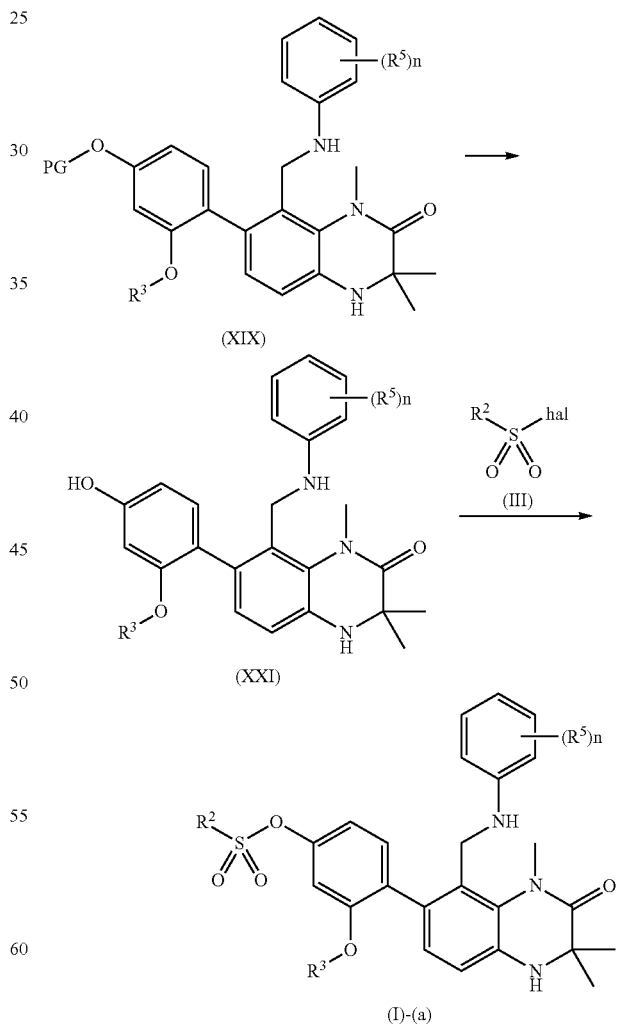

In order to find the usefulness as a glucocorticoid receptor (hereinafter referred to as "GR") agonist of the present compound, the receptor competitor assay was carried out by a fluorescence polarization method by using a GR competitor assay kit (manufactured by Invitrogen, cat No. P2816) and the binding activity to GR of the present compound was investigated. As a result, the present compound showed 80% or more of a GR binding activity to GR.

Next, the inhibitory effect on IL-6 production in human corneal epithelical cell line stimulated by Lipopolysaccharide (hereinafter referred to as "LPS" was investigated. As a result, the present compound showed an excellent inhibitory effect on IL-6 production, that is, a GR agonistic effect.

The present compound was found to be useful as a GR agonist, and a therapeutic agent for the diseases to which GR agonists such as steroids are effective, especially the inflammatory diseases (bone-joint disorders, ocular inflammatory diseases and the like).

Further, in order to evaluate the possibility as a therapeutic agent for anterior ocular inflammatory diseases of the present compound, the inhibitory effect of the present compound on dye leakages in allergic conjunctivitis model in mice was examined. As a result, the present compound showed the inhibitory effect on the vascular hyper-permeability.

Therefore the present compound was found to be useful as a therapeutic agent for anterior ocular inflammatory diseases, especially allergic ocular diseases such as allergic conjunctivitis.

Furthermore, in order to evaluate the possibility as a therapeutic agent for posterior ocular inflammatory diseases of the present compound, the choroidal neovascularization inhibitory effect of the present compound in choroidal neovascularization model in rats was examined. As a result, the present compound showed the choroidal neovascularization inhibitory effect.

Therefore, the present compound was found to be useful as a therapeutic agent for posterior ocular inflammatory disease, especially retinal diseases such as age-related macular degeneration, diabetic retinopathy, diabetic macular edema and the like.

Furthermore in order to evaluate the possibility as a therapeutic agent for inflammatory bone-joint disorders of the present compound, the inhibitory effect of the present compound on paw edema in carrageenan paw edema model in rats. As a result, the present compound showed an excellent inhibitory effect on paw edema.

Therefore, the present compound was found to be useful as a therapeutic agent for inflammatory bone-joint disorders, especially rheumatoid arthritis and osteoarthritis.

A detailed explanation of this matter will be described in the section of "Pharmacological Test" in Examples described below.

The present compound can be administered either orally or parenterally. Examples of the dosage form include a tablet, a capsule, a granule, a powder, an injection, an eye drop, a suppository, a percutaneous absorption preparation, an ointment, an aerosol (including an inhalant) and the like and they can be prepared using a commonly used technique.

For example, an oral preparation such as a tablet, a capsule, a granule or a powder can be prepared by optionally selecting and combining a necessary amount of an excipient such as lactose, mannitol, starch, crystalline cellulose, light silicic anhydride, calcium carbonate or calcium hydrogen phosphate; a lubricant such as stearic acid, magnesium stearate or talc; a binder such as starch, hydroxypropyl cellulose, hydroxypropylmethyl cellulose or polyvinylpyrrolidone; a disintegrant such as carboxymethyl cellulose, low-substituted hydroxypropylmethyl cellulose or calcium citrate; a coating agent such as hydroxypropylmethyl cellulose, macrogol or a silicone resin; a stabilizer such as ethyl p-hydroxybenzoate or benzyl alcohol; a corrigent such as a sweetener, a sour agent or a flavor, or the like.

A parenteral preparation such as an injection or an eye drop can be prepared by optionally selecting and combining a necessary amount of a tonicity agent such as sodium chloride, concentrated glycerin, propylene glycol, polyethylene glycol, potassium chloride, sorbitol or mannitol; a buffer such as sodium phosphate, sodium hydrogen phosphate, sodium acetate, citric acid, glacial acetic acid or trometamol; a surfactant such as polysorbate 80, polyoxy 40 stearate or polyoxyethylene hydrogenated castor oil 60; a stabilizer such as sodium citrate or sodium edetate; a preservative such as benzalkonium chloride, paraben, benzothonium chloride, p-hydroxybenzoate ester, sodium benzoate, chlorobutanol or sorbic acid; a pH adjusting agent such as hydrochloric acid, citric acid, phosphoric acid, glacial acetic acid, sodium hydroxide, sodium carbonate or sodium hydrogen carbonate; a soothing agent such as benzyl alcohol, or the like.

The dose of the present compound can be appropriately selected depending on the kinds of the diseases, symptoms, age, dosage form or the like. For example, in the case of an oral preparation, it can be administered in an amount of generally 0.01 to 1000 mg, preferably 1 to 100 mg per day in a single dose or several divided doses. Further, in the case of an eye drop, a preparation containing the present compound at a concentration of generally 0.0001% to 10% (w/v), preferably 0.01% to 5% (w/v) can be administered in a single dose or several divided doses.

Hereinafter, Production Examples of the present compound, Preparation Examples and results of Pharmacological Test will be described. However, these examples are described for the purpose of understanding the present invention better and are not meant to limit the scope of the present invention.

PRODUCTION EXAMPLE

Reference Example 1

7-Bromo-8-hydroxymethyl-1,3,3-trimethyl-3,4-dihydro-1H-quinoxalin-2-one (Reference Compound No. 1)

Methyl 5-amino-2-bromobenzoate (Reference Compound No. 1-(1))

Methyl 2-bromo-5-nitrobenzoate (25.3 g, 97.3 mmol) was dissolved in anhydrous methanol (500 mL), tin (II) chloride (93.3 g, 487 mmol) was added thereto, and then the reaction mixture was refluxed for 2 hours. The reaction mixture was cooled down, ethyl acetate (500 mL) and water (100 mL) were added thereto, the mixture was neutralized with 4N aqueous sodium hydroxide solution, and then filtered on celite. The filtrate was concentrated under reduced pressure, ethyl acetate (200 mL) was added thereto, and then the mixture was washed with saturated aqueous sodium hydrogen carbonate solution (200 mL, twice), water (200 mL), and saturated brine (200 mL) successively. The organic layer was dried over anhydrous magnesium sulfate and the solvent was removed under reduced pressure to give the titled reference compound (21.0 g) as a pale yellow oil. (Yield 94%)

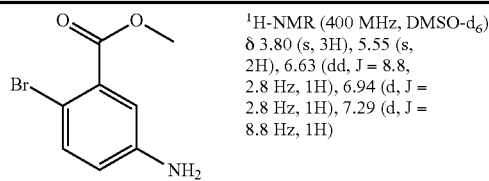

$^1$H-NMR (400 MHz, DMSO-$d_6$)
δ 3.80 (s, 3H), 5.55 (s, 2H), 6.63 (dd, J = 8.8, 2.8 Hz, 1H), 6.94 (d, J = 2.8 Hz, 1H), 7.29 (d, J = 8.8 Hz, 1H)

Methyl 5-acetylamino-2-bromobenzoate (Reference Compound No. 1-(2))

Methyl 5-amino-2-bromobenzoate (Reference Compound No. 1-(1), 21.0 g, 91.2 mmol) and triethylamine (19.0 mL, 137 mmol) were dissolved in anhydrous dichloromethane (450 mL), acetyl chloride (13.0 mL, 182 mmol) was added dropwise in this order over 30 minutes under ice cooling, and then the mixture was stirred at 0° C. for 2 hours. The reaction mixture was washed with water (200 mL, twice), saturated aqueous sodium hydrogen carbonate solution (200 mL, twice), and saturated brine (200 mL) successively, dried over anhydrous magnesium sulfate, and then the solvent was removed under reduced pressure. The obtained residue was filtered with hexane-ethyl acetate (20:1) to give the titled reference compound (24.2 g) as a pale yellow solid. (Yield 98%)

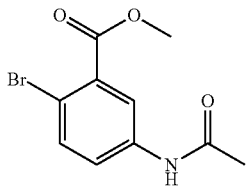

¹H-NMR (400 MHz, DMSO-d₆) δ 2.06 (s, 3H), 3.86 (s, 3H), 7.63-7.66 (m, 2H), 8.07 (s, 1H), 10.25 (s, 1H)

Methyl 3-acetylamino-6-bromo-2-nitrobenzoate (Reference Compound No. 1-(3))

To conc. sulfuric acid (150 mL), methyl 5-acetylamino-2-bromobenzoate (Reference Compound No. 1-(2), 18.5 g, 68.1 mmol) was added portionwise at 0° C., and conc. nitric acid (150 mL) was added dropwise thereto over 1 hour. The reaction mixture was stirred for 30 minutes, poured into iced water (1 L), and then the whole was extracted with ethyl acetate (500 mL, twice). The organic layer was washed with water (1 L, twice), saturated aqueous sodium hydrogen carbonate solution (1 L), and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (13.4 g) as a yellow solid. (Yield 62%)

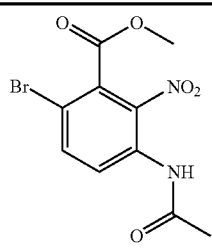

¹H-NMR (400 MHz, DMSO-d₆) δ 2.05 (s, 3H), 3.87 (s, 3H), 7.55 (d, J = 8.8 Hz, 1H), 8.02 (d, J = 8.8 Hz, 1H), 10.48 (s, 1H)

Methyl 3-amino-6-bromo-2-nitrobenzoate (Reference Compound No. 1-(4))

Methyl 3-acetylamino-6-bromo-2-nitrobenzoate (Reference Compound No. 1-(3), 13.4 g, 42.2 mmol) was dissolved in methanol (240 mL), boron trifluoride diethyl etherate complex (24.0 mL, 190 mmol) was added thereto, and then the mixture was refluxed for 2.5 hours. After the reaction mixture was neutralized with sodium hydrogen carbonate (48 g), the mixture was concentrated under reduced pressure. After ethyl acetate (500 mL) and water (700 mL) were added thereto and the mixture was partitioned, the ethyl acetate layer was washed with water (700 mL) and saturated brine (700 mL) successively, dried over anhydrous magnesium sulfate, and then the solvent was removed under reduced pressure to give the titled reference compound (11.6 g) as an orange solid. (Yield 100%)

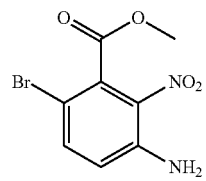

¹H-NMR (500 MHz, CDCl₃) δ 3.98 (s, 3H), 6.15 (br s, 2H), 6.78 (d, J = 9.2 Hz, 1H), 7.48 (d, J = 9.2 Hz, 1H)

Methyl 6-bromo-3-[(2-ethoxycarbonyl)propan-2-yl]amino-2-nitrobenzoate (Reference Compound No. 1-(5))

A mixture of methyl 3-amino-6-bromo-2-nitrobenzoate (Reference Compound No. 1-(4), 11.6 g, 42.0 mmol), ethyl 2-bromoisobutyrate (60.4 mL, 412 mmol), potassium iodide (7.76 g, 46.2 mmol) and cesium carbonate (56.1 g, 172 mmol) was stirred at 85° C. for 4 days. After cooling down, ethyl acetate (500 mL) and water (500 mL) were added thereto, the mixture was partitioned, and then the water layer was extracted with ethyl acetate (300 mL). The organic layer was combined, washed with water (1 L, twice) and saturated brine (1 L) successively, dried over anhydrous magnesium sulfate, and then the solvent was removed under reduced pressure. The obtained residue was purified by silica gel column chromatography (hexane-ethyl acetate) to give the titled reference compound (5.08 g) as an orange oil. (Yield 31%)

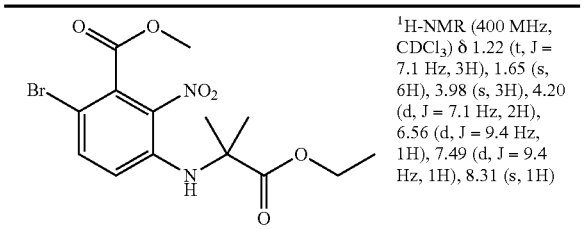

¹H-NMR (400 MHz, CDCl₃) δ 1.22 (t, J = 7.1 Hz, 3H), 1.65 (s, 6H), 3.98 (s, 3H), 4.20 (d, J = 7.1 Hz, 2H), 6.56 (d, J = 9.4 Hz, 1H), 7.49 (d, J = 9.4 Hz, 1H), 8.31 (s, 1H)

7-Bromo-8-methoxycarbonyl-3,3-dimethyl-3,4-dihydro-1H-quinoxalin-2-one (Reference Compound No. 1-(6))

Methyl 6-bromo-3-[(2-ethoxycarbonyl)propan-2-yl]amino-2-nitrobenzoate (Reference Compound No. 1-(5), 105 mg, 0.26 mmol) was dissolved in anhydrous ethanol (4.5 mL), tin (II) chloride (247 mg, 1.30 mmol) was added thereto, and then the reaction mixture was refluxed for 5 hours. After cooling down, ethyl acetate (25 mL) was added to the reaction mixture, the mixture was neutralized with aqueous sodium hydrogen carbonate solution, and then filtered on celite. After the filtrate was partitioned, the water layer was extracted with ethyl acetate (10 mL, twice), the combined organic layer was washed with water (50 mL, twice) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (56.3 mg) as a pale yellow solid. (Yield 70%)

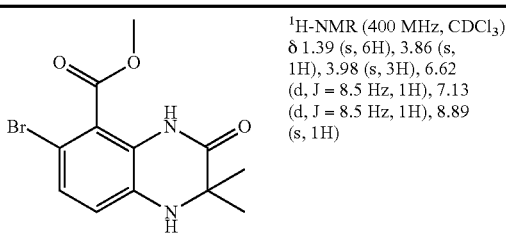

¹H-NMR (400 MHz, CDCl₃) δ 1.39 (s, 6H), 3.86 (s, 1H), 3.98 (s, 3H), 6.62 (d, J = 8.5 Hz, 1H), 7.13 (d, J = 8.5 Hz, 1H), 8.89 (s, 1H)

7-Bromo-8-hydroxymethyl-3,3-dimethyl-3,4-dihydro-1H-quinoxalin-2-one (Reference Compound No. 1-(7))

Lithium aluminium hydride (38.5 mg, 1.01 mmol) was suspended in anhydrous tetrahydrofuran (0.5 mL) under nitrogen atmosphere. An anhydrous tetrahydrofuran solution (1.5 mL) of 7-bromo-8-methoxycarbonyl-3,3-dimethyl-3,4-dihydro-1H-quinoxalin-2-one (Reference Compound No. 1-(6), 101 mg, 0.323 mmol) was added dropwise thereto at 0° C., and the mixture was stirred for 1 hour at the same temperature. Ethyl acetate (10 mL), water (10 mL), and 1N aqueous HCl solution (2 mL) were added to the reaction mixture successively and the mixture was partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (67.4 mg) as an orange amorphous product. (Yield 74%)

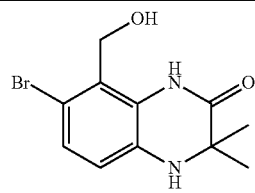

¹H-NMR (400 MHz, CDCl₃) δ 1.39 (s, 6H), 3.18 (br s, 1H) 3.75, (s, 1H), 4.99 (d, J = 9.5 Hz, 2H), 6.51 (d, J = 8.3 Hz, 1H), 7.07 (d, J = 8.3 Hz, 1H), 9.40 (s, 1H)

7-Bromo-8-hydroxymethyl-1,3,3-trimethyl-3,4-dihydro-1H-quinoxalin-2-one (Reference Compound No. 1)

A mixture of 7-bromo-8-hydroxymethyl-3,3-dimethyl-3,4-dihydro-1H-quinoxalin-2-one (Reference Compound No. 1-(7), 62.7 mg, 0.220 mmol), methyl iodide (68.6 μL, 1.10 mmol), and cesium carbonate (180 mg, 0.552 mmol) was suspended in anhydrous N,N-dimethylformamide (1 mL) and stirred at room temperature for 2.5 hours. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (45.5 mg) as an orange amorphous product. (Yield 69%)

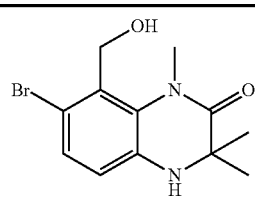

¹H-NMR (400 MHz, CDCl₃) δ 1.31 (s, 6H), 3.56 (s, 3H), 3.77 (br s, 1H), 4.73 (d, J = 7.1 Hz, 2H), 6.57 (d, J = 8.4 Hz, 1H), 7.17 (d, J = 8.4 Hz, 1H)

Reference Example 2

7-Bromo-8-chloromethyl-1,3,3-trimethyl-3,4-dihydro-1H-quinoxalin-2-one (Reference Compound No. 2)

7-Bromo-8-hydroxymethyl-1,3,3-trimethyl-3,4-dihydro-1H-quinoxalin-2-one (Reference Compound No. 1, 37.5 mg, 0.125 mmol) was dissolved in anhydrous dichloromethane (1 mL), and triethylamine (20.9 μL, 0.150 mmol) and methanesulfonyl chloride (10.7 μL, 0.138 mmol) were added thereto successively. The reaction mixture was stirred at room temperature overnight. Ethyl acetate (10 mL) and water (10 mL) were added to the reaction mixture and partitioned. The organic layer was washed with saturated brine (10 mL), dried over anhydrous magnesium sulfate, and then the solvent was removed under reduced pressure. The obtained residue was purified by silica gel column chromatography (hexane-ethyl acetate) to give the titled reference compound (28.7 mg) as an orange amorphous product. (Yield 72%)

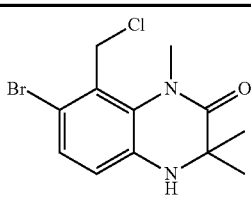

¹H-NMR (400 MHz, CDCl₃) δ 1.30 (s, 6H), 3.55 (s, 3H), 3.76 (br s, 1H), 4.76 (s, 2H), 6.61 (d, J = 8.4 Hz, 1H), 7.23 (d, J = 8.4 Hz, 1H)

Reference Example 3

7-Bromo-8-(5-fluoro-2-methylphenoxymethyl)-1,3,3-trimethyl-3,4-dihydro-1H-quinoxalin-2-one (Reference Compound No. 3-1)

A mixture of 7-bromo-8-hydroxymethyl-1,3,3-trimethyl-3,4-dihydro-1H-quinoxalin-2-one (Reference Compound No. 1, 805 mg, 2.69 mmol), 5-fluoro-2-methylphenol (382 μL, 3.50 mmol), and tri-n-butylphosphine (874 μL, 3.50 mmol) was dissolved in anhydrous tetrahydrofuran (25 mL), 1,1'-(azodicarbonyl)dipiperidine (883 mg, 3.50 mmol) was added thereto, and then the mixture was stirred at room temperature for 1 hour. 5-Fluoro-2-methylphenol (382 μL, 3.50 mmol), tri-n-butylphosphine (874 μL, 3.50 mmol), and 1,1'-(azodicarbonyl)dipiperidine (890 mg, 3.53 mmol) were added thereto and it was furthermore stirred for 20 minutes. After hexane (15 mL) was added to the reaction mixture and the precipitated solids were filtered out, the filtrate was concentrated under reduced pressure and the obtained residue was purified by silica gel column chromatography (hexane-ethyl acetate) to give the titled reference compound (900 mg) as a colorless solid. (Yield 82%)

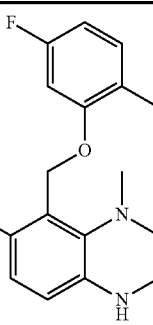

¹H-NMR (400 MHz, CDCl₃) δ 1.24 (s, 6H), 2.13 (s, 3H), 3.41 (s, 3H), 3.78 (br s, 1H), 5.16 (s, 2H), 6.54-6.57 (m, 1H), 6.58 (d, J = 9.5 Hz, 1H), 6.62 (d, J = 8.5 Hz, 1H), 7.05 (t, J = 7.6 Hz, 1H), 7.23 (d, J = 8.5 Hz, 1H)

Using any compounds among Reference Compounds No. 1 and 12-2, and commercially available compounds, the following Reference Compounds No. 3-2 to 3-4 were obtained by a method similar to that of Reference Compound No. 3-1.

| Compound | ¹H-NMR |
|---|---|
| 7-Bromo-8-(2-methoxy-5-nitro-phenoxymethyl)-1,3,3-trimethyl-3,4-dihydro-1H-quinoxalin-2-one (Reference Compound No. 3-2) 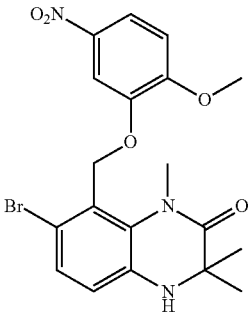 [SMILES: COc1ccc([N+](=O)[O-])cc1OCc1c(Br)ccc2c1N(C)C(=O)C(C)(C)N2] | ¹H-NMR (500 MHz, CDCl₃) δ 1.25 (s, 6H), 3.46 (s, 3H), 3.78 (s, 1H), 3.94 (s, 3H), 5.26 (s, 2H), 6.63 (d, J = 8.4 Hz, 1H), 6.93 (d, J = 9.1 Hz, 1H), 7.24 (d, J = 8.4 Hz, 1H), 7.85 (d, J = 2.5 Hz, 1H), 7.95 (dd, J = 9.1, 2.5 Hz, 1H) |
| 7-Bromo-8-(2-methyl-5-nitro-phenoxymethyl)-1,3,3-trimethyl-3,4-dihydro-1H-quinoxalin-2-one (Reference Compound No. 3-3) 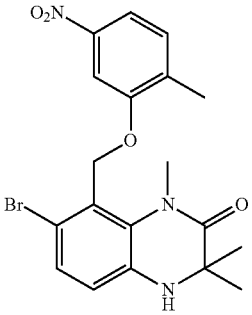 [SMILES: Cc1ccc([N+](=O)[O-])cc1OCc1c(Br)ccc2c1N(C)C(=O)C(C)(C)N2] | ¹H-NMR (400 MHz, CDCl₃) δ 1.25 (s, 6H), 2.28 (s, 3H), 3.41 (s, 3H), 3.81 (s, 1H), 5.29 (s, 2H), 6.64 (d, J = 8.3 Hz, 1H), 7.26 (d, J = 8.3 Hz, 1H), 7.28 (d, J = 8.3 Hz, 1H), 7.72 (d, J = 2.2 Hz, 1H), 7.79 (dd, J = 8.3, 2.2 Hz, 1H) |
| 7-(2-Methoxy-4-methoxymethoxyphenyl)-8-(4-methyl-benzoyloxymethyl)-1,3,3-trimethyl-3,4-dihydro-1H-quinoxalin-2-one (Reference Compound No. 3-4) 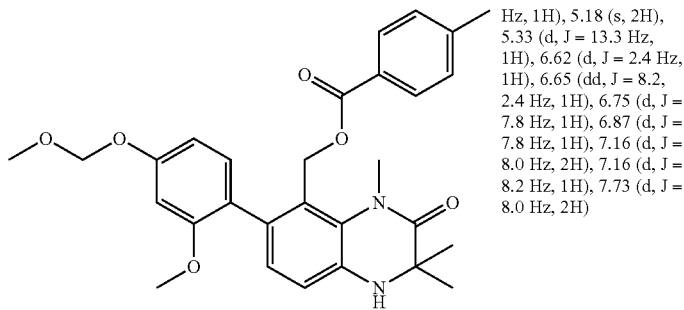 | ¹H-NMR (400 MHz, CDCl₃) δ 1.19 (s, 3H), 1.42 (s, 3H), 2.36 (s, 3H), 3.45 (s, 3H), 3.50 (s, 3H), 3.74 (s, 3H), 3.76 (s, 1H), 5.18 (d, J = 13.3 Hz, 1H), 5.18 (s, 2H), 5.33 (d, J = 13.3 Hz, 1H), 6.62 (d, J = 2.4 Hz, 1H), 6.65 (dd, J = 8.2, 2.4 Hz, 1H), 6.75 (d, J = 7.8 Hz, 1H), 6.87 (d, J = 7.8 Hz, 1H), 7.16 (d, J = 8.0 Hz, 2H), 7.16 (d, J = 8.2 Hz, 1H), 7.73 (d, J = 8.0 Hz, 2H) |

Reference Example 4

7-Bromo-8-(2-methoxyphenylaminomethyl)-1,3,3-trimethyl-3,4-dihydro-1H-quinoxalin-2-one (Reference Compound No. 4-1)

A mixture of 7-bromo-8-chloromethyl-1,3,3-trimethyl-3,4-dihydro-1H-quinoxalin-2-one (Reference Compound No. 2, 1.82 g, 5.73 mmol), 2-methoxyaniline (728 μL, 6.46 mmol), and potassium carbonate (1.19 g, 8.61 mmol) were suspended in anhydrous N,N-dimethylformamide (30 mL) and the mixture was stirred at 80° C. overnight. After cooling down, ethyl acetate (100 mL) and diethylether (100 mL) were added. The organic layer was washed with water (200 mL, 100 mL) and saturated brine (100 mL), dried over anhydrous magnesium sulfate, and then the solvent was removed under reduced pressure. The obtained residue was purified by silica gel column chromatography (hexane-ethyl acetate) to give the titled reference compound (1.45 g) as a pale yellow amorphous product. (Yield 63%)

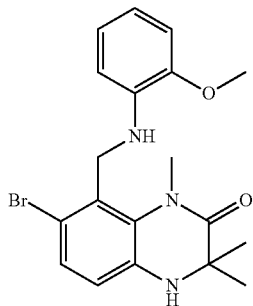 [SMILES: COc1ccccc1NCc1c(Br)ccc2c1N(C)C(=O)C(C)(C)N2]

| | ¹H-NMR (400 MHz, CDCl₃) δ 1.29 (s, 6H), 3.50 (s, 3H), 3.74 (s, 1H), 3.84 (s, 3H), 4.30 (d, J = 5.6 Hz, 2H), 4.73 (t, J = 5.6 Hz, 1H), 6.57 (d, J = 8.3 Hz, 1H), 6.67 (dd, J = 7.8, 1.5 Hz, 1H), 6.72 (td, J = 7.8, 1.5 Hz, 1H), 6.80 (dd, J = 7.8, 1.5 Hz, 1H), 6.89 (td, J = 7.8, 1.5 Hz, 1H), 7.21 (d, J = 8.3 Hz, 1H) |
|---|---|

Using any compounds among Reference Compound No. 2 and commercially available compounds, the following Reference Compound No. 4-2 was obtained by a method similar to that of Reference Compound No. 4-1.

| 7-Bromo-8-(5-fluoro-2-methyl-phenylaminomethyl)-1,3,3-trimethyl-3,4-dihydro-1H-quinoxalin-2-one (Reference Compound No. 4-2) 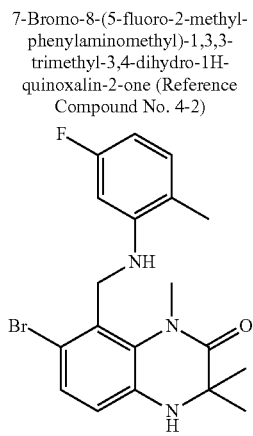 [SMILES: Cc1ccc(F)cc1NCc1c(Br)ccc2c1N(C)C(=O)C(C)(C)N2] | ¹H-NMR (500 MHz, CDCl₃) δ 1.30 (s, 6H), 2.11 (s, 3H), 3.47 (s, 3H), 3.78 (s, 1H), 4.12 (br s, 1H), 4.30 (d, J = 5.5 Hz, 2H), 6.35-6.40 (m, 2H), 6.60 (d, J = 8.6 Hz, 1H), 6.98 (t, J = 7.2 Hz, 1H), 7.22 (d, J = 8.6 Hz, 1H) |
|---|---|

Reference Example 5

5-Hydroxy-2-iodoanisole (Reference Compound No. 5)

A mixture of 3-methoxyphenol (600 mg, 4.83 mmol) and N-iodosuccinimide (1.09 g, 4.84 mmol) was dissolved in anhydrous N,N-dimethylformamide (25 mL), and the mixture was stirred at room temperature overnight. Ethyl acetate (100 mL) and diethylether (100 mL) were added. The organic layer was washed with 1% aqueous sodium thiosulfate solution (200 mL), water (100 mL), and saturated brine (50 mL), dried over anhydrous magnesium sulfate, and then the solvent was removed under reduced pressure. The obtained residue was purified by silica gel column chromatography (hexane-ethyl acetate) to give the titled reference compound (167 mg) as a colorless oil. (Yield 14%)

| 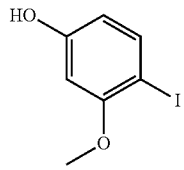 | ¹H-NMR (400 MHz, CDCl₃) δ 3.85 (s, 3H), 4.82 (s, 1H), 6.25 (dd, J = 8.4, 2.7 Hz, 1H), 6.40 (d, J = 2.7 Hz, 1H), 7.56 (d, J = 8.4 Hz, 1H) |
|---|---|

Reference Example 6

2-Iodo-5-methoxymethoxyanisole (Reference Compound No. 6)

A mixture of 5-hydroxy-2-iodoanisole (Reference Compound No. 5, 4.30 g, 17.2 mmol), chlorodimethylether (2.46 mL, 32.4 mmol), and potassium carbonate (5.94 g, 43.0 mmol) was suspended in anhydrous N,N-dimethylformamide (80 mL) and stirred at 50° C. for 1.5 hours. After cooling down, the reaction mixture was diluted with ethyl acetate (100 mL) and diethylether (200 mL). It was washed with water (300 mL), then the aqueous layer was extracted with diethylether (100 mL). After the organic layers were combined, it was washed with water (200 mL, twice) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (958 mg) as a colorless oil. (Yield 19%)

| 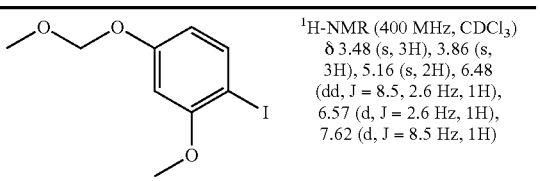 | ¹H-NMR (400 MHz, CDCl₃) δ 3.48 (s, 3H), 3.86 (s, 3H), 5.16 (s, 2H), 6.48 (dd, J = 8.5, 2.6 Hz, 1H), 6.57 (d, J = 2.6 Hz, 1H), 7.62 (d, J = 8.5 Hz, 1H) |
|---|---|

Reference Example 7

2-Methoxy-4-methoxymethoxyphenylboronic acid (Reference Compound No. 7)

A mixture of 2-iodo-5-methoxymethoxyanisole (Reference Compound No. 6, 100 mg, 0.340 mmol), bis(neopentylglycolato)diboron (115 mg, 0.509 mmol), potassium acetate (66.7 mg, 0.680 mmol), and [1,1'-bis(diphenylphosphino)ferrocene]palladium(II) dichloride dichloromethane complex (1:1) (27.8 mg, 0.034 mmol) was suspended in dimethylsulfoxide (1.5 mL), and the mixture was stirred at 80° C. for 2.5 hours. After cooling down, ethyl acetate (100 mL) and water (100 mL) were added to the reaction mixture and partitioned. The organic layer was washed with saturated brine (50 mL), dried over anhydrous magnesium sulfate, and then the solvent was removed under reduced pressure. The obtained residue was purified by silica gel column chromatography (hexane-ethyl acetate) to give the titled reference compound (57.6 mg) as a colorless solid. (Yield 80%)

| 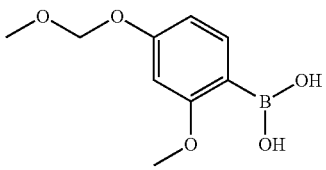 | ¹H-NMR (400 MHz, CDCl₃) δ 3.49 (s, 3H), 3.90 (s, 3H), 5.21 (s, 2H), 5.58 (s, 2H), 6.60 (d, J = 2.0 Hz, 1H), 6.70 (dd, J = 8.2, 2.0 Hz, 1H), 7.75 (d, J = 8.2 Hz, 1H) |
|---|---|

Reference Example 8

8-(5-Fluoro-2-methylphenoxymethyl)-7-(2-methoxy-4-methoxymethoxyphenyl)-1,3,3-trimethyl-3,4-dihydro-1H-quinoxalin-2-one (Reference Compound No. 8-1)

Under argon atmosphere, a mixture of 7-bromo-8-(5-fluoro-2-methylphenoxymethyl)-1,3,3-trimethyl-3,4-dihydro-1H-quinoxalin-2-one (Reference Compound No. 3-1, 2.32 g, 5.70 mmol), 2-methoxy-4-methoxymethoxyphenylboronic acid (Reference Compound No. 7, 2.43 g, 11.5 mmol), cesium carbonate (9.46 g, 29.0 mmol), and bis(triphenylphosphine)palladium (II) dichloride (415 mg, 0.591 mmol) was suspended in anhydrous N,N-dimethylformamide (25 ml) and the mixture was stirred at 80° C. for 5 hours. After cooling down, ethyl acetate (150 mL) and water (150 mL) were added and partitioned. The organic layer was washed with saturated brine (150 mL), dried over anhydrous magnesium sulfate, and then the solvent was removed under reduced pressure. The obtained residue was purified by silica gel column chromatography (hexane-ethyl acetate) to give the titled reference compound (2.73 g) as a colorless solid. (Yield 97%)

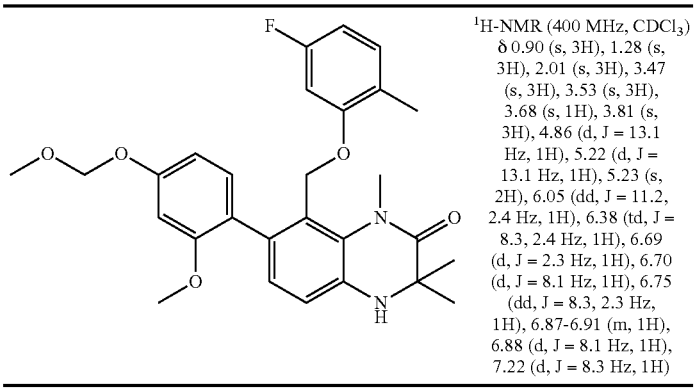

$^1$H-NMR (400 MHz, CDCl$_3$) δ 0.90 (s, 3H), 1.28 (s, 3H), 2.01 (s, 3H), 3.47 (s, 3H), 3.53 (s, 3H), 3.68 (s, 1H), 3.81 (s, 3H), 4.86 (d, J = 13.1 Hz, 1H), 5.22 (d, J = 13.1 Hz, 1H), 5.23 (s, 2H), 6.05 (dd, J = 11.2, 2.4 Hz, 1H), 6.38 (td, J = 8.3, 2.4 Hz, 1H), 6.69 (d, J = 2.3 Hz, 1H), 6.70 (d, J = 8.1 Hz, 1H), 6.75 (dd, J = 8.3, 2.3 Hz, 1H), 6.87-6.91 (m, 1H), 6.88 (d, J = 8.1 Hz, 1H), 7.22 (d, J = 8.3 Hz, 1H)

Using any compounds among Reference Compounds No. 1-(6), 3-2 to 3-3, 4-1, 4-2 and commercially available compounds, the following Reference Compounds No. 8-2 to 8-6 were obtained by a method similar to that of Reference Compound No. 8-1.

7-(2-Methoxy-4-methoxymethoxyphenyl)-8-(2-methoxy-5-nitrophenoxymethyl)-1,3,3-trimethyl-3,4-dihydro-1H-quinoxalin-2-one (Reference Compound No. 8-2)

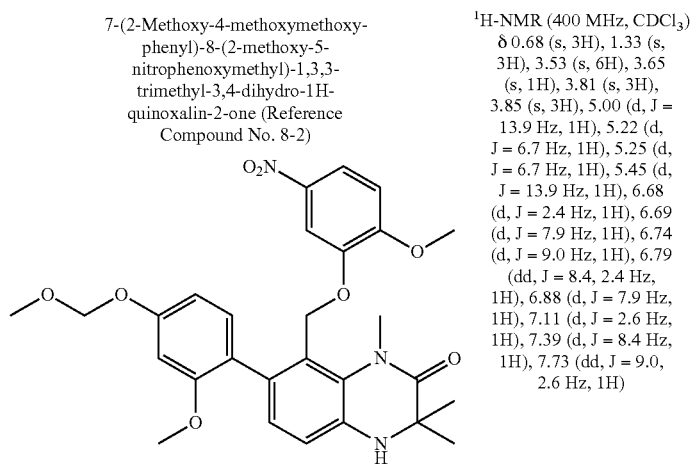

$^1$H-NMR (400 MHz, CDCl$_3$) δ 0.68 (s, 3H), 1.33 (s, 3H), 3.53 (s, 6H), 3.65 (s, 1H), 3.81 (s, 3H), 3.85 (s, 3H), 5.00 (d, J = 13.9 Hz, 1H), 5.22 (d, J = 6.7 Hz, 1H), 5.25 (d, J = 6.7 Hz, 1H), 5.45 (d, J = 13.9 Hz, 1H), 6.68 (d, J = 2.4 Hz, 1H), 6.69 (d, J = 7.9 Hz, 1H), 6.74 (d, J = 9.0 Hz, 1H), 6.79 (dd, J = 8.4, 2.4 Hz, 1H), 6.88 (d, J = 7.9 Hz, 1H), 7.11 (d, J = 2.6 Hz, 1H), 7.39 (d, J = 8.4 Hz, 1H), 7.73 (dd, J = 9.0, 2.6 Hz, 1H)

| | |
|---|---|
| 7-(2-Methoxy-4-methoxymethoxy-phenyl)-8-(2-methoxy-5-nitrophenoxymethyl)-1,3,3-trimethyl-3,4-dihydro-1H-quinoxalin-2-one (Reference Compound No. 8-3)<br>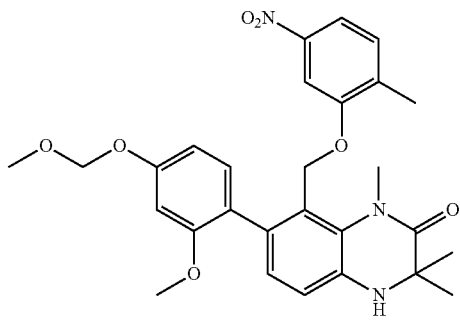 | $^1$H-NMR (400 MHz, CDCl$_3$) δ 0.61 (s, 3H), 1.36 (s, 3H), 2.17 (s, 3H), 3.51 (s, 3H), 3.53 (s, 3H), 3.66 (s, 1H), 3.83 (s, 3H), 4.99 (d, J = 14.1 Hz, 1H), 5.22 (d, J = 6.8 Hz, 1H), 5.25 (d, J = 6.8 Hz, 1H), 5.45 (d, J = 14.1 Hz, 1H), 6.69 (d, J = 2.3 Hz, 1H), 6.70 (d, J = 8.1 Hz, 1H), 6.83 (dd, J = 8.4, 2.3 Hz, 1H), 6.91 (d, J = 8.1 Hz, 1H), 7.03 (d, J = 2.2 Hz, 1H), 7.09 (d, J = 8.1 Hz, 1H), 7.45 (d, J = 8.4 Hz, 1H), 7.57 (dd, J = 8.1, 2.2 Hz, 1H)) |
| 7-(2-Methoxy-4-methoxymethoxy-phenyl)-8-(2-methoxyphenyl-aminomethyl)-1,3,3-trimethyl-3,4-dihydro-1H-quinoxalin-2-one (Reference Compound No. 8-4)<br>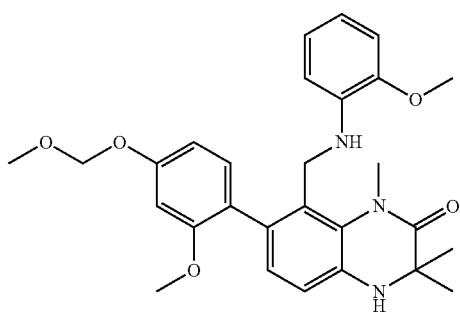 | $^1$H-NMR (500 MHz, CDCl$_3$) δ 1.16 (s, 3H), 1.42 (s, 3H), 3.46 (s, 3H), 3.50 (s, 3H), 3.70 (s, 1H), 3.73 (s, 3H), 3.77 (s, 3H), 4.13 (d, J = 5.3 Hz, 2H), 4.52 (t, J = 5.3 Hz, 1H), 5.19 (s, 2H), 6.34 (dd, J = 7.6, 1.5 Hz, 1H), 6.56 (td, J = 7.6, 1.5 Hz, 1H), 6.61 (d, J = 2.4 Hz, 1H), 6.65-6.67 (m, 2H), 6.68 (d, J = 7.9 Hz, 1H), 6.72 (td, J = 7.6, 1.5 Hz, 1H), 6.80 (d, J = 7.9 Hz, 1H), 7.07 (d, J = 8.2 Hz, 1H) |
| 8-(5-Fluoro-2-methylphenyl-aminomethyl)-7-(2-methoxy-4-methoxymethoxyphenyl)-1,3,3-trimethyl-3,4-dihydro-1H-quinoxalin-2-one (Reference Compound No. 8-5)<br>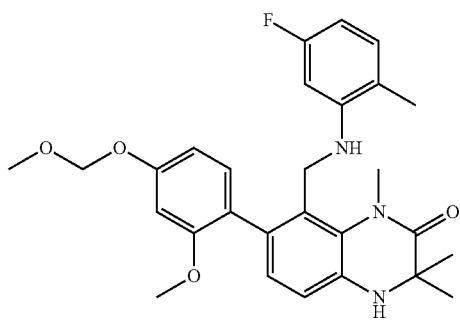 | $^1$H-NMR (400 MHz, CDCl$_3$) δ 1.17 (s, 3H), 1.40 (s, 3H), 1.85 (s, 3H), 3.42 (s, 3H), 3.51 (s, 3H), 3.73 (s, 1H), 3.77 (s, 3H), 3.83 (br s, 1H), 4.13-4.23 (m, 2H), 5.20 (s, 2H), 6.03 (dd, J = 11.7, 2.5 Hz, 1H), 6.22 (td, J = 8.4, 2.5 Hz, 1H), 6.65 (d, J = 2.3 Hz, 1H), 6.70 (d, J = 7.8 Hz, 1H), 6.71 (dd, J = 8.3, 2.3 Hz, 1H), 6.81-6.85 (m, 1H), 6.83 (d, J = 7.8 Hz, 1H), 7.11 (d, J = 8.3 Hz, 1H) |

| 8-Methoxycarbonyl-7-(2-methoxy-4-methoxymethoxyphenyl)-3,3-dimethyl-3,4-dihydro-1H-quinoxalin-2-one (Reference Compound No. 8-6) 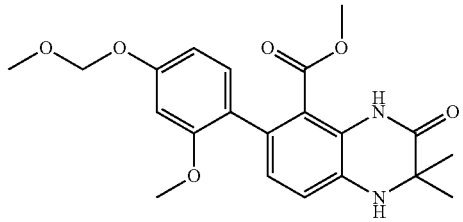 | $^1$H-NMR (500 MHz, CDCl$_3$) δ 1.42 (br s, 6H), 3.52 (s, 3H), 3.54 (s, 3H), 3.70 (s, 3H), 3.81 (br s, 1H), 5.21 (s, 2H), 6.57 (d, J = 2.1 Hz, 1H), 6.69 (dd, J = 8.2, 2.1 Hz, 1H), 6.79 (d, J = 8.2 Hz, 1H), 6.82 (d, J = 8.2 Hz, 1H), 7.12 (d, J = 8.2 Hz, 1H), 9.51 (s, 1H) |
|---|---|

Reference Example 9
8-Hydroxymethyl-7-(2-methoxy-4-methoxymethoxyphenyl)-3,3-dimethyl-3,4-dihydro-1H-quinoxalin-2-one (Reference Compound No. 9)

Lithium aluminium hydride (753 mg, 19.8 mmol) was suspended in anhydrous tetrahydrofuran (60 mL) under nitrogen atmosphere. An anhydrous tetrahydrofuran solution (20 mL) of 8-methoxycarbonyl-7-(2-methoxy-4-methoxymethoxyphenyl)-3,3-dimethyl-3,4-dihydro-1H-quinoxalin-2-one (Reference Compound No. 8-6, 4.87 g, 12.2 mmol) was added dropwise thereto at −10° C., and stirred for 40 minutes at the same temperature. After ethyl acetate (10 mL), water (10 mL), and 2N aqueous HCl solution (15 mL) were added to the reaction mixture successively, ethyl acetate (300 mL) were added thereto. Water (300 mL) was added and the whole was partitioned. The organic layer was washed with saturated brine (400 mL), dried over anhydrous magnesium sulfate, and then the solvent was removed under reduced pressure. The obtained residue was purified by silica gel column chromatography (hexane-ethyl acetate) to give the titled reference compound (1.86 g) as a yellow solid. (Yield 41%)

| 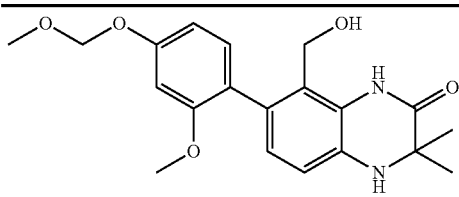 | $^1$H-NMR (400 MHz, CDCl$_3$) δ 1.38 (s, 3H), 1.49 (s, 3H), 2.13 (t, J = 6.9 Hz, 1H), 3.53 (s, 3H), 3.75 (s, 4H), 4.45 (d, J = 6.9 Hz, 2H), 5.22 (s, 2H), 6.67 (d, J = 2.7 Hz, 1H), 6.67 (d, J = 8.1 Hz, 1H), 6.72 (dd, J = 8.0, 2.7 Hz, 1H), 6.72 (d, J = 8.0 Hz, 1H), 7.07 (d, J = 8.1 Hz, 1H), 8.57 (s, 1H) |
|---|---|

Reference Example 10

8-Chloromethyl-7-(2-methoxy-4-methoxymethoxyphenyl)-3,3-dimethyl-3,4-dihydro-1H-quinoxalin-2-one (Reference Compound No. 10)

8-Hydroxymethyl-7-(2-methoxy-4-methoxymethoxyphenyl)-3,3-dimethyl-3,4-dihydro-1H-quinoxalin-2-one (Reference Compound No. 9, 495 mg, 1.33 mmol) was dissolved in anhydrous dichloromethane (10 mL), and triethylamine (250 μL, 1.80 mmol) and methanesulfonyl chloride (113 μL, 1.46 mmol) were added thereto successively. The reaction mixture was stirred at room temperature overnight. The reaction mixture was concentrated under reduced pressure. The obtained residue was purified by silica gel column chromatography (hexane-ethyl acetate) to give the titled reference compound (239 mg) as a yellow amorphous product. (Yield 46%)

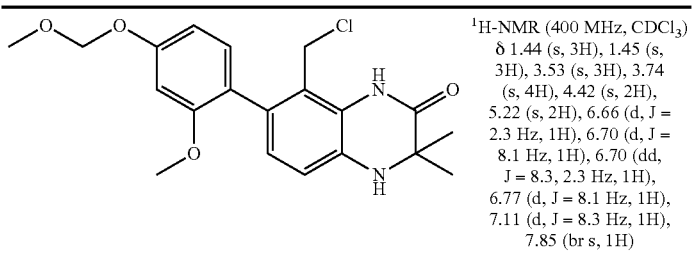

¹H-NMR (400 MHz, CDCl₃)
δ 1.44 (s, 3H), 1.45 (s, 3H), 3.53 (s, 3H), 3.74 (s, 4H), 4.42 (s, 2H), 5.22 (s, 2H), 6.66 (d, J = 2.3 Hz, 1H), 6.70 (d, J = 8.1 Hz, 1H), 6.70 (dd, J = 8.3, 2.3 Hz, 1H), 6.77 (d, J = 8.1 Hz, 1H), 7.11 (d, J = 8.3 Hz, 1H), 7.85 (br s, 1H)

Reference Example 11

7-(2-Methoxy-4-methoxymethoxyphenyl)-8-(5-methylthiophen-2-ylcarbonyloxymethyl)-3,3-dimethyl-3,4-dihydro-1H-quinoxalin-2-one (Reference Compound No. 11)

A mixture of 8-chloromethyl-7-(2-methoxy-4-methoxymethoxyphenyl)-3,3-dimethyl-3,4-dihydro-1H-quinoxalin-2-one (Reference Compound No. 10, 238 mg, 0.609 mmol), 5-methyl-2-thiophenecarboxylic acid (133 mg, 0.936 mmol), and potassium carbonate (261 mg, 1.89 mmol) was suspended in anhydrous N,N-dimethylformamide (5 mL) and stirred at 80° C. for 2 hours. The reaction mixture was diluted with ethyl acetate (100 mL). It was washed with water (100 mL) and saturated brine (100 mL) successively, dried over anhydrous magnesium sulfate, and then the solvent was removed under reduced pressure. The obtained residue was purified by silica gel column chromatography (hexane-ethyl acetate) to give the titled reference compound (264 mg) as a yellow amorphous product. (Yield 87%)

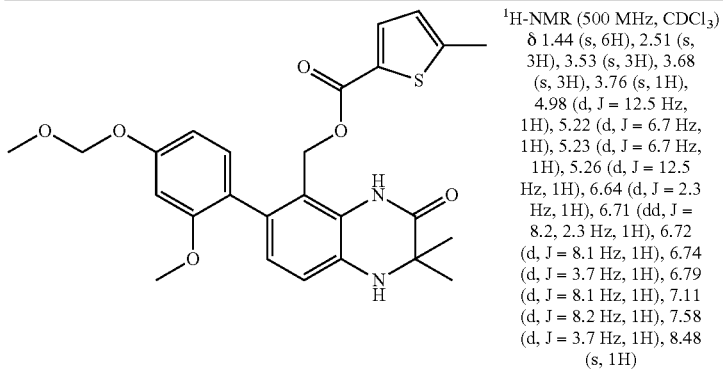

¹H-NMR (500 MHz, CDCl₃)
δ 1.44 (s, 6H), 2.51 (s, 3H), 3.53 (s, 3H), 3.68 (s, 3H), 3.76 (s, 1H), 4.98 (d, J = 12.5 Hz, 1H), 5.22 (d, J = 6.7 Hz, 1H), 5.23 (d, J = 6.7 Hz, 1H), 5.26 (d, J = 12.5 Hz, 1H), 6.64 (d, J = 2.3 Hz, 1H), 6.71 (dd, J = 8.2, 2.3 Hz, 1H), 6.72 (d, J = 8.1 Hz, 1H), 6.74 (d, J = 3.7 Hz, 1H), 6.79 (d, J = 8.1 Hz, 1H), 7.11 (d, J = 8.2 Hz, 1H), 7.58 (d, J = 3.7 Hz, 1H), 8.48 (s, 1H)

Reference Example 12

7-(2-Methoxy-4-methoxymethoxyphenyl)-8-(5-methylthiophen-2-ylcarbonyloxymethyl)-1,3,3-trimethyl-3,4-dihydro-1H-quinoxalin-2-one (Reference Compound No. 12-1)

A mixture of 7-(2-methoxy-4-methoxymethoxyphenyl)-8-(5-methylthiophen-2-ylcarbonyloxymethyl)-3,3-dimethyl-3,4-dihydro-1H-quinoxalin-2-one (Reference Compound No. 11, 1.58 g, 3.18 mmol), methyl iodide (400 μL, 6.43 mmol), and cesium carbonate (2.24 g, 6.87 mmol) was suspended in anhydrous N,N-dimethylformamide (30 mL) and stirred at room temperature for 2 hours. The reaction mixture was diluted with ethyl acetate (150 mL), washed with water (150 mL) and saturated brine (150 mL) successively, dried over anhydrous magnesium sulfate, and then the solvent was removed under reduced pressure. The obtained residue was purified by silica gel column chromatography (hexane-ethyl acetate) to give the titled reference compound (1.38 g) as a pale yellow amorphous product. (Yield 85%)

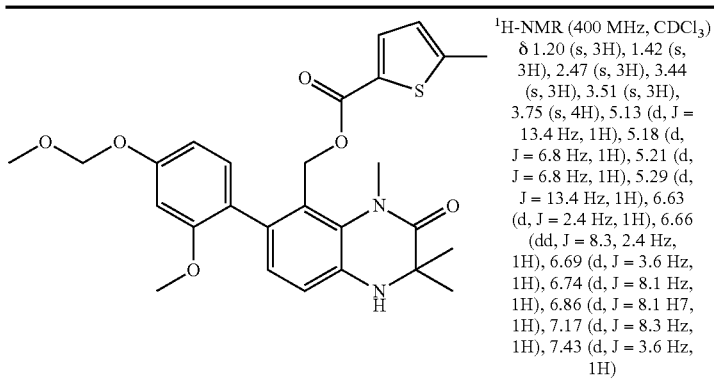

| | ¹H-NMR (400 MHz, CDCl₃) δ 1.20 (s, 3H), 1.42 (s, 3H), 2.47 (s, 3H), 3.44 (s, 3H), 3.51 (s, 3H), 3.75 (s, 4H), 5.13 (d, J = 13.4 Hz, 1H), 5.18 (d, J = 6.8 Hz, 1H), 5.21 (d, J = 6.8 Hz, 1H), 5.29 (d, J = 13.4 Hz, 1H), 6.63 (d, J = 2.4 Hz, 1H), 6.66 (dd, J = 8.3, 2.4 Hz, 1H), 6.69 (d, J = 3.6 Hz, 1H), 6.74 (d, J = 8.1 Hz, 1H), 6.86 (d, J = 8.1 H7, 1H), 7.17 (d, J = 8.3 Hz, 1H), 7.43 (d, J = 3.6 Hz, 1H) |

Using any compounds among Reference Compound No. 9 and commercially available compounds, the following Reference Compound No. 12-2 was obtained by a method similar to that of Reference Compound No. 12-1.

| 8-Hydroxymethyl-7-(2-methoxy-4-methoxymethoxyphenyl)-1,3,3-trimethyl-3,4-dihydro-1H-quinoxalin-2-one (Reference Compound No. 12-2) 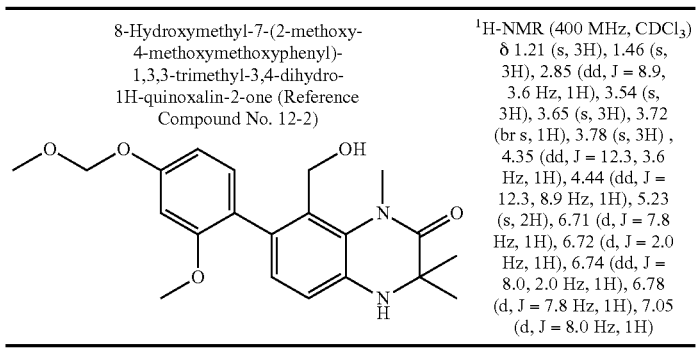 | ¹H-NMR (400 MHz, CDCl₃) δ 1.21 (s, 3H), 1.46 (s, 3H), 2.85 (dd, J = 8.9, 3.6 Hz, 1H), 3.54 (s, 3H), 3.65 (s, 3H), 3.72 (br s, 1H), 3.78 (s, 3H), 4.35 (dd, J = 12.3, 3.6 Hz, 1H), 4.44 (dd, J = 12.3, 8.9 Hz, 1H), 5.23 (s, 2H), 6.71 (d, J = 7.8 Hz, 1H), 6.72 (d, J = 2.0 Hz, 1H), 6.74 (dd, J = 8.0, 2.0 Hz, 1H), 6.78 (d, J = 7.8 Hz, 1H), 7.05 (d, J = 8.0 Hz, 1H) |

Reference Example 13

8-[N-(9-Fluorenylmethoxycarbonyl)-N-(2-methoxyphenyl)aminomethyl]-7-(2-methoxy-4-methoxymethoxyphenyl)-1,3,3-trimethyl-3,4-dihydro-1H-quinoxalin-2-one (Reference Compound No. 13)

7-(2-Methoxy-4-methoxymethoxyphenyl)-8-(2-methoxyphenylaminomethyl)-1,3,3-trimethyl-3,4-dihydro-1H-quinoxalin-2-one (Reference Compound No. 8-4, 104 mg, 0.212 mmol) and sodium hydrogen carbonate (22.0 mg, 0.262 mmol) were dissolved in a mixed solvent of 1,4-dioxane (1.5 mL) and water (1 mL), and 9-fluorenylmethoxycarbonyl chloride (60.3 mg, 0.233 mmol) was added thereto. After the reaction mixture was stirred at room temperature for 30 minutes, the mixture was diluted with ethyl acetate (50 mL). The mixture was washed with water (50 mL) and saturated brine (50 mL) successively, dried over anhydrous magnesium sulfate, and then the solvent was removed under reduced pressure. The obtained residue was purified by silica gel column chromatography (hexane-ethyl acetate) to give the titled reference compound (149 mg) as a colorless amorphous product. (Yield 99%)

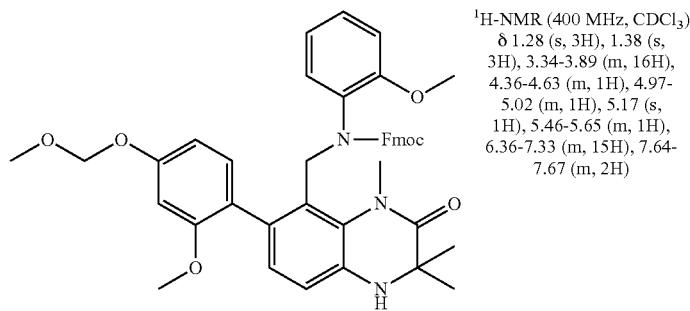

¹H-NMR (400 MHz, CDCl₃) δ 1.28 (s, 3H), 1.38 (s, 3H), 3.34-3.89 (m, 16H), 4.36-4.63 (m, 1H), 4.97-5.02 (m, 1H), 5.17 (s, 1H), 5.46-5.65 (m, 1H), 6.36-7.33 (m, 15H), 7.64-7.67 (m, 2H)

Reference Example 14

8-(5-Fluoro-2-methylphenoxymethyl)-7-(4-hydroxy-2-methoxyphenyl)-1,3,3-trimethyl-3,4-dihydro-1H-quinoxalin-2-one (Reference Compound No. 14-1)

8-(5-Fluoro-2-methylphenoxymethyl)-7-(2-methoxy-4-methoxymethoxyphenyl)-1,3,3-trimethyl-3,4-dihydro-1H-quinoxalin-2-one (Reference Compound No. 8-1, 2.73 g, 5.52 mmol) was dissolved in a mixed solution of 1,4-dioxane (25 mL) and methanol (5 mL), and 4N HCl/1,4-dioxane solution (7.0 mL, 28 mmol) was added thereto. After the reaction mixture was stirred at room temperature for 1 hour, the mixture was diluted with ethyl acetate (130 mL). The mixture was washed with aqueous sodium hydrogen carbonate solution (130 mL) and saturated brine (100 mL) successively, dried over anhydrous magnesium sulfate, and then the solvent was removed under reduced pressure to give the titled reference compound (2.41 g) as a pale yellow solid. (Yield 97%)

| 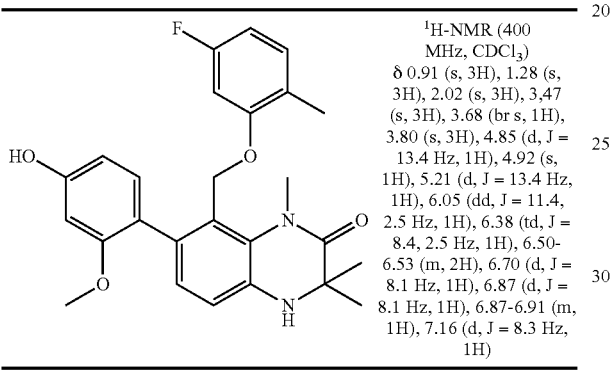 | $^1$H-NMR (400 MHz, CDCl$_3$) δ 0.91 (s, 3H), 1.28 (s, 3H), 2.02 (s, 3H), 3.47 (s, 3H), 3.68 (br s, 1H), 3.80 (s, 3H), 4.85 (d, J = 13.4 Hz, 1H), 4.92 (s, 1H), 5.21 (d, J = 13.4 Hz, 1H), 6.05 (dd, J = 11.4, 2.5 Hz, 1H), 6.38 (td, J = 8.4, 2.5 Hz, 1H), 6.50-6.53 (m, 2H), 6.70 (d, J = 8.1 Hz, 1H), 6.87 (d, J = 8.1 Hz, 1H), 6.87-6.91 (m, 1H), 7.16 (d, J = 8.3 Hz, 1H) |
|---|---|

Using any compounds among Reference Compounds No. 3-4, 8-2, 8-3, 8-5, 12-1 and 13, the following Reference Compounds No. 14-2 to 14-7 were obtained by a method similar to that of Reference Compound No. 14-1.

| 7-(4-Hydroxy-2-methoxyphenyl)-8-(2-methoxy-5-nitrophenoxymethyl)-1,3,3-trimethyl-3,4-dihydro-1H-quinoxalin-2-one (Reference Compound No. 14-2)<br>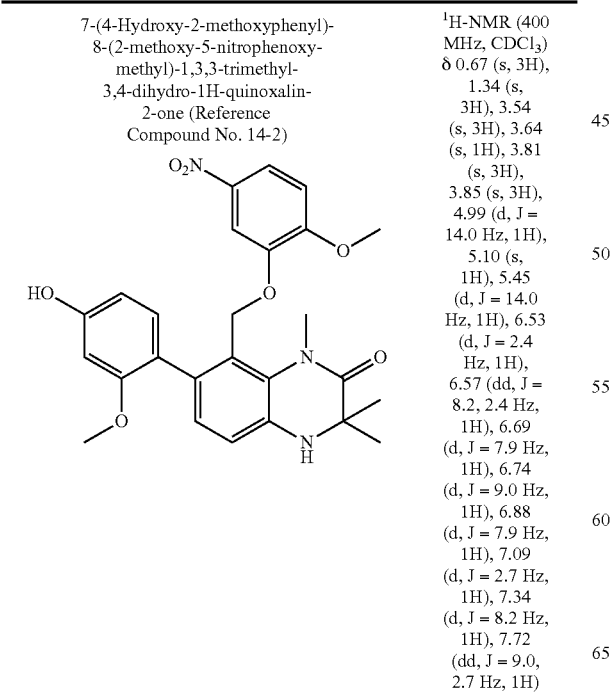 | $^1$H-NMR (400 MHz, CDCl$_3$) δ 0.67 (s, 3H), 1.34 (s, 3H), 3.54 (s, 3H), 3.64 (s, 1H), 3.81 (s, 3H), 3.85 (s, 3H), 4.99 (d, J = 14.0 Hz, 1H), 5.10 (s, 1H), 5.45 (d, J = 14.0 Hz, 1H), 6.53 (d, J = 2.4 Hz, 1H), 6.57 (dd, J = 8.2, 2.4 Hz, 1H), 6.69 (d, J = 7.9 Hz, 1H), 6.74 (d, J = 9.0 Hz, 1H), 6.88 (d, J = 7.9 Hz, 1H), 7.09 (d, J = 2.7 Hz, 1H), 7.34 (d, J = 8.2 Hz, 1H), 7.72 (dd, J = 9.0, 2.7 Hz, 1H) |
|---|---|
| 7-(4-Hydroxy-2-methoxyphenyl)-8-(2-methyl-5-nitrophenoxymethyl)-1,3,3-trimethyl-3,4-dihydro-1H-quinoxalin-2-one (Reference Compound No. 14-3)<br>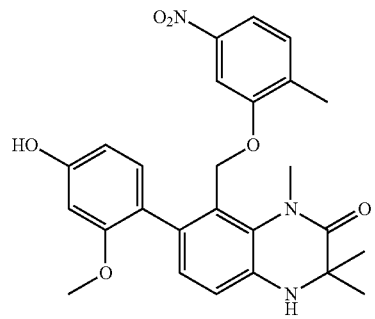 [SMILES: COc1cc(O)ccc1-c1ccc2c(c1COc1cc(F)ccc1C)N(C)C(=O)C(C)(C)N2] | $^1$H-NMR (500 MHz, CDCl$_3$) δ 0.60 (s, 3H), 1.37 (s, 3H), 2.17 (s, 3H), 3.40-3.70 (m, 1H), 3.52 (s, 3H), 3.82 (s, 3H), 4.96 (s, 1H), 4.99 (d, J = 14.1 Hz, 1H), 5.45 (d, J = 14.1 Hz, 1H), 6.53 (d, J = 2.4 Hz, 1H), 6.60 (dd, J = 8.2, 2.4 Hz, 1H), 6.69 (d, J = 8.1 Hz, 1H), 6.90 (d, J = 8.1 Hz, 1H), 7.01 (d, J = 2.1 Hz, 1H), 7.09 (d, J = 8.2 Hz, 1H), 7.40 (d, J = 8.2 Hz, 1H), 7.57 (dd, J = 8.2, 2.1 Hz, 1H) |
| 7-(4-Hydroxy-2-methoxyphenyl)-8-(5-methylthiophen-2-ylcarbonyloxymethyl)-1,3,3-trimethyl-3,4-dihydro-1H-quinoxalin-2-one (Reference Compound No. 14-4)<br>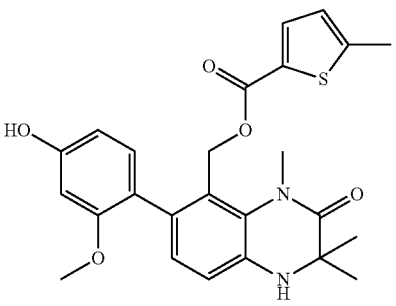 | $^1$H-NMR (400 MHz, CDCl$_3$) δ 1.20 (s, 3H), 1.42 (s, 3H), 2.47 (s, 3H), 3.45 (s, 3H), 3.73 (s, 3H), 3.76 (s, 1H), 5.14 (d, J = 13.3 Hz, 1H), 5.17 (s, 1H), 5.27 (d, J = 13.3 Hz, 1H), 6.42 (dd, J = 8.2, 2.3 Hz, 1H), 6.46 (d, J = 2.3 Hz, 1H), 6.69 (d, J = 3.9 Hz, 1H), 6.74 (d, J = 8.0 Hz, 1H), 6.86 (d, J = 8.0 Hz, 1H), 7.11 (d, J = 8.2 Hz, 1H), 7.45 (d, J = 3.9 Hz, 1H) |

| Compound | NMR |
|---|---|
| 7-(4-Hydroxy-2-methoxyphenyl)-8-(4-methylbenzoyloxymethyl)-1,3,3-trimethyl-3,4-dihydro-1H-quinoxalin-2-one (Reference Compound No. 14-5) 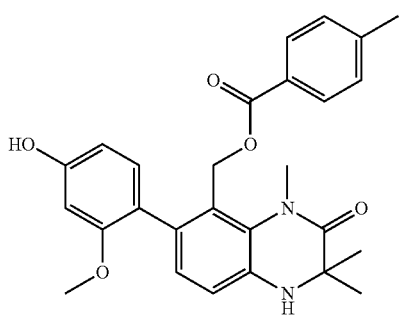 | ¹H-NMR (400 MHz, CDCl₃) δ 1.20 (s, 3H), 1.42 (s, 3H), 2.37 (s, 3H), 3.46 (s, 3H), 3.72 (s, 3H), 3.76 (s, 1H), 4.89 (s, 1H), 5.17 (d, J = 13.4 Hz, 1H), 5.31 (d, J = 13.4 Hz, 1H), 6.40 (dd, J = 8.1, 2.3 Hz, 1H), 6.45 (d, J = 2.3 Hz, 1H), 6.75 (d, J = 8.1 Hz, 1H), 6.87 (d, J = 8.1 Hz, 1H), 7.10 (d, J = 8.1 Hz, 1H), 7.16 (d, J = 8.2 Hz, 2H), 7.74 (d, J = 8.2 Hz, 2H) |
| 8-[N-(9-Fluoroenylmethoxycarbonyl)-N-(2-methoxyphenyl)aminomethyl]-7-(4-hydroxy-2-methoxyphenyl)-1,3,3-trimethyl-3,4-dihydro-1H-quinoxalin-2-one (Reference Compound No. 14-6) 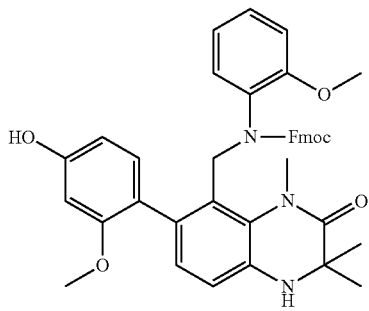 | ¹H-NMR (400 MHz, CDCl₃) δ 1.27 (s, 3H), 1.38 (s, 3H), 3.32 (s, 3H), 3.49-4.15 (m, 10H), 4.39-4.59 (m, 1H), 5.23-5.90 (m, 2H), 6.29-7.33 (m, 15H), 7.62-7.66 (m, 2H) |
| 8-[N-(5-Fluoro-2-methylphenyl)aminomethyl]-7-(4-hydroxy-2-methoxyphenyl)-1,3,3-trimethyl-3,4-dihydro-1H-quinoxalin-2-one (Reference Compound No. 14-7) 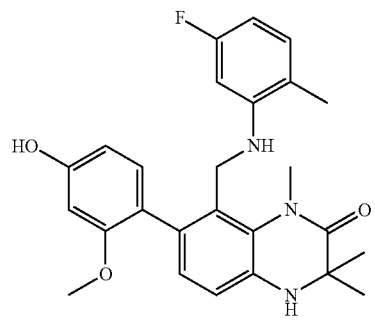 | ¹H-NMR (500 MHz, CDCl₃) δ 1.16 (s, 3H), 1.40 (s, 3H), 1.86 (s, 3H), 3.43 (s, 3H), 3.73 (s, 3H), 3.76 (s, 1H), 3.82-3.85 (m, 1H), 4.13 (dd, J = 13.9, 5.5 Hz, 1H), 4.20 (dd, J = 13.9, 5.0 Hz, 1H), 5.01 (s, 1H), 6.02 (dd, J = 11.8, 2.6 Hz, 1H), 6.22 (td, J = 8.3, 2.6 Hz, 1H), 6.47 (dd, J = 8.0, 2.4 Hz, 1H), 6.49 (d, J = 2.4 Hz, 1H), 6.70 (d, J = 7.9 Hz, 1H), 6.81-6.85 (m, 1H), 6.82 (d, J = 7.9 Hz, 1H), 7.05 (d, J = 8.0 Hz, 1H) |

EXAMPLES

Example 1

8-(5-Fluoro-2-methylphenoxymethyl)-7-(2-methoxy-4-methylsulfonyloxyphenyl)-1,3,3-trimethyl-3,4-dihydro-1H-quinoxalin-2-one (Compound No. 1-1)

8-(5-Fluoro-2-methylphenoxymethyl)-7-(4-hydroxy-2-methoxyphenyl)-1,3,3-trimethyl-3,4-dihydro-1H-quinoxalin-2-one (Reference Compound No. 14-1, 61.1 mg, 0.136 mmol) was dissolved in anhydrous dichloromethane (1 mL), and triethylamine (44 μL, 0.319 mmol) and methanesulfonyl chloride (13 μL, 0.168 mmol) were added thereto successively. The reaction mixture was stirred at room temperature for hours and 15 minutes. The reaction mixture was purified by silica gel column chromatography (hexane-ethyl acetate) to give the titled compound (68.3 mg) as a colorless amorphous product. (Yield 98%)

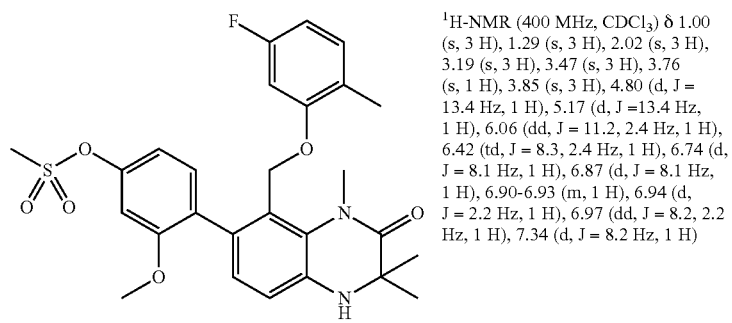

¹H-NMR (400 MHz, CDCl₃) δ 1.00 (s, 3 H), 1.29 (s, 3 H), 2.02 (s, 3 H), 3.19 (s, 3 H), 3.47 (s, 3 H), 3.76 (s, 1 H), 3.85 (s, 3 H), 4.80 (d, J = 13.4 Hz, 1 H), 5.17 (d, J =13.4 Hz, 1 H), 6.06 (dd, J = 11.2, 2.4 Hz, 1 H), 6.42 (td, J = 8.3, 2.4 Hz, 1 H), 6.74 (d, J = 8.1 Hz, 1 H), 6.87 (d, J = 8.1 Hz, 1 H), 6.90-6.93 (m, 1 H), 6.94 (d, J = 2.2 Hz, 1 H), 6.97 (dd, J = 8.2, 2.2 Hz, 1 H), 7.34 (d, J = 8.2 Hz, 1 H)

Using any compounds among Reference Compounds No. 14-1 to 14-5, 14-7 and commercially available compounds, the following Compounds No. 1-2 to 1-44 were obtained by a method similar to that of Compound No. 1-1.

| | |
|---|---|
| 8-(5-Fluoro-2-methylphenoxymethyl)-7-(2-methoxy-4-propyl-sulfonyloxyphenyl)-1,3,3-trimethyl-3,4-dihydro-1H-quinoxalin-2-one (Compound No. 1-2)<br>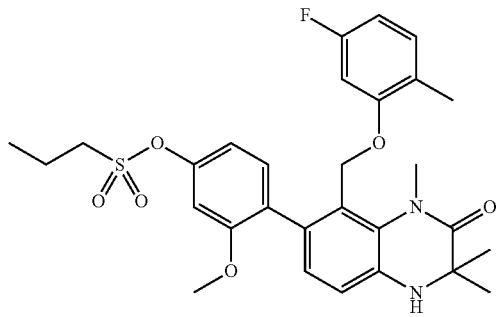 [SMILES: CCCS(=O)(=O)Oc1ccc(-c2ccc3c(c2COc2cc(F)ccc2C)N(C)C(=O)C(C)(C)N3)c(OC)c1] | $^1$H-NMR (400 MHz, CDCl$_3$) δ 0.97 (s, 3 H), 1.15 (t, J = 7.5 Hz, 3 H), 1.27 (s, 3 H), 2.01 (s, 3 H), 2.02-2.09 (m, 2 H), 3.25-3.29 (m, 2 H), 3.46 (s, 3 H), 3.75 (s, 1 H), 3.84 (s, 3 H), 4.80 (d, J = 13.4 Hz, 1 H), 5.17 (d, J = 13.4 Hz, 1 H), 6.05 (dd, J = 11.1, 2.4 Hz, 1 H), 6.40 (td, J = 8.3, 2.4 Hz, 1 H), 6.73 (d, J = 8.1 Hz, 1 H), 6.86 (d, J = 8.1 Hz, 1 H), 6.89-6.93 (m, 2 H), 6.95 (d, J = 2.2 Hz, 1 H), 7.32 (d, J = 8.3 Hz, 1 H) |
| 7-(2-Methoxy-4-methylsulfonyloxyphenyl)-8-(5-methylthiophen-2-ylcarbonyloxymethyl)-1,3,3-trimethyl-3,4-dihydro-1H-quinoxalin-2-one (Compound No. 1-3)<br>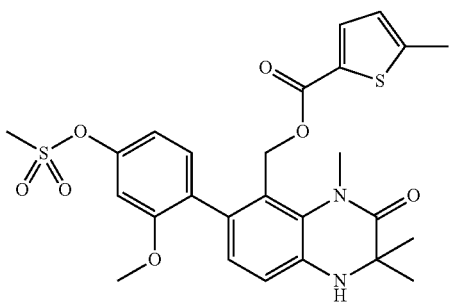 | $^1$H-NMR (400 MHz, CDCl$_3$) δ 1.23 (s, 3 H), 1.41 (s, 3 H), 2.48 (s, 3 H), 3.16 (s, 3 H), 3.46 (s, 3 H), 3.75 (s, 3 H), 3.81 (s, 1 H), 5.08 (d, J = 13.3 Hz, 1 H), 5.23 (d, J = 13.3 Hz, 1 H), 6.70 (d, J = 3.8 Hz, 1 H), 6.76 (d, J = 8.1 Hz, 1 H), 6.84 (d, J = 8.1 Hz, 1 H), 6.87 (s, 1 H), 6.87-6.89 (m, 1 H), 7.26-7.29 (m, 1 H), 7.42 (d, J = 3.8 Hz, 1 H) |
| 7-(4-Benzylsulfonyloxy-2-methoxyphenyl)-8-(5-fluoro-2-methyl-phenoxymethyl)-1,3,3-trimethyl-3,4-dihydro-1H-quinoxalin-2-one (Compound No. 1-4)<br>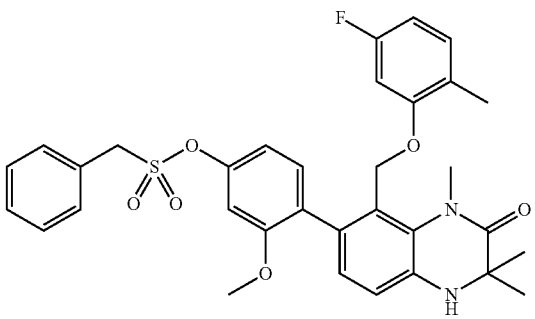 | $^1$H-NMR (500 MHz, CDCl$_3$) δ 0.97 (s, 3 H), 1.26 (s, 3 H), 2.01 (s, 3 H), 3.45 (s, 3 H), 3.73 (s, 1 H), 3.74 (s, 3 H), 4.56 (s, 2 H), 4.78 (d, J = 13.4 Hz, 1 H), 5.14 (d, J = 13.4 Hz, 1 H), 6.04 (dd, J = 11.3, 2.4 Hz, 1 H), 6.40 (td, J = 8.2, 2.4 Hz, 1 H), 6.67 (d, J = 2.2 Hz, 1 H), 6.71 (d, J = 7.9 Hz, 1 H), 6.80 (dd, J = 8.3, 2.2 Hz, 1 H), 6.83 (d, J = 7.9 Hz, 1 H), 6.89-6.92 (m, 1 H), 7.27 (d, J = 8.3 Hz, 1 H), 7.42-7.45 (m, 3 H), 7.47-7.50 (m, 2 H) |
| 7-(4-Butylsulfonyloxy-2-methoxyphenyl)-8-(5-fluoro-2-methyl-phenoxymethyl)-1,3,3-trimethyl-3,4-dihydro-1H-quinoxalin-2-one (Compound No. 1-5)<br>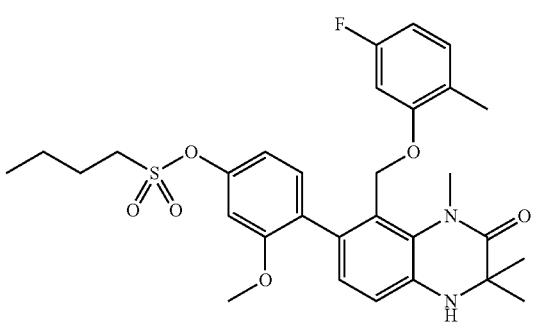 [SMILES: CCCCS(=O)(=O)Oc1ccc(-c2ccc3c(c2COc2cc(F)ccc2C)N(C)C(=O)C(C)(C)N3)c(OC)c1] | $^1$H-NMR (500 MHz, CDCl$_3$) δ 0.97 (s, 3 H), 1.00 (t, J = 7.3 Hz, 3 H), 1.27 (s, 3 H), 1.50-1.59 (m, 2 H), 1.96-2.03 (m, 2 H), 2.01 (s, 3 H), 3.27-3.34 (m, 2 H), 3.46 (s, 3 H), 3.74 (s, 1 H), 3.83 (s, 3 H), 4.80 (d, J = 13.3 Hz, 1 H), 5.17 (d, J = 13.3 Hz, 1 H), 6.05 (dd, J = 11.0, 2.4 Hz, 1 H), 6.40 (td, J = 8.3, 2.4 Hz, 1 H), 6.73 (d, J = 7.9 Hz, 1 H), 6.86 (d, J = 7.9 Hz, 1 H), 6.89-6.92 (m, 2 H), 6.94 (dd, J = 8.2, 2.3 Hz, 1 H), 7.32 (d, J = 8.2 Hz, 1 H) |

7-(4-Ethylsulfonyloxy-2-methoxyphenyl)-8-(5-fluoro-2-methyl-phenoxymethyl)-1,3,3-trimethyl-3,4-dihydro-1H-quinoxalin-2-one (Compound No. 1-6)

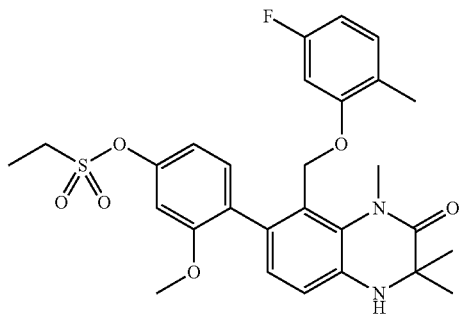 [SMILES: CCS(=O)(=O)Oc1ccc(-c2ccc3c(c2COc2cc(F)ccc2C)N(C)C(=O)C(C)(C)N3)c(OC)c1]

$^1$H-NMR (400 MHz, CDCl$_3$) δ 0.98 (s, 3 H), 1.28 (s, 3 H), 1.57 (t, J = 7.4 Hz, 3 H), 2.01 (s, 3 H), 3.32 (q, J = 7.4 Hz, 2 H), 3.46 (s, 3 H), 3.75 (s, 1 H), 3.84 (s, 3 H), 4.80 (d, J = 13.4 Hz, 1 H), 5.17 (d, J = 13.4 Hz, 1 H), 6.05 (dd, J = 11.5, 2.4 Hz, 1 H), 6.41 (td, J = 8.3, 2.4 Hz, 1 H), 6.73 (d, J = 8.1 Hz, 1 H), 6.86 (d, J = 8.1 Hz, 1 H), 6.89-6.94 (m, 1 H), 6.93 (d, J = 2.3 Hz, 1 H), 6.95 (dd, J = 8.1, 2.3 Hz, 1 H), 7.32 (d, J = 8.1 Hz, 1 H)

8-(5-Fluoro-2-methylphenoxymethyl)-7-(4-isopropylsulfonyloxy-2-methoxyphenyl)-1,3,3-trimethyl-3,4-dihydro-1H-quinoxalin-2-one (Compound No. 1-7)

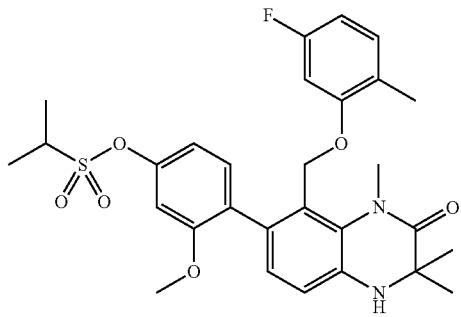 [SMILES: COc1cc(OS(=O)(=O)C(C)C)ccc1-c1ccc2c(c1COc1cc(F)ccc1C)N(C)C(=O)C(C)(C)N2]

$^1$H-NMR (400 MHz, CDCl$_3$) δ 0.97 (s, 3 H), 1.28 (s, 3 H), 1.59 (d, J = 6.9 Hz, 6 H), 2.01 (s, 3 H), 3.46 (s, 3 H), 3.50 (septet, J = 6.9 Hz, 1 H), 3.74 (s, 1 H), 3.84 (s, 3 H), 4.80 (d, J = 13.4 Hz, 1 H), 5.17 (d, J = 13.4 Hz, 1 H), 6.05 (dd, J = 11.2, 2.4 Hz, 1 H), 6.40 (td, J = 8.3, 2.4 Hz, 1 H), 6.73 (d, J = 8.0 Hz, 1 H), 6.89 (d, J = 8.0 Hz, 1 H), 6.89-6.93 (m, 1 H), 6.92 (d, J = 2.3 Hz, 1 H), 6.95 (dd, J = 8.3, 2.3 Hz, 1 H), 7.32 (d, J = 8.3 Hz, 1 H)

7-[4-(3-Chlorobenzylsulfonyloxy)-2-methoxyphenyl]-8-(5-fluoro-2-methylphenoxymethyl)-1,3,3-trimethyl-3,4-dihydro-1H-quinoxalin-2-one (Compound No. 1-8)

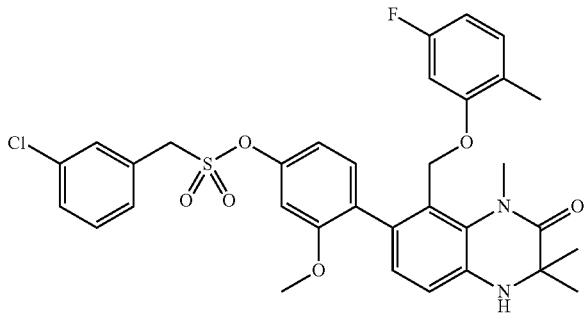 [SMILES: COc1cc(OS(=O)(=O)Cc2cccc(Cl)c2)ccc1-c1ccc2c(c1COc1cc(F)ccc1C)N(C)C(=O)C(C)(C)N2]

$^1$H-NMR (400 MHz, CDCl$_3$) δ 0.98 (s, 3 H), 1.27 (s, 3 H), 2.01 (s, 3 H), 3.45 (s, 3 H), 3.75 (s, 1 H), 3.78 (s, 3 H), 4.51 (s, 2 H), 4.78 (d, J = 13.4 Hz, 1 H), 5.15 (d, J = 13.4 Hz, 1 H), 6.04 (dd, J = 11.2, 2.4 Hz, 1 H), 6.40 (td, J = 8.3, 2.4 Hz, 1 H), 6.72 (d, J = 7.9 Hz, 1 H), 6.72 (d, J = 2.3 Hz, 1 H), 6.84 (d, J = 7.9 Hz, 1 H), 6.84 (dd, J = 8.2, 2.3 Hz, 1 H), 6.89-6.93 (m, 1 H), 7.29 td, J = 8.2 Hz, 1 H), 7.36-7.43 (m, 3 H), 7.48 (s, 1 H)

8-(5-Fluoro-2-methylphenoxymethyl)-7-[2-methoxy-4-(4-methylbenzyl-sulfonyloxy)phenyl]-1,3,3-trimethyl-3,4-dihydro-1H-quinoxalin-2-one (Compound No. 1-9)

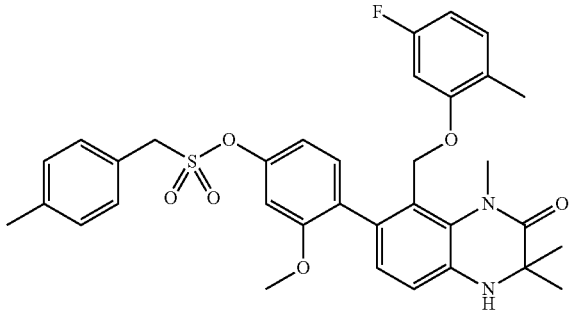

$^1$H-NMR (400 MHz, CDCl$_3$) δ 0.96 (s, 3 H), 1.26 (s, 3 H), 2.01 (s, 3 H), 2.38 (s, 3 H), 3.45 (s, 3 H), 3.75 (s, 4 H), 4.52 (s, 2 H), 4.78 (d, J = 13.3 Hz, 1 H), 5.15 (d, J = 13.3 Hz, 1 H), 6.04 (dd, J = 11.2, 2.4 Hz, 1 H), 6.40 (td, J = 8.3, 2.4 Hz, 1 H), 6.67 (d, J = 2.4 Hz, 1 H), 6.71 (d, J = 8.1 Hz, 1 H), 6.82 (dd, J = 8.1, 2.4 Hz, 1 H), 6.83 (d, J = 8.1 Hz, 1 H), 6.88-6.92 (m, 1 H), 7.24 (d, J = 8.0 Hz, 2 H), 7.27 (d, J = 8.1 Hz, 1 H), 7.37 (d, J = 8.0 Hz, 2 H)

| Compound | NMR |
|---|---|
| 7-[4-(4-Chlorobenzylsulfonyloxy)-2-methoxyphenyl]-8-(5-fluoro-2-methylphenoxymethyl)-1,3,3-trimethyl-3,4-dihydro-1H-quinoxalin-2-one (Compound No. 1-10)<br>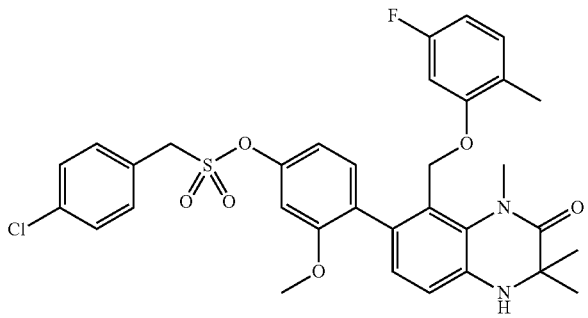 [SMILES: COc1cc(OS(=O)(=O)Cc2ccc(Cl)cc2)ccc1-c1ccc2c(c1COc1cc(F)ccc1C)N(C)C(=O)C(C)(C)N2] | 1H-NMR (500 MHz, CDCl$_3$) δ 0.98 (s, 3 H), 1.27 (s, 3 H), 2.01 (s, 3 H), 3.45 (s, 3 H), 3.74 (s, 1 H), 3.77 (s, 3 H), 4.51 (s, 2 H), 4.77 (d, J = 13.3 Hz, 1 H), 5.14 (d, J = 13.3 Hz, 1 H), 6.04 (dd, J = 11.3, 2.4 Hz, 1 H), 6.40 (td, J = 8.2, 2.4 Hz, 1 H), 6.68 (d, J = 2.4 Hz, 1 H), 6.72 (d, J = 8.1 Hz, 1 H), 6.82 (dd, J = 8.3, 2.4 Hz, 1 H), 6.84 (d, J = 8.1 Hz, 1 H), 6.89-6.92 (m, 1 H), 7.29 (d, J = 8.3 Hz, 1 H), 7.42 (s, 4 H) |
| 8-(5-Fluoro-2-methylphenoxymethyl)-7-(4-isobutylsulfonyloxy-2-methoxyphenyl)-1,3,3-trimethyl-3,4-dihydro-1H-quinoxalin-2-one (Compound No. 1-11)<br>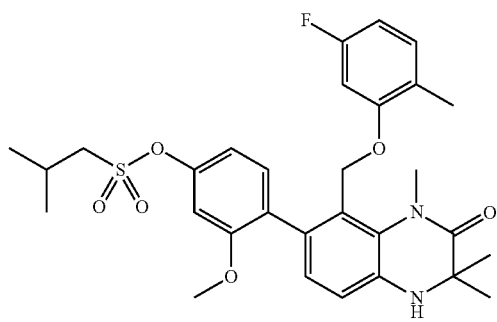 | $^1$H-NMR (400 MHz, CDCl$_3$) δ 0.97 (s, 3 H), 1.19 (d, J = 6.6 Hz, 6 H), 1.28 (s, 3 H), 2.01 (s, 3 H), 2.43-2.50 (m, 1 H), 3.20 (d, J = 6.6 Hz, 2 H), 3.46 (s, 3 H), 3.75 (s, 1 H), 3.84 (s, 3 H), 4.80 (d, J = 13.4 Hz, 1 H), 5.17 (d, J = 13.4 Hz, 1 H), 6.05 (dd, J = 11.2, 2.4 Hz, 1 H), 6.40 (td, J = 8.3, 2.4 Hz, 1 H), 6.73 (d, J = 8.0 Hz, 1 H), 6.86 (d, J = 8.0 Hz, 1 H), 6.89-6.92 (m, 1 H), 6.92 (d, J = 2.3 Hz, 1 H), 6.94 (dd, J = 8.3, 2.3 Hz, 1 H), 7.32 (d, J = 8.3 Hz, 1 H) |
| 8-(5-Fluoro-2-methylphenoxymethyl)-7-[2-methoxy-4-(3,3,3-trifluoropropylsulfonyloxy)phenyl]-1,3,3-trimethyl-3,4-dihydro-1H-quinoxlin-2-one (Compound No. 1-12)<br>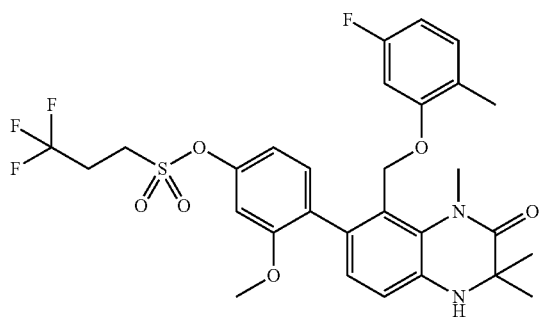 | $^1$H-NMR (400 MHz, CDCl$_3$) δ 1.00 (s, 3 H), 1.28 (s, 3 H), 2.01 (s, 3 H), 2.79-2.90 (m, 2 H), 3.46 (s, 3 H), 3.50-3.54 (m, 2 H), 3.76 (s, 1 H), 3.84 (s, 3 H), 4.79 (d, J = 13.4 Hz, 1 H), 5.16 (d, J = 13.4 Hz, 1 H), 6.05 (dd, J = 11.2, 2.5 Hz, 1 H), 6.41 (td, J = 8.3, 2.5 Hz, 1 H), 6.73 (d, J = 8.1 Hz, 1 H), 6.86 (d, J = 8.1 Hz, 1 H), 6.89 (d, J = 2.4 Hz, 1 H), 6.89-6.93 (m, 1 H), 6.93 (dd, J = 8.2, 2.4 Hz, 1 H), 7.35 (d, J = 8.2 Hz, 1 H) |
| 7-(4-Cyclopropylsulfonyloxy-2-methoxyphenyl)-8-(5-fluoro-2-methylphenoxymethyl)-1,3,3-trimethyl-3,4-dihydro-1H-quinoxalin-2-one (Compound No. 1-13)<br>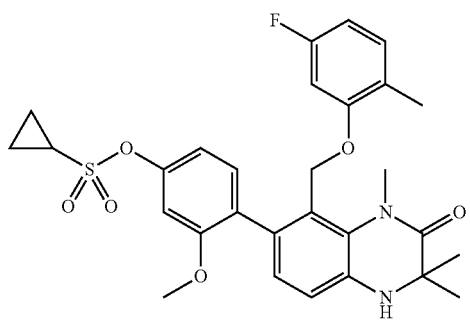 [SMILES: COc1cc(OS(=O)(=O)C2CC2)ccc1-c1ccc2c(c1COc1cc(F)ccc1C)N(C)C(=O)C(C)(C)N2] | $^1$H-NMR (400 MHz, CDCl$_3$) δ 0.99 (s, 3 H), 1.10-1.13 (m, 2 H), 1.28 (s, 3 H), 1.28-1.32 (m, 2 H), 2.02 (s, 3 H), 2.60 (tt, J = 7.9, 4.7 Hz, 1 H), 3.46 (s, 3 H), 3.75 (s, 1 H), 3.83 (s, 3 H), 4.77 (d, J = 13.3 Hz, 1 H), 5.15 (d, J = 13.3 Hz, 1 H), 6.05 (dd, J = 11.2, 2.5 Hz, 1 H), 6.40 (td, J = 8.3, 2.5 Hz, 1 H), 6.73 (d, J = 8.0 Hz, 1 H), 6.87 (d, J = 8.0 Hz, 1 H), 6.89-6.93 (m, 1 H), 6.94 (d, J = 2.4 Hz, 1 H), 6.99 (dd, J = 8.3, 2.4 Hz, 1 H), 7.32 (d, J = 8.3 Hz, 1 H) |

| | |
|---|---|
| 7-[4-(2-Chlorobenzylsulfonyloxy)-2-methoxyphenyl]-8-(5-fluoro-2-methylphenoxymethyl)-1,3,3-trimethyl-3,4-dihydro-1H-quinoxalin-2-one (Compound No. 1-14)<br>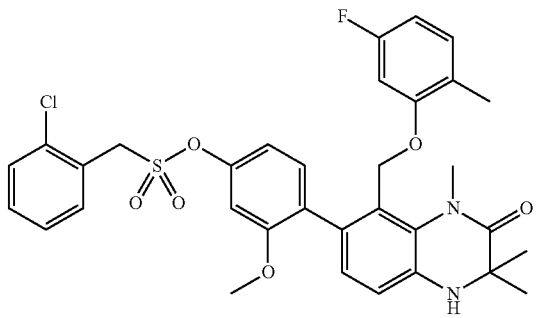 [SMILES: COc1cc(OS(=O)(=O)Cc2ccccc2Cl)ccc1-c1ccc2c(c1COc1cc(F)ccc1C)N(C)C(=O)C(C)(C)N2] | ¹H-NMR (500 MHz, CDCl₃) δ 0.96 (s, 3 H), 1.26 (s, 3 H), 2.01 (s, 3 H), 3.45 (s, 3 H), 3.73 (s, 1 H), 3.77 (s, 3 H), 4.77 (d, J = 13.4 Hz, 1 H), 4.82 (s, 2 H), 5.15 (d, J = 13.4 Hz, 1 H), 6.03 (dd, J = 11.3, 2.4 Hz, 1 H), 6.39 (td, J = 8.2, 2.4 Hz, 1 H), 6.71 (d, J = 8.1 Hz, 1 H), 6.76 (d, J = 2.3 Hz, 1 H), 6.83 (d, J = 8.1 Hz, 1 H), 6.84 (dd, J = 7.6, 2.3 Hz, 1 H), 6.89-6.92 (m, 1 H), 7.29 (d, J = 7.6 Hz, 1 H), 7.33-7.38 (m, 2 H), 7.48 (dd, J = 7.5, 1.7 Hz, 1 H), 7.63 (dd, J = 7.2, 2.3 Hz, 1H ) |
| 8-(5-Fluoro-2-methylphenoxymethyl)-7-[2-methoxy-4-(2-methylbenzyl-sulfonyloxy)phenyl]-1,3,3-trimethyl-3,4-dihydro-1H-quinoxalin-2-one (Compound No. 1-15)<br>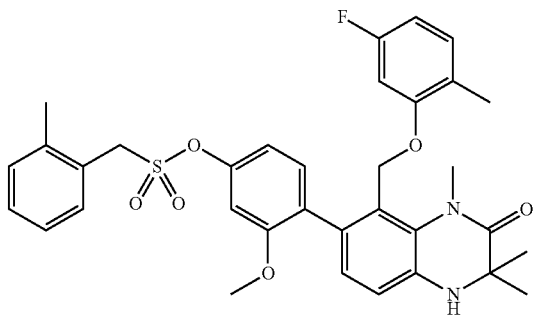 [SMILES: COc1cc(OS(=O)(=O)Cc2ccccc2C)ccc1-c1ccc2c(c1COc1cc(F)ccc1C)N(C)C(=O)C(C)(C)N2] | ¹H-NMR (500 MHz, CDCl₃) δ 0.96 (s, 3 H), 1.26 (s, 3 H), 2.00 (s, 3 H), 2.47 (s, 3 H), 3.44 (s, 3 H), 3.73 (s, 4 H), 4.64 (s, 2 H), 4.77 (d, J = 13.4 Hz, 1 H), 5.14 (d, J = 13.4 Hz, 1 H), 6.03 (dd, J = 11.0, 2.4 Hz, 1 H), 6.40 (td, J = 8.2, 2.4 Hz, 1 H), 6.64 (d, J = 2.1 Hz, 1 H), 6.71 (d, J = 7.9 Hz, 1 H), 6.79 (dd, J = 8.2, 2.1 Hz, 1 H), 6.83 (d, J = 7.9 Hz, 1 H), 6.89-6.92 (m, 1 H), 7.26-7.-3,4 (m, 4 H), 7.45 (d, J = 7.6 Hz, 1 H) |
| 7-(4-Cyclopentylsulfonyloxy-2-methoxyphenyl)-8-(5-fluoro-2-methylphenoxymethyl)-1,3,3-trimethly-3,4-dihydro-1H-quinoxalin-2-one (Compound No. 1-16)<br>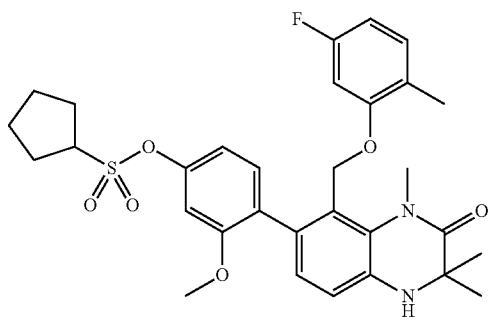 [SMILES: COc1cc(OS(=O)(=O)C2CCCC2)ccc1-c1ccc2c(c1COc1cc(F)ccc1C)N(C)C(=O)C(C)(C)N2] | ¹H-NMR (400 MHz, CDCl₃) δ 0.97 (s, 3 H), 1.27 (s, 3 H), 1.69-1.76 (m, 2 H), 1.88-1.94 (m, 2 H), 2.01 (s, 3 H), 2.11-2.20 (m, 2 H), 2.24-2.29 (m, 2 H), 3.46 (s, 3 H), 3.68-3.76 (m, 1 H), 3.74 (s, 1 H), 3.83 (s, 3 H), 4.80 (d, J = 13.4 Hz, 1 H), 5.17 (d, J = 13.4 Hz, 1 H), 6.05 (dd, J = 11.2, 2.5 Hz, 1 H), 6.40 (td, J = 8.4, 2.5 Hz, 1 H), 6.72 (d, J = 8.1 Hz, 1 H), 6.86 (d, J = 8.1 Hz, 1 H), 6.89-6.93 (m, 1 H), 6.93 (d, J = 2.2 Hz, 1 H), 6.94 (dd, J = 8.1, 2.2 Hz, 1 H), 7.31(d, J = 8.1 Hz, 1 H) |
| 7-(4-Cyclohexylsulfonyloxy-2-methoxyphenyl)-8-(5-fluoro-2-methylphenoxymethyl)-1,3,3-trimethyl-3,4-dihydro-1H-quinoxalin-2-one (Compound No. 1-17)<br>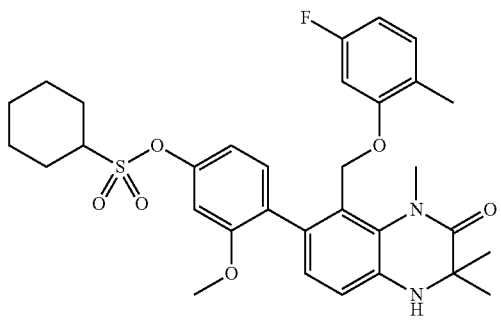 [SMILES: COc1cc(OS(=O)(=O)C2CCCCC2)ccc1-c1ccc2c(c1COc1cc(F)ccc1C)N(C)C(=O)C(C)(C)N2] | ¹H-NMR (500 MHz, CDCl₃) δ 0.97 (s, 3 H), 1.27 (s, 3 H), 1.29-1.39 (m, 3 H), 1.72-1.80 (m, 3 H), 1.96-1.99 (m, 2 H), 2.01 (s, 3 H), 2.37-2.39 (m, 2 H), 3.25 (tt, J = 12.1, 3.5 Hz, 1 H), 3.46 (s, 3 H), 3.74 (s, 1 H), 3.83 (s, 3 H), 4.81 (d, J = 13.4 Hz, 1 H), 5.17 (d, J = 13.4 Hz, 1 H), 6.05 (dd, J = 11.2, 2.4 Hz, 1 H), 6.40 (td, J = 8.2, 2.4 Hz, 1 H), 6.72 (d, J = 7.9 Hz, 1 H), 6.86 (d, J = 7.9 Hz, 1 H), 6.89-6.92 (m, 1 H), 6.91 (d, J =2.4 Hz, 1 H), 6.93 (dd, J = 8.1, 2.4 Hz, 1 H), 7.31 (d, J = 8.1 Hz, 1 H) |

8-(5-Fluoro-2-methylphenoxymethyl)-7-[2-methoxy-4-(3-methylbenzyl-sulfonyloxy)phenyl]-1,3,3-trimethyl-3,4-dihydro-1H-quinoxalin-2-one
(Compound No. 1-18)

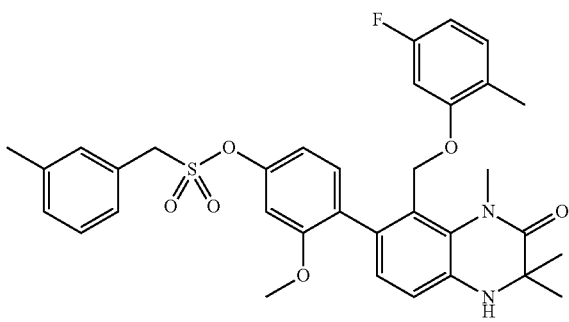

$^1$H-NMR (400 MHz, CDCl$_3$)
δ 0.96 (s, 3 H), 1.26 (s, 3 H), 2.01 (s, 3 H), 2.38 (s, 3 H), 3.45 (s, 3 H), 3.74 (s, 1 H), 3.75 (s, 3 H), 4.52 (s, 2 H), 4.78 (d, J = 13.6 Hz, 1 H), 5.15 (d, J = 13.6 Hz, 1 H), 6.04 (dd, J = 11.2, 2.4 Hz, 1 H), 6.39 (td, J = 8.3, 2.4 Hz, 1 H), 6.69 (d, J = 2.2 Hz, 1 H), 6.71 (d, J = 8.0 Hz, 1 H), 6.82 (dd, J = 8.3, 2.2 Hz, 1 H), 6.84 (d, J = 8.0 Hz, 1 H), 6.88-6.92 (m, 1 H), 7.22-7.34 (m, 4 H), 7.28 (d, J = 8.3 Hz, 1 H)

7-(4-Cyclopropylsulfonyloxy-2-methoxyphenyl)-8-(5-methyl-thiophen-2-ylcarbonyloxymethyl)-1,3,3-trimethyl-3,4-dihydro-1H-quinoxalin-2-one
(Compound No. 1-19)

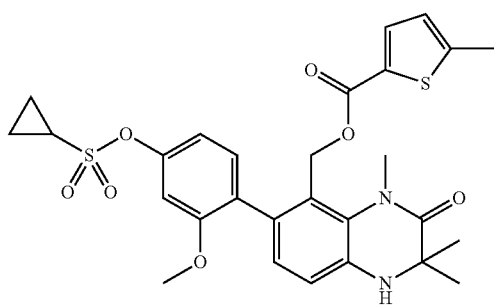 [SMILES: COc1cc(OS(=O)(=O)C2CC2)ccc1-c1ccc2c(c1COC(=O)c1ccc(C)s1)N(C)C(=O)C(C)(C)N2]

$^1$H-NMR (400 MHz, CDCl$_3$)
δ 1.09-1.15 (m, 2 H), 1.23 (s, 3 H), 1.28-1.33 (m, 2 H), 1.41 (s, 3 H), 2.48 (s, 3 H), 2.60 (tt, J = 7.9, 4.8 Hz, 1 H), 3.46 (s, 3 H), 3.75 (s, 3 H), 3.81 (s, 1 H), 5.07 (d, J = 13.2 Hz, 1 H), 5.23 (d, J = 13.2 Hz, 1 H), 6.70 (d, J = 3.6 Hz, 1 H), 6.76 (d, J = 8.1 Hz, 1 H), 6.84 (d, J = 8.1 Hz, 1 H), 6.89 (d, J = 2.3 Hz, 1 H), 6.91 (dd, J = 7.7, 2.3 Hz, 1 H), 7.27 (d, J = 7.7 Hz, 1 H), 7.43 (d, J = 3.6 Hz, 1 H)

7-[2-Methoxy-4-(3,3,3-trifluoropropylsulfonyloxy)phenyl]-8-(5-methylthiophen-2-ylcarbonyloxymethyl)-1,3,3-trimethyl-3,4-dihydro-1H-quinoxalin-2-one
(Compound No. 1-20)

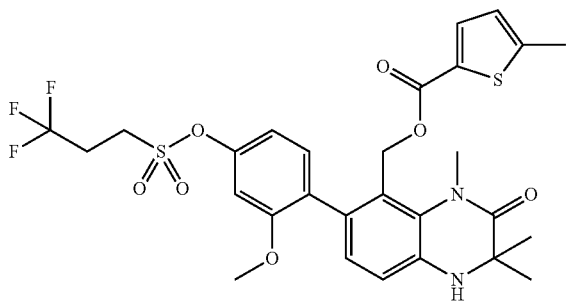 [SMILES: COc1cc(OS(=O)(=O)CCC(F)(F)F)ccc1-c1ccc2c(c1COC(=O)c1ccc(C)s1)N(C)C(=O)C(C)(C)N2]

$^1$H-NMR (400 MHz, CDCl$_3$)
δ 1.23 (s, 3 H), 1.41 (s, 3 H), 2.48 (s, 3 H), 2.77-2.89 (m, 2 H), 3.46 (s, 3 H), 3.49-3.53 (m, 2 H), 3.76 (s, 3 H), 3.82 (s, 1 H), 5.07 (d, J = 13.2 Hz, 1 H), 5.24 (d, J = 13.2 Hz, 1 H), 6.70 (d, J = 3.7 Hz, 1 H), 6.76 (d, J = 8.1 Hz, 1 H), 6.83 (d, J = 2.4 Hz, 1 H), 6.84 (d, J = 8.1 Hz, 1 H), 6.85 (dd, J = 8.3, 2.4 Hz, 1 H), 7.30 (d, J = 8.3 Hz, 1 H), 7.43 (d, J = 3.7 Hz, 1 H)

7-(4-Isobutylsulfonyloxy-2-methoxyphenyl)-8-(5-methylthiophen-2-ylcarbonyloxymethyl)-1,3,3-trimethyl-3,4-dihydro-1H-quinoxalin-2-one
(Compound No. 1-21)

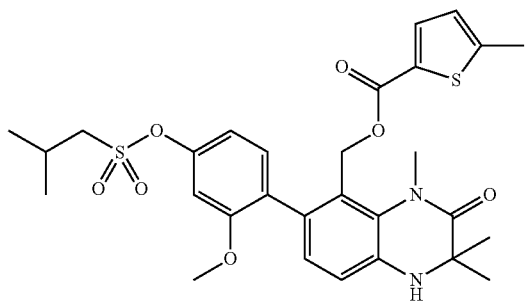 [SMILES: COc1cc(OS(=O)(=O)CC(C)C)ccc1-c1ccc2c(c1COC(=O)c1ccc(C)s1)N(C)C(=O)C(C)(C)N2]

$^1$H-NMR (500 MHz, CDCl$_3$)
δ 1.18 (d, J = 6.8 Hz, 3 H), 1.19 (d, J = 6.8 Hz, 3 H), 1.22 (s, 3 H), 1.41 (s, 3 H), 2.41-2.51 (m, 1 H), 2.48 (s, 3 H), 3.18 (d, J = 6.7 Hz, 2 H), 3.46 (s, 3 H), 3.75 (s, 3 H), 3.81 (s, 1 H), 5.08 (d, J = 13.1 Hz, 1 H), 5.25 (d, J = 13.1 Hz, 1 H), 6.70 (d, J = 3.7 Hz, 1 H), 6.76 (d, J = 7.9 Hz, 1 H), 6.84 (d, J = 7.9 Hz, 1 H), 6.86 (s, 1 H), 6.87 (d, J = 7.9 Hz, 1 H), 7.28 (d, J = 7.9 Hz, 1 H), 7.43 (d, J = 3.7 Hz, 1 H)

| | |
|---|---|
| 7-(2-Methoxy-4-propylsulfonyloxyphenyl)-8-(5-methylthiophen-2-ylcarbonyloxymethyl)-1,3,3-trimethyl-3,4-dihydro-1H-quinoxalin-2-one (Compound No. 1-22)<br />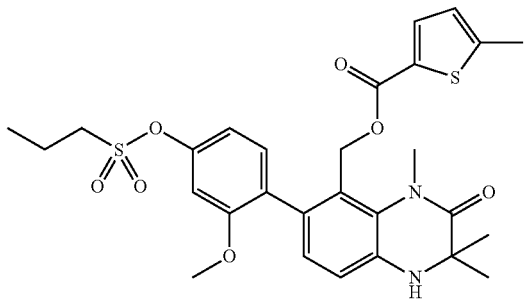 [SMILES: CCCS(=O)(=O)Oc1ccc(-c2ccc3c(c2COC(=O)c2ccc(C)s2)N(C)C(=O)C(C)(C)N3)c(OC)c1] | $^1$H-NMR (400 MHz, CDCl$_3$) δ 1.14 (t, J = 7.6 Hz, 3 H), 1.22 (s, 3 H), 1.41 (s, 3 H), 1.99-2.08 (m, 2 H), 2.48 (s, 3 H), 3.23-3.27 (m, 2 H), 3.46 (s, 3 H), 3.76 (s, 3 H), 3.81 (s, 1 H), 5.08 (d, J = 13.2 Hz, 1 H), 5.25 (d, J = 13.2 Hz, 1 H), 6.70 (d, J = 3.8 Hz, 1 H), 6.76 (d, J = 8.1 Hz, 1 H), 6.84 (d, J = 8.1 Hz, 1 H), 6.86 (d, J = 1.7 Hz, 1 H), 6.87 (dd, J = 7.3, 1.7 Hz, 1 H), 7.28 (d, J = 7.3 Hz, 1 H), 7.43 (d, J = 3.8 Hz, 1 H) |
| 7-(4-Isopropylsulfonyloxy-2-methoxyphenyl)-8-(5-methylthiophen-2-ylcarbonyloxymethyl)-1,3,3-trimethyl-3,4-dihydro-1H-quinoxalin-2-one (Compound No. 1-23)<br />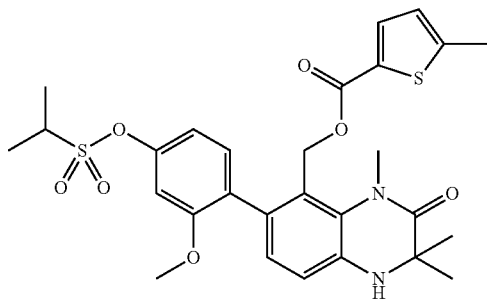 [SMILES: COc1cc(OS(=O)(=O)C(C)C)ccc1-c1ccc2c(c1COC(=O)c1ccc(C)s1)N(C)C(=O)C(C)(C)N2] | $^1$H-NMR (500 MHz, CDCl$_3$) δ 1.21 (s, 3 H), 1.41 (s, 3 H), 1.56 (d, J = 7.3 Hz, 3 H), 1.57 (d, J = 7.3 Hz, 3 H), 2.48 (s, 3 H), 3.45 (s, 3 H), 3.47-3.52 (m, 1 H), 3.76 (s, 3 H), 3.80 (s, 1 H), 5.08 (d, J = 13.1 Hz, 1 H), 5.25 (d, J = 13.1 Hz, 1 H), 6.70 (d, J = 3.9 Hz, 1 H), 6.76 (d, J = 7.9 Hz, 1 H), 6.84 (d, J = 7.9 Hz, 1 H), 6.86 (d, J = 2.4 Hz, 1 H), 6.87 (dd, J = 9.1, 2.4 Hz, 1 H), 7.27 (d, J = 9.1 Hz, 1 H), 7.43 (d, J = 3.9 Hz, 1 H) |
| 7-(4-Cyclopentylsulfonyloxy-2-methoxyphenyl)-8-(5-methylthiophen-2-ylcarbonyloxymethyl)-1,3,3-trimethyl-3,4-dihydro-1H-quinoxalin-2-one (Compound No. 1-24)<br />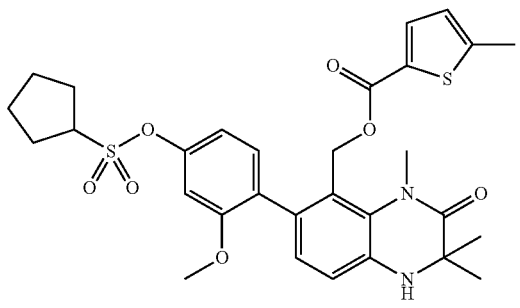 [SMILES: COc1cc(OS(=O)(=O)C2CCCC2)ccc1-c1ccc2c(c1COC(=O)c1ccc(C)s1)N(C)C(=O)C(C)(C)N2] | $^1$H-NMR (400 MHz, CDCl$_3$) δ 1.22 (s, 3 H), 1.41 (s, 3 H), 1.68-1.72 (m, 2 H), 1.88-1.93 (m, 2 H), 2.12-2.15 (m, 2 H), 2.21-2.30 (m, 2 H), 2.48 (s, 3 H), 3.45 (s, 3 H), 3.67-3.74 (m, 1 H), 3.76 (s, 3 H), 3.81 (s, 1 H), 5.08 (d, J = 13.3 Hz, 1 H), 5.25 (d, J = 13.3 Hz, 1 H), 6.70 (d, J = 3.7 Hz, 1 H), 6.76 (d, J = 8.0 Hz, 1 H), 6.84 (d, J = 8.0 Hz, 1 H), 6.86 (d, J = 2.1 Hz, 1 H), 6.87 (dd, J = 7.8, 2.1 Hz, 1 H), 7.27 (d, J = 7.8 Hz, 1 H), 7.43 (d, J = 3.7 Hz, 1 H) |
| 7-(2-Methoxy-4-methylsulfonyloxyphenyl)-8-(2-methoxy-5-nitrophenoxymethyl)-1,3,3-trimethyl-3,4-dihydro-1H-quinoxalin-2-one (Compound No. 1-25)<br />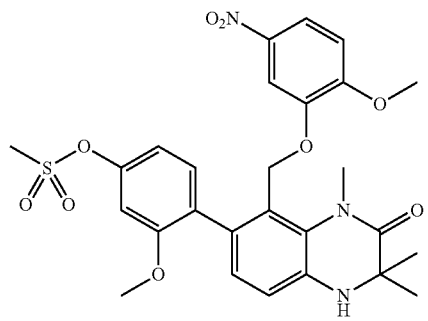 | $^1$H-NMR (500 MHz, CDCl$_3$) δ 0.76 (s, 3 H), 1.33 (s, 3 H), 3.20 (s, 3 H), 3.53 (s, 3 H), 3.71 (s, 1 H), 3.84 (s, 3 H), 3.86 (s, 3 H), 4.92 (d, J = 13.7 Hz, 1 H), 5.41 (d, J = 13.7 Hz, 1 H), 6.71 (d, J = 7.9 Hz, 1 H), 6.76 (d, J = 8.9 Hz, 1 H), 6.85 (d, J = 7.9 Hz, 1 H), 6.92 (d, J = 2.3 Hz, 1 H), 7.00 (dd, J = 8.2, 2.3 Hz, 1 H), 7.11 (d, J = 2.4 Hz, 1 H), 7.49 (d, J = 8.2 Hz, 1 H), 7.74 (dd, J = 8.9, 2.4 Hz, 1 H) |

| | | |
|---|---|---|
| 8-(2-Methoxy-5-nitrophenoxymethyl)-7-[2-methoxy-4-(3,3,3-trifluoropropylsulfonyloxy)phenyl]-1,3,3-trimethyl-3,4-dihydro-1H-quinoxalin-2-one (Compound No. 1-26) 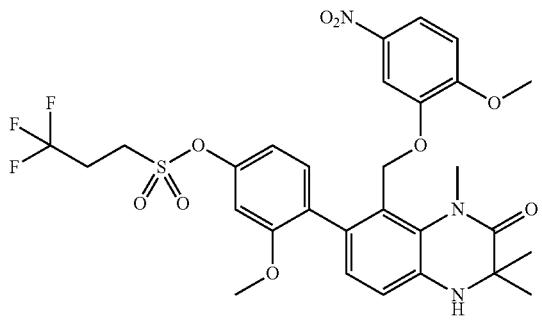 | $^1$H-NMR (500 MHz, CDCl$_3$) δ 0.79 (s, 3 H), 1.33 (s, 3 H), 2.80-2.89 (m, 2 H), 3.51-3.55 (m, 2 H), 3.53 (s, 3 H), 3.73 (s, 1 H), 3.84 (s, 3 H), 3.86 (s, 3 H), 4.90 (d, J = 13.7 Hz, 1 H), 5.39 (d, J = 13.7 Hz, 1 H), 6.72 (d, J = 8.1 Hz, 1 H), 6.76 (d, J = 9.1 Hz, 1 H), 6.85 (d, J = 8.1 Hz, 1 H), 6.88 (d, J = 2.3 Hz, 1 H), 6.97 (dd, J = 8.2, 2.3 Hz, 1 H), 7.12 (d, J = 2.5 Hz, 1 H), 7.51 (d, J = 8.2 Hz, 1 H), 7.75 (dd, J = 9.1, 2.5 Hz, 1 H) | |
| 7-(4-Isobutylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-27) 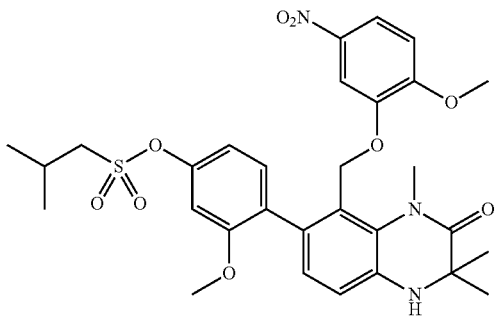 [SMILES: COc1ccc([N+](=O)[O-])cc1OCc1c(-c2ccc(OS(=O)(=O)CC(C)C)cc2OC)ccc2c1N(C)C(=O)C(C)(C)N2] | $^1$H-NMR (400 MHz, CDCl$_3$) δ 0.74 (s, 3 H), 1.19 (d, J = 6.8 Hz, 6 H), 1.33 (s, 3 H), 2.43-2.50 (m, 1 H), 3.21 (d, J = 6.8 Hz, 2 H), 3.53 (s, 3 H), 3.71 (br s, 1 H), 3.84 (s, 3 H), 3.85 (s, 3 H), 4.93 (d, J = 13.7 Hz, 1 H), 5.42 (d, J = 13.7 Hz, 1 H), 6.71 (d, J = 7.9 Hz, 1 H), 6.75 (d, J = 9.0 Hz, 1 H), 6.86 (d, J = 7.9 Hz, 1 H), 6.91 (d, J = 2.3 Hz, 1 H), 6.98 (dd, J = 8.3, 2.3 Hz, 1 H), 7.11 (d, J = 2.6 Hz, 1 H), 7.48 (d, J = 8.3 Hz, 1 H), 7.74 (dd, J = 9.0, 2.6 Hz, 1 H) | |
| 7-(4-Cyclopentylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-28) 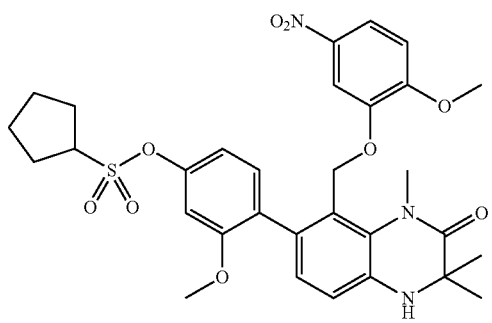 [SMILES: COc1ccc([N+](=O)[O-])cc1OCc1c(-c2ccc(OS(=O)(=O)C3CCCC3)cc2OC)ccc2c1N(C)C(=O)C(C)(C)N2] | $^1$H-NMR (400 MHz, CDCl$_3$) δ 0.74 (s, 3 H), 1.33 (s, 3 H), 1.69-1.74 (m, 2 H), 1.88-1.92 (m, 2 H), 2.14-2.19 (m, 2 H), 2.25-2.30 (m, 2 H), 3.53 (s, 3 H), 3.71 (br s, 1 H), 3.73-3.77 (m, 1 H), 3.84 (s, 3 H), 3.86 (s, 3 H), 4.93 (d, J = 13.8 Hz, 1 H), 5.42 (d, J = 13.8 Hz, 1 H), 6.71 (d, J = 8.1 Hz, 1 H), 6.75 (d, J = 9.0 Hz, 1 H), 6.85 (d, J = 8.1 Hz, 1 H), 6.92 (d, J = 2.3 Hz, 1 H), 6.98 (dd, J = 8.2, 2.3 Hz, 1 H), 7.11 (d, J = 2.6 Hz, 1 H), 7.47 (d, J = 8.2 Hz, 1 H), 7.74 (dd, J = 9.0, 2.6 Hz, 1 H) | |

| Compound | NMR |
|---|---|
| 7-(4-Isopropylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-29) 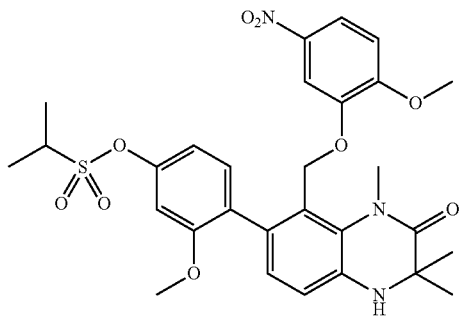 [SMILES: COc1ccc([N+](=O)[O-])cc1OCc1c(-c2ccc(OS(=O)(=O)C(C)C)cc2OC)ccc2c1N(C)C(=O)C(C)(C)N2] | $^1$H-NMR (500 MHz, CDCl$_3$) δ 0.75 (s, 3 H), 1.33 (s, 3 H), 1.59 (d, J = 7.0 Hz, 6 H), 3.50-3.56 (m, 1 H), 3.53 (s, 3 H), 3.70 (br s, 1 H), 3.84 (s, 3 H), 3.85 (s, 3 H), 4.93 (d, J = 13.7 Hz, 1 H), 5.41 (d, J = 13.7 Hz, 1 H), 6.71 (d, J = 8,1 Hz, 1 H), 6.75 (d, J = 8.9 Hz, 1 H), 6.85 (d, J = 8.1 Hz, 1 H), 6.91 (d, J = 2.1 Hz, 1 H), 6.98 (dd, J = 8.2, 2.1 Hz, 1 H), 7.12 (d, J = 2.6 Hz, 1 H), 7.48 (d, J = 8.2 Hz, 1 H), 7.74 (dd, J = 8.9, 2.6 Hz, 1 H) |
| 7-(4-Cyclopropylsulfonyloxy-2-methoxyphenyl)-8-(2-methoxy-5-nitrophenoxymethyl)-1,3,3-trimethyl-3,4-dihydro-1H-quinoxalin-2-one (Compound No. 1-30) 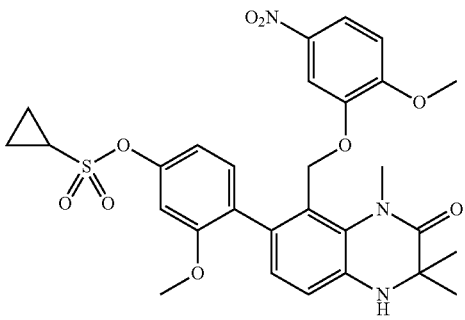 [SMILES: COc1ccc([N+](=O)[O-])cc1OCc1c(-c2ccc(OS(=O)(=O)C3CC3)cc2OC)ccc2c1N(C)C(=O)C(C)(C)N2] | $^1$H-NMR (400 MHz, CDCl$_3$) δ 0.75 (s, 3 H), 1.14-1.18 (m, 2 H), 1.29-1.32 (m, 2 H), 1.34 (s, 3 H), 2.61-2.68 (m, 1 H), 3.53 (s, 3 H), 3.71 (br s, 1 H), 3.84 (s, 3 H), 3.86 (s, 3 H), 4.91 (d, J = 13.8 Hz, 1 H), 5.41 (d, J = 13.8 Hz, 1 H), 6.71 (d, J = 7.9 Hz, 1 H), 6.76 (d, J = 8.9 Hz, 1 H), 6.86 (d, J = 7.9 Hz, 1 H), 6.93 (d, J = 2.2 Hz, 1 H), 7.04 (dd, J = 8.3, 2.2 Hz, 1 H), 7.11 (d, J = 2.6 Hz, 1 H), 7.48 (d, J = 8.3 Hz, 1 H), 7.74 (dd, J = 8.9, 2.6 Hz, 1 H) |
| 8-(2-Methoxy-5-nitrophenoxymethyl)-7-(2-methoxy-4-propylsulfonyloxyphenyl)-1,3,3-trimethyl-3,4-dihydro-1H-quinoxalin-2-one (Compound No. 1-31) 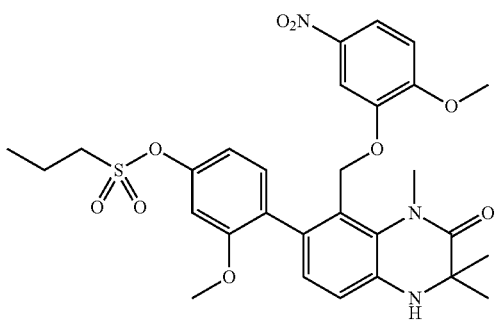 [SMILES: CCCS(=O)(=O)Oc1ccc(-c2ccc3c(c2COc2cc([N+](=O)[O-])ccc2OC)N(C)C(=O)C(C)(C)N3)c(OC)c1] | $^1$H-NMR (400 MHz, DMSO-d$_6$) δ 0.73 (s, 3 H), 1.02 (t, J = 7.5 Hz, 3 H), 1.16 (s, 3 H), 1.84 (sextet, J = 7.5 Hz, 2 H), 3.37 (s, 3 H), 3.50 (t, J = 7.5 Hz, 2 H), 3.79 (s, 3 H), 3.79 (s, 3 H), 4.82 (d, J = 13.7 Hz, 1 H), 5.39 (d, J = 13.7 Hz, 1 H), 6.15 (s, 1 H), 6.80 (s, 2 H), 6.97 (dd, J = 8.2, 2.3 Hz, 1 H), 7.00 (d, J = 2.3 Hz, 1 H), 7.04 (d, J = 9.0 Hz, 1 H), 7.13 (d, J = 2.7 Hz, 1 H), 7.39 (d, J = 8.2 Hz, 1 H), 7.76 (dd, J = 9.0, 2.7 Hz, 1 H) |

| | |
|---|---|
| 7-(4-Cyclopropylsulfonyloxy-2-methoxyphenyl)-8-(2-methyl-5-nitrophenoxymethyl)-1,3,3-trimethyl-3,4-dihydro-1H-quinoxalin-2-one (Compound No. 1-32)<br>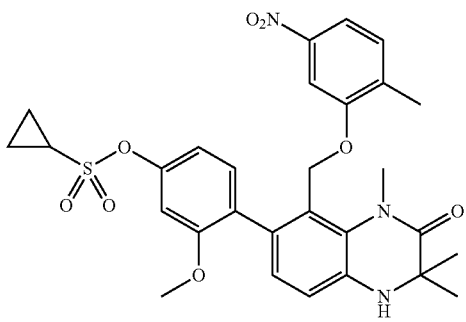 [SMILES: COc1cc(OS(=O)(=O)C2CC2)ccc1-c1ccc2c(c1COc1cc([N+](=O)[O-])ccc1C)N(C)C(=O)C(C)(C)N2] | $^1$H-NMR (500 MHz, CDCl$_3$) δ 0.65 (s, 3 H), 1.12-1.33 (m, 4 H), 1.37 (s, 3 H), 2.17 (s, 3 H), 2.63-2.68 (m, 1 H), 3.52 (s, 3 H), 3.72 (s, 1 H), 3.86 (s, 3 H), 4.93 (d, J = 14.1 Hz, 1 H), 5.44 (d, J = 14.1 Hz, 1 H), 6.72 (d, J = 8.2 Hz, 1 H), 6.89 (d, J = 8.2 Hz, 1 H), 6.96 (d, J = 2.1 Hz, 1 H), 7.00 (d, J = 2.2 Hz, 1 H), 7.08 (dd, J = 8.2, 2.1 Hz, 1 H), 7.11 (d, J = 8.2 Hz, 1 H), 7.54 (d, J = 8.2 Hz, 1 H), 7.59 (dd, J = 8.2, 2.2 Hz, 1 H) |
| 7-[2-Methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one (Compound No. 1-33)<br>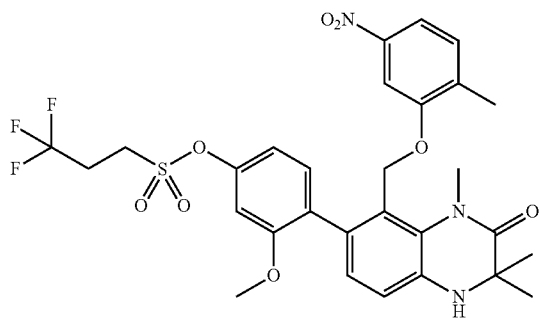 | $^1$H-NMR (400 MHz, CDCl$_3$) δ 0.64 (s, 3 H), 1.37 (s, 3 H), 2.17 (s, 3 H), 2.79-2.91 (m, 2 H), 3.52 (s, 3 H), 3.52-3.56 (m, 2 H), 3.74 (s, 1 H), 3.86 (s, 3 H), 4.92 (d, J = 13.9 Hz, 1 H), 5.44 (d, J = 13.9 Hz, 1 H), 6.72 (d, J = 8.1 Hz, 1 H), 6.89 (d, J = 8.1 Hz, 1 H), 6.91 (d, J = 2.2 Hz, 1 H), 7.00 (d, J = 2.2 Hz, 1 H), 7.02 (dd, J = 8.3, 2.2 Hz, 1 H), 7.11 (d, J = 8.3 Hz, 1 H), 7.57 (d, J = 8.1 Hz, 1 H), 7.59 (dd, J = 8.1, 2.2 Hz, 1 H) |
| 7-(4-Isobutylsulfonyloxy-2-methoxyphenyl)-8-(2-methyl-5-nitrophenoxymethyl)-1,3,3-trimethyl-3,4-dihydro-1H-quinoxalin-2-one (Compound No. 1-34)<br>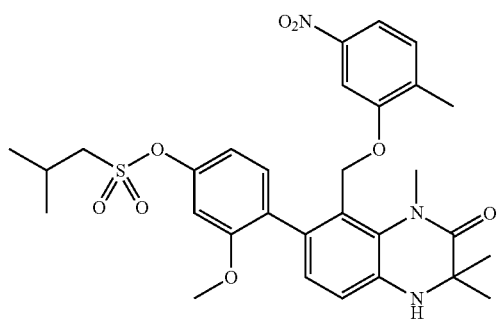 [SMILES: COc1cc(OS(=O)(=O)CC(C)C)ccc1-c1ccc2c(c1COc1cc([N+](=O)[O-])ccc1C)N(C)C(=O)C(C)(C)N2] | $^1$H-NMR (500 MHz, CDCl$_3$) δ 0.63 (s, 3 H), 1.19 (d, J = 6.7 Hz, 3 H), 1.20 (d, J = 6.7 Hz, 3 H), 1.37 (s, 3 H), 2.17 (s, 3 H), 2.43-2.51 (m, 1 H), 3.22 (d, J = 6.7 Hz, 2 H), 3.52 (s, 3 H), 3.72 (s, 1 H), 3.86 (s, 3 H), 4.94 (d, J = 14.1 Hz, 1 H), 5.45 (d, J = 14.1 Hz, 1 H), 6.71 (d, J = 7.9 Hz, 1 H), 6.89 (d, J = 7.9 Hz, 1 H), 6.94 (d, J = 2.3 Hz, 1 H), 7.00 (d, J = 2.1 Hz, 1 H), 7.02 (dd, J = 8.2, 2.3 Hz, 1 H), 7.11 (d, J = 8.2 Hz, 1 H), 7.55 (d, J = 8.2 Hz, 1 H), 7.58 (dd, J = 8.2, 2.1 Hz, 1 H) |

| | |
|---|---|
| 7-(4-Isopropylsulfonyloxy-2-methoxyphenyl)-8-(2-methyl-5-nitrophenoxymethyl)-1,3,3-trimethyl-3,4-dihydro-1H-quinoxalin-2-one (Compound No. 1-35)<br />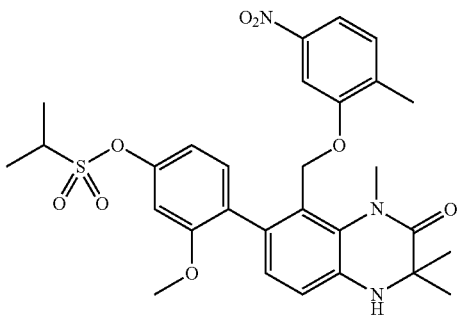 [SMILES: COc1cc(OS(=O)(=O)C(C)C)ccc1-c1ccc2c(c1COc1cc([N+](=O)[O-])ccc1C)N(C)C(=O)C(C)(C)N2] | $^1$H-NMR (500 MHz, CDCl$_3$) δ 0.64 (s, 3 H), 1.36 (s, 3 H), 1.58 (d, J = 6.9 Hz, 3 H), 1.60 (d, J = 6.9 Hz, 3 H), 2.17 (s, 3 H), 3.48-3.56 (m, 1 H), 3.52 (s, 3 H), 3.71 (s, 1 H), 3.86 (s, 3 H), 4.94 (d, J = 14.1 Hz, 1 H), 5.44 (d, J = 14.1 Hz, 1 H), 6.71 (d, J = 8.1 Hz, 1 H), 6.89 (d, J = 8.1 Hz, 1 H), 6.94 (d, J = 2.2 Hz, 1 H), 7.01 (d, J = 2.1 Hz, 1 H), 7.02 (dd, J = 8.5, 2.2 Hz, 1 H), 7.11 (d, J = 8.5 Hz, 1 H), 7.55 (d, J = 8.2 Hz, 1 H), 7.58 (dd, J = 8.2, 2.1 Hz, 1 H) |
| 7-(2-Methoxy-4-methylsulfonyloxyphenyl)-8-(2-methyl-5-nitrophenoxymethyl)-1,3,3-trimethyl-3,4-dihydro-1H-quinoxalin-2-one (Compound No. 1-36)<br />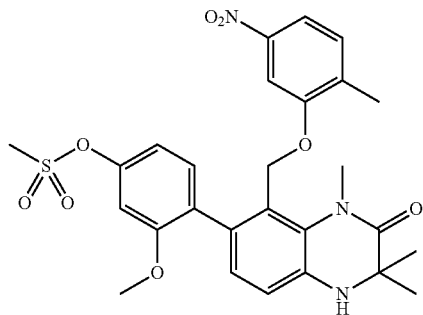 | $^1$H-NMR (400 MHz, CDCl$_3$) δ 0.64 (s, 3 H), 1.37 (s, 3 H), 2.17 (s, 3 H), 3.21 (s, 3 H), 3.51 (s, 3 H), 3.73 (s, 1 H), 3.86 (s, 3 H), 4.94 (d, J = 14.2 Hz, 1 H), 5.45 (d, J = 14.2 Hz, 1 H), 6.72 (d, J = 8.1 Hz, 1 H), 6.89 (d, J = 8.1 Hz, 1 H), 6.95 (d, J = 2.3 Hz, 1 H), 7.00 (d, J = 2.1 Hz, 1 H), 7.05 (dd, J = 8.2, 2.3 Hz, 1 H), 7.11 (d, J = 8.2 Hz, 1 H), 7.56 (d, J = 8.3 Hz, 1 H), 7.59 (dd, J = 8.3, 2.1 Hz, 1 H) |
| 7-(4-Cyclopentylsulfonyloxy-2-methoxyphenyl)-8-(2-methyl-5-nitrophenoxymethyl)-1,3,3-trimethyl-3,4-dihydro-1H-quinoxalin-2-one (Compound No. 1-37)<br />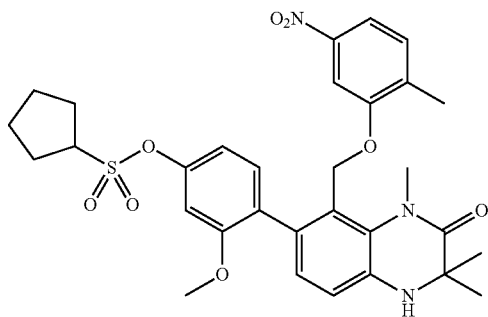 [SMILES: COc1cc(OS(=O)(=O)C2CCCC2)ccc1-c1ccc2c(c1COc1cc([N+](=O)[O-])ccc1C)N(C)C(=O)C(C)(C)N2] | $^1$H-NMR (500 MHz, CDCl$_3$) δ 0.64 (s, 3 H), 1.36 (s, 3 H), 1.68-1.74 (m, 2 H), 1.88-1.94 (m, 2 H), 2.14-2.21 (m, 2 H), 2.17 (s, 3 H), 2.24-2.32 (m, 2 H), 3.52 (s, 3 H), 3.71 (s, 1 H), 3.73-3.79 (m, 1 H), 3.86 (s, 3 H), 4.94 (d, J = 14.1 Hz, 1 H), 5.44 (d, J = 14.1 Hz, 1 H), 6.71 (d, J = 7.9 Hz, 1 H), 6.89 (d, J = 7.9 Hz, 1 H), 6.94 (d, J = 2.3 Hz, 1 H), 7.00 (d, J = 2.2 Hz, 1 H), 7.02 (dd, J = 8.2, 2.3 Hz, 1 H), 7.11 (d, J = 8.2 Hz, 1 H), 7.54 (d, J = 8.2 Hz, 1 H), 7.58 (dd, J = 8.2, 2.2 Hz, 1 H) |
| 7-(2-Methoxy-4-propylsulfonyloxyphenyl)-8-(2-methyl-5-nitrophenoxymethyl)-1,3,3-trimethyl-3,4-dihydro-1H-quinoxalin-2-one (Compound No. 1-38)<br />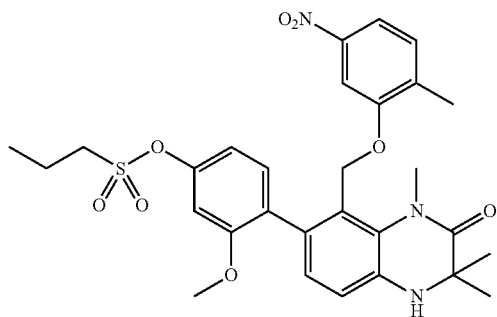 [SMILES: CCCS(=O)(=O)Oc1ccc(-c2ccc3c(c2COc2cc([N+](=O)[O-])ccc2C)N(C)C(=O)C(C)(C)N3)c(OC)c1] | $^1$H-NMR (400 MHz, CDCl$_3$) δ 0.63 (s, 3 H), 1.15 (t, J = 7.5 Hz, 3 H), 1.37 (s, 3 H), 2.01-2.11 (m, 2 H), 2.17 (s, 3 H), 3.27-3.31 (m, 2 H), 3.52 (s, 3 H), 3.72 (s, 1 H), 3.86 (s, 3 H), 4.94 (d, J = 14.2 Hz, 1 H), 5.45 (d, J = 14.2 Hz, 1 H), 6.72 (d, J = 8.0 Hz, 1 H), 6.89 (d, J = 8.0 Hz, 1 H), 6.94 (d, J = 2.2 Hz, 1 H), 7.00 (d, J = 2.2 Hz, 1 H), 7.02 (dd, J = 8.3, 2.2 Hz, 1 H), 7.11 (d, J = 8.3 Hz, 1 H), 7.55 (d, J = 8.3 Hz, 1 H), 7.58 (dd, J = 8.3, 2.2 Hz, 1 H) |

| | |
|---|---|
| 7-(2-Methoxy-4-propylsulfonyloxyphenyl)-8-(4-methylbenzoyloxymethyl)-1,3,3-trimethyl-3,4-dihydro-1H-quinoxalin-2-one (Compound No. 1-39)<br />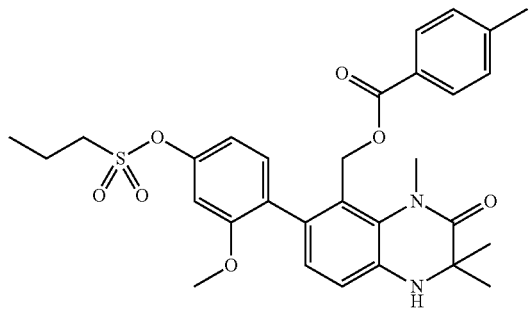 [SMILES: CCCS(=O)(=O)Oc1ccc(-c2ccc3c(c2COC(=O)c2ccc(C)cc2)N(C)C(=O)C(C)(C)N3)c(OC)c1] | $^1$H-NMR (400 MHz, CDCl$_3$) δ 1.13 (t, J = 7.4 Hz, 3 H), 1.21 (s, 3 H), 1.42 (s, 3 H), 1.98-2.07 (m, 2 H), 2.37 (s, 3 H), 3.21-3.25 (m, 2 H), 3.47 (s, 3 H), 3.74 (s, 3 H), 3.81 (s, 1 H), 5.13 (d, J = 13.2 Hz, 1 H), 5.29 (d, J = 13.2 Hz, 1 H), 6.76 (d, J = 8.1 Hz, 1 H), 6.83-6.86 (m, 3 H), 7.16 (d, J = 8.1 Hz, 2 H), 7.27 (d, J = 8.8 Hz, 1 H), 7.71 (d, J = 8.1 Hz, 2 H) |
| 7-[4-(3-Chloropropylsulfonyloxy)-2-methoxyphenyl]-8-(5-fluoro-2-methylphenoxymethyl)-1,3,3-trimethyl-3,4-dihydro-1H-quinoxalin-2-one (Compound No. 1-40)<br />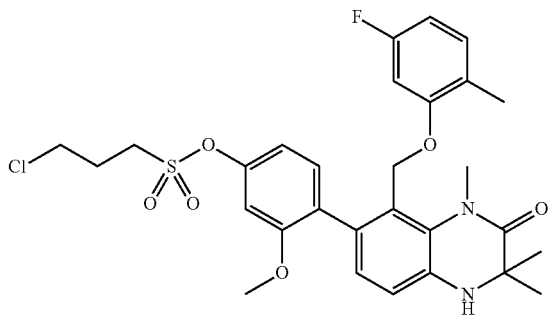 [SMILES: COc1cc(OS(=O)(=O)CCCCl)ccc1-c1ccc2c(c1COc1cc(F)ccc1C)N(C)C(=O)C(C)(C)N2] | $^1$H-NMR (500 MHz, CDCl$_3$) δ 0.99 (s, 3 H), 1.27 (s, 3 H), 2.01 (s, 3 H), 2.45-2.51 (m, 2 H), 3.46 (s, 3 H), 3.49 (t, J = 7.3 Hz, 2 H), 3.75 (t, J = 6.1Hz, 3 H), 3.84 (s, 3 H), 4.80 (d, J = 13.4 Hz, 1 H), 5.16 (d, J = 13.4 Hz, 1 H), 6.06 (dd, J = 11.3, 2.4 Hz, 1 H), 6.41 (td, J = 8.2, 2.4 Hz, 1 H), 6.73 (d, J = 7.9 Hz, 1 H), 6.86 (d, J = 7.9 Hz, 1 H), 6.90-6.92 (m, 1 H), 6.92 (d, J = 2.4 Hz, 1 H), 6.96 (dd, J = 8.2, 2.4 Hz, 1 H), 7.33 (d, J = 8.2 Hz, 1 H) |
| 7-(4-Chloromethylsulfonyloxy-2-methoxyphenyl)-8-(5-fluoro-2-methylphenoxymethyl)-1,3,3-trimethyl-3,4-dihydro-1H-quinoxalin-2-one (Compound No. 1-41)<br />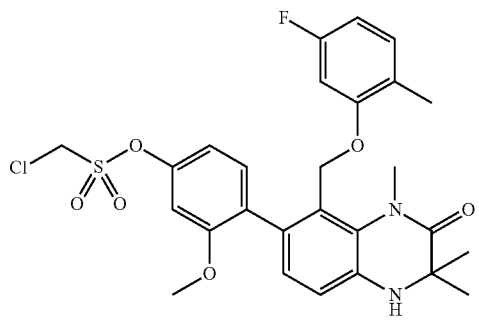 [SMILES: COc1cc(OS(=O)(=O)CCl)ccc1-c1ccc2c(c1COc1cc(F)ccc1C)N(C)C(=O)C(C)(C)N2] | $^1$H-NMR (400 MHz, CDCl$_3$) δ 1.01 (s, 3 H), 1.28 (s, 3 H), 2.01 (s, 3 H), 3.46 (s, 3 H), 3.77 (s, 1 H), 3.84 (s, 3 H), 4.68 (s, 2 H), 4.77 (d, J = 13.3 Hz, 1 H), 5.15 (d, J = 13.3 Hz, 1 H), 6.06 (dd, J = 11.2, 2.4 Hz, 1 H), 6.42 (td, J = 8.3, 2.4 Hz, 1 H), 6.74 (d, J = 8.1 Hz, 1 H), 6.85 (d, J = 8.1 Hz, 1 H), 6.90-6.94 (m, 1 H), 6.95 (d, J = 2.2 Hz, 1 H), 7.02 (dd, J = 8.3, 2.2 Hz, 1 H), 7.35 (d, J = 8.3 Hz, 1 H) |

| Compound | NMR |
|---|---|
| 7-(4-cyclopentylsulfonyloxy-2-methoxyphenyl)-8-(5-fluoro-2-methyl-phenylaminomethyl)-1,3,3-trimethyl-3,4-dihydro-1H-quinoxalin-2-one (Compound No. 1-42) 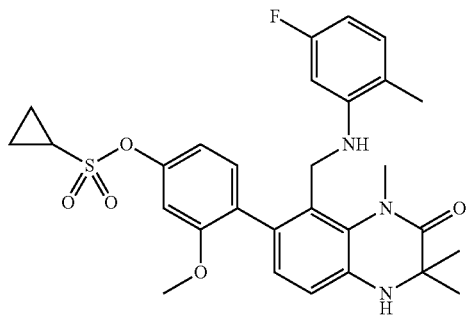 [SMILES: COc1cc(OS(=O)(=O)C2CC2)ccc1-c1ccc2c(c1CNc1cc(F)ccc1C)N(C)C(=O)C(C)(C)N2] | $^1$H-NMR (500 MHz, CDCl$_3$) δ 1.04-1.06 (m, 2 H), 1.18 (s, 3 H), 1.22-1.25 (m, 2 H), 1.40 (s, 3 H), 1.85 (s, 3 H), 2.50 (tt, J = 7.9, 4.6 Hz, 1 H), 3.43 (s, 3 H), 3.72-3.75 (m, 1 H), 3.78 (s, 1 H), 3.80 (s, 3 H), 4.10 (dd, J = 13.9, 5.5 Hz, 1 H), 4.18 (dd, J = 13.9, 4.9 Hz, 1 H), 5.97 (dd, J = 11.6, 2.5 Hz, 1 H), 6.22 (td, J = 8.3, 2.5 Hz, 1 H), 6.72 (d, J = 8.1 Hz, 1 H), 6.80-6.84 (m, 1 H), 6.82 (d, J = 8.1 Hz, 1 H), 6.91 (d, J = 2.3 Hz, 1 H), 6.97 (dd, J = 8.2, 2.3 Hz, 1 H), 7.22 (d, J = 8.2 Hz, 1 H) |
| 7-(4-cyclopentylsulfonyloxy-2-methoxyphenyl)-8-(5-fluoro-2-methyl-phenylaminomethyl)-1,3,3-trimethyl-3,4-dihydro-1H-quinoxalin-2-one (Compound No. 1-43) 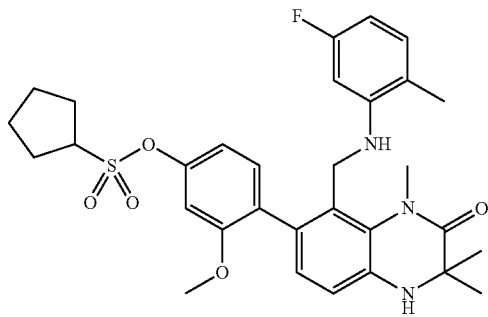 | $^1$H-NMR (500 MHz, CDCl$_3$) δ 1.17 (s, 3 H), 1.40 (s, 3 H), 1.67-1.73 (m, 2 H), 1.84 (s, 3 H), 1.86-1.92 (m, 2 H), 2.10-2.16 (m, 2 H), 2.21-2.26 (m, 2 H), 3.42 (s, 3 H), 3.64-3.70 (m, 1 H), 3.72-3.76 (m, 1 H), 3.78 (s, 1 H), 3.80 (s, 3 H), 4.12 (dd, J = 14.1, 5.1 Hz, 1 H), 4.20 (dd, J = 14.1, 4.9 Hz, 1 H), 5.97 (dd, J = 11.6, 2.5 Hz, 1 H), 6.22 (td, J = 8.4, 2.5 Hz, 1 H), 6.71 (d, J = 7.9 Hz, 1 H), 6.81-6.84 (m, 1 H), 6.81 (d, J = 7.9 Hz, 1 H), 6.89 (d, J = 2.3 Hz, 1 H), 6.92 (dd, J = 8.1, 2.3 Hz, 1 H), 7.21 (d, J = 8.1 Hz, 1 H) |
| 8-(5-Fluoro-2-methylphenylaminomethyl)-7-(2-methoxy-4-propyl-sulfonyloxyphenyl)-1,3,3-trimethyl-3,4-dihydro-1H-quinoxalin-2-one (Compound No. 1-44) 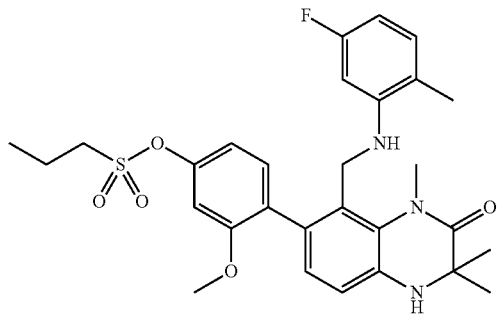 [SMILES: CCCS(=O)(=O)Oc1ccc(-c2ccc3c(c2CNc2cc(F)ccc2C)N(C)C(=O)C(C)(C)N3)c(OC)c1] | $^1$H-NMR (400 MHz, CDCl$_3$) δ 1.13 (t, J = 7.4 Hz, 3 H), 1.17 (s, 3 H), 1.40 (s, 3 H), 1.84 (s, 3 H), 1.98 -2.06 (m, 2 H), 3.20-3.24 (m, 2 H), 3.42 (s, 3 H), 3.71-3.75 (m, 1 H), 3.78 (s, 1 H), 3.80 (s, 3 H), 4.13 (dd, J = 13.9, 5.0 Hz, 1 H), 4.21 (dd, J = 13.9, 4.9 Hz, 1 H), 5.97 (dd, J = 11.5, 2.5 Hz, 1 H), 6.22 (td, J = 8.4, 2.5 Hz, 1 H), 6.71 (d, J = 7.9 Hz, 1 H), 6.80-6.85 (m, 1 H), 6.81 (d, J = 7.9 Hz, 1 H), 6.89 (d, J = 2.3 Hz, 1 H), 6.92 (dd, J = 8.2, 2.3 Hz, 1 H), 7.23 (d, J = 8.2 Hz, 1 H) |

Example 2

7-(2-Methoxy-4-methylsulfonyloxyphenyl)-8-(2-methoxyphenylaminomethyl)-1,3,3-trimethyl-3,4-dihydro-1H-quinoxalin-2-one (Compound No. 2-1)

8-[N-(9-Fluorenylmethoxycarbonyl)-N-(2-methoxyphenyl)aminomethyl]-7-(4-hydroxy-2-methoxyphenyl)-1,3,3-trimethyl-3,4-dihydro-1H-quinoxalin-2-one (Reference Compound No. 14-6, 30.9 mg, 0.0461 mmol) was dissolved in dichloromethane (0.5 mL), and triethylamine (16 μL, 0.115 mmol) and methanesulfonyl chloride (5 μL, 0.0646 mmol) were added thereto successively. After the reaction mixture was stirred at room temperature for 1 hour, it was purified by silica gel column chromatography (hexane-ethyl acetate). The obtained colorless amorphous product was dissolved in N,N-dimethylformamide (0.5 mL) and piperidine (30 μL) was added thereto. After the reaction mixture was stirred at room temperature for 20 minutes, it was diluted with ethyl acetate (30 mL). The mixture was washed with water (30 mL) and saturated brine (30 mL) successively, dried over anhydrous magnesium sulfate, and then the solvent was removed under reduced pressure. The obtained residue was purified by silica gel column chromatography (hexane-ethyl acetate) to give the titled compound (13.7 mg) as a colorless amorphous product. (Yield 56%)

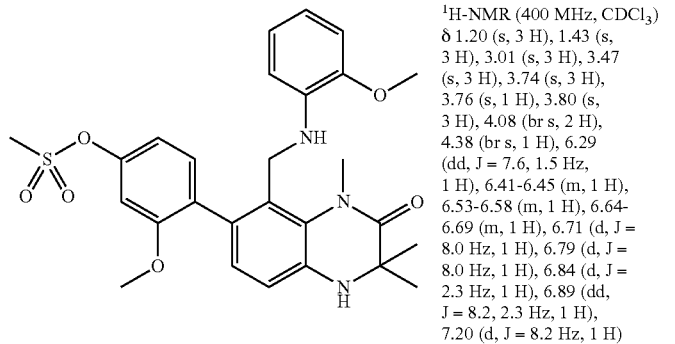

| | ¹H-NMR (400 MHz, CDCl₃) δ 1.20 (s, 3 H), 1.43 (s, 3 H), 3.01 (s, 3 H), 3.47 (s, 3 H), 3.74 (s, 3 H), 3.76 (s, 1 H), 3.80 (s, 3 H), 4.08 (br s, 2 H), 4.38 (br s, 1 H), 6.29 (dd, J = 7.6, 1.5 Hz, 1 H), 6.41-6.45 (m, 1 H), 6.53-6.58 (m, 1 H), 6.64-6.69 (m, 1 H), 6.71 (d, J = 8.0 Hz, 1 H), 6.79 (d, J = 8.0 Hz, 1 H), 6.84 (d, J = 2.3 Hz, 1 H), 6.89 (dd, J = 8.2, 2.3 Hz, 1 H), 7.20 (d, J = 8.2 Hz, 1 H) |

Using any compounds among Reference Compound No. 14-6 and commercially available compounds, the following Compounds No. 2-2 to 2-7 were obtained by a method similar to that of Compound No. 2-1.

7-(4-Cyclopropylsulfonyloxy-2-methoxyphenyl)-8-(2-methoxy-phenylaminomethyl)-1,3,3-trimethyl-3,4-dihydro-1H-quinoxalin-2-one (Compound No. 2-2)

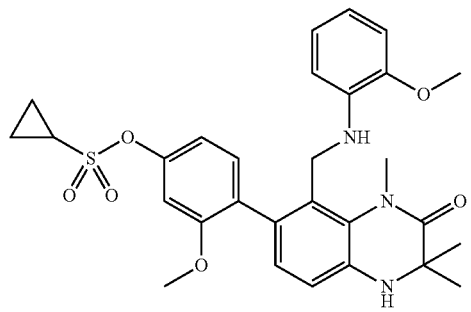 [SMILES: COc1ccccc1NCc1c(-c2ccc(OS(=O)(=O)C3CC3)cc2OC)ccc2c1N(C)C(=O)C(C)(C)N2]

¹H-NMR (400 MHz, CDCl₃) δ 0.96-0.98 (m, 2 H), 1.16-1.19 (m, 2 H), 1.21 (s, 3 H), 1.43 (s, 3 H), 2.33-2.38 (m, 1 H), 3.48 (s, 3 H), 3.74 (s, 3 H), 3.76 (s, 1 H), 3.79 (s, 3 H), 4.05 (s, 2 H), 4.41 (br s, 1 H), 6.29 (dd, J = 7.8, 1.5 Hz, 1 H), 6.55 (td, J = 7.8, 1.5 Hz, 1 H), 6.65 (dd, J = 7.8, 1.5 Hz, 1 H), 6.68-6.72 (m, 1 H), 6.71 (d, J = 7.8 Hz, 1 H), 6.79 (d, J = 7.8 Hz, 1 H), 6.86 (d, J = 2.3 Hz, 1 H), 6.91 (dd, J = 8.1, 2.3 Hz, 1 H), 7.18 (d, J = 8.1 Hz, 1 H)

8-(2-Methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one (Compound No. 2-3)

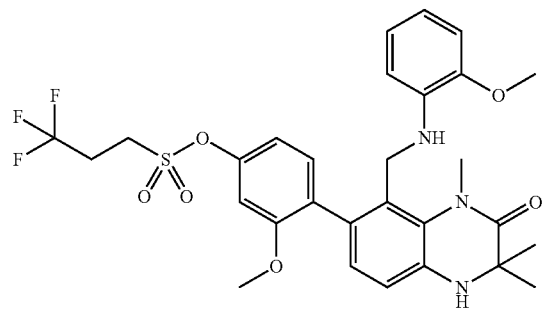 [SMILES: COc1ccccc1NCc1c(-c2ccc(OS(=O)(=O)CCC(F)(F)F)cc2OC)ccc2c1N(C)C(=O)C(C)(C)N2]

¹H-NMR (400 MHz, CDCl₃) δ 1.20 (s, 3 H), 1.43 (s, 3 H), 2.74-2.86 (m, 2 H), 3.39-3.44 (m, 2 H), 3.46 (s, 3 H), 3.73 (s, 3 H), 3.77 (s, 1 H), 3.80 (s, 3 H), 4.09 (s, 2 H), 4.39 (br s, 1 H), 6.29 (dd, J = 7.8, 1.4 Hz, 1 H), 6.56 (td, J = 7.8, 1.4 Hz, 1 H), 6.66 (dd, J = 7.8, 1.4 Hz, 1 H), 6.69-6.74 (m, 1 H), 6.70 (d, J = 7.8 Hz, 1 H), 6.78 (d, J = 7.8 Hz, 1 H), 6.80 (d, J = 2.4 Hz, 1 H), 6.85 (dd, J = 8.1, 2.4 Hz, 1 H), 7.22 (d, J = 8.3 Hz, 1 H)

| | |
|---|---|
| 7-(4-Isobutylsulfonyloxy-2-methoxyphenyl)-8-(2-methoxyphenyl-aminomethyl)-1,3,3-trimethyl-3,4-dihydro-1H-quinoxalin-2-one (Compound No. 2-4) 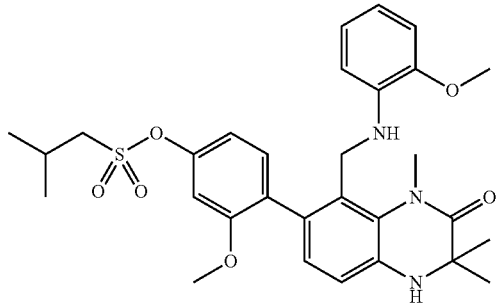 [SMILES: COc1ccccc1NCc1c(-c2ccc(OS(=O)(=O)CC(C)C)cc2OC)ccc2c1N(C)C(=O)C(C)(C)N2] | $^1$H-NMR (400 MHz, CDCl$_3$) δ 1.16 (d, J = 6.7 Hz, 6 H), 1.19 (s, 3 H), 1.42 (s, 3 H), 2.39-2.47 (m, 1 H), 3.12 (d, J = 6.4 Hz, 2 H), 3.46 (s, 3 H), 3.73 (s, 3 H), 3.75 (s, 1 H), 3.79 (s, 3 H), 4.10 (s, 2 H), 4.41 (br s, 1 H), 6.30 (dd, J = 7.7, 1.5 Hz, 1 H), 6.56 (td, J = 7.7, 1.5 Hz, 1 H), 6.65 (dd, J = 7.7, 1.5 Hz, 1 H), 6.70 (d, J = 7.9 Hz, 1 H), 6.71 (td, J = 7.7, 1.5 Hz, 1 H), 6.79 (d, J = 7.9 Hz, 1 H), 6.84 (d, J = 2.3 Hz, 1 H), 6.87 (dd, J = 8.2, 2.3 Hz, 1 H), 7.19 (d, J = 8.2 Hz, 1 H) |
| 7-(4-Isobutylsulfonyloxy-2-methoxyphenyl)-8-(2-methoxyphenyl-aminomethyl)-1,3,3-trimethyl-3,4-dihydro-1H-quinoxalin-2-one (Compound No. 2-5) 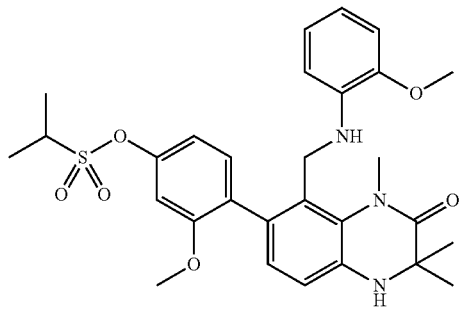 [SMILES: COc1ccccc1NCc1c(-c2ccc(OS(=O)(=O)C(C)C)cc2OC)ccc2c1N(C)C(=O)C(C)(C)N2] | $^1$H-NMR (400 MHz, CDCl$_3$) δ 1.19 (s, 3 H), 1.42 (s, 3 H), 1.54 (d, J = 6.8 Hz, 6 H), 3.41 (sept, J = 6.8 Hz, 1 H), 3.46 (s, 3 H), 3.73 (s, 3 H), 3.76 (s, 1 H), 3.79 (s, 3 H), 4.10 (s, 2 H), 4.43 (br s, 1 H), 6.30 (dd, J = 7.8, 1.4 Hz, 1 H), 6.56 (td, J = 7.8, 1.4 Hz, 1 H), 6.66 (dd, J = 7.8, 1.4 Hz, 1 H), 6.70 (d, J = 8.1 Hz, 1 H), 6.71 (td, J = 7.8, 1.4 Hz, 1 H), 6.79 (d, J = 8.1 Hz, 1 H), 6.84 (d, J = 2.2 Hz, 1 H), 6.88 (dd, J = 8.2, 2.2 Hz, 1 H), 7.18 (d, J = 8.2 Hz, 1 H) |
| 7-(4-Cyclopentylsulfonyloxy-2-methoxyphenyl)-8-(2-methoxyphenylaminomethyl)-1,3,3-trimethyl-3,4-dihydro-1H-quinoxalin-2-one (Compound No. 2-6) 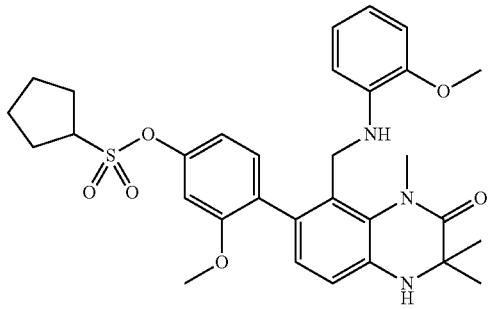 [SMILES: COc1ccccc1NCc1c(-c2ccc(OS(=O)(=O)C3CCCC3)cc2OC)ccc2c1N(C)C(=O)C(C)(C)N2] | $^1$H-NMR (500 MHz, CDCl$_3$) δ 1.19 (s, 3 H), 1.42 (s, 3 H), 1.66-1.69 (m, 2 H), 1.85-1.89 (m, 2 H), 2.07-2.13 (m, 2 H), 2.19-2.24 (m, 2 H), 3.46 (s, 3 H), 3.58-3.62 (m, 1 H), 3.73 (s, 3 H), 3.75 (s, 1 H), 3.79 (s, 3 H), 4.09 (s, 2 H), 4.42 (br s, 1 H), 6.29 (dd, J = 7.8, 1.4 Hz, 1 H), 6.56 (td, J = 7.8, 1.4 Hz, 1 H), 6.65 (dd, J = 7.8, 1.4 Hz, 1 H), 6.70 (d, J = 7.9 Hz, 1 H), 6.71 (td, J = 7.8, 1.4 Hz, 1 H), 6.78 (d, J = 7.9 Hz, 1 H), 6.84 (d, J = 2.3 Hz, 1 H), 6.88 (dd, J = 8.2, 2.3 Hz, 1 H), 7.18 (d, J = 8.2 Hz, 1 H) |
| 8-(2-Methoxyphenylaminomethyl)-7-(2-methoxy-4-propylsulfonyl-oxyphenyl)-1,3,3-trimethyl-3,4-dihydro-1H-quinoxalin-2-one (Compound No. 2-7) 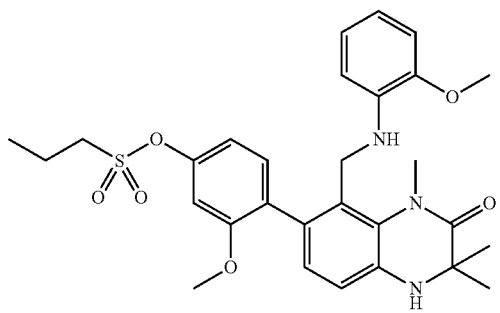 [SMILES: CCCS(=O)(=O)Oc1ccc(-c2ccc3c(c2CNc2ccccc2OC)N(C)C(=O)C(C)(C)N3)c(OC)c1] | $^1$H-NMR (500 MHz, CDCl$_3$) δ 1.11 (t, J = 7.5 Hz, 3 H), 1.19 (s, 3 H), 1.42 (s, 3 H), 1.96-2.04 (m, 2 H), 3.15-3.18 (m, 2 H), 3.46 (s, 3 H), 3.73 (s, 3 H), 3.76 (br s, 1 H), 3.79 (s, 3 H), 4.10 (br s, 2 H), 4.40 (br s, 1 H), 6.29 (d, J = 7.6 Hz, 1 H), 6.56 (t, J = 7.6 Hz, 1 H), 6.65 (d, J = 7.6 Hz, 1 H), 6.70 (d, J = 7.9 Hz, 1 H), 6.71 (t, J = 7.6 Hz, 1 H), 6.78 (d, J = 7.9 Hz, 1 H), 6.84 (d, J = 1.9 Hz, 1 H), 6.87 (dd, J = 8.0, 1.9 Hz, 1 H), 7.19 (d, J = 8.0 Hz, 1 H) |

Example 3

7-[4-(3-Benzylaminopropylsulfonyloxy)-2-methoxyphenyl]-8-(5-fluoro-2-methylphenoxymethyl)-1,3,3-trimethyl-3,4-dihydro-1H-quinoxalin-2-one (Compound No. 3-1)

A mixture of 7-[4-(3-chloropropylsulfonyloxy)-2-methoxyphenyl]-8-(5-fluoro-2-methylphenoxymethyl)-1,3,3-trimethyl-3,4-dihydro-1H-quinoxalin-2-one (Reference Compound No. 1-40, 50.0 mg, 0.0846 mmol), benzylamine (92.4 μL, 0.846 mmol), and potassium iodide (16.9 mg, 0.102 mmol) was suspended in anhydrous N,N-dimethylformamide (0.4 mL) and stirred at 50° C. for 5 hours. After cooling down, ethyl acetate (50 mL) was added thereto. The organic layer was washed with water (50 mL) and saturated brine (30 mL), dried over anhydrous magnesium sulfate, and then the solvent was removed under reduced pressure. The obtained residue was purified by silica gel column chromatography (hexane-ethyl acetate) to give the titled compound (21.4 mg) as a colorless amorphous product. (Yield 38%)

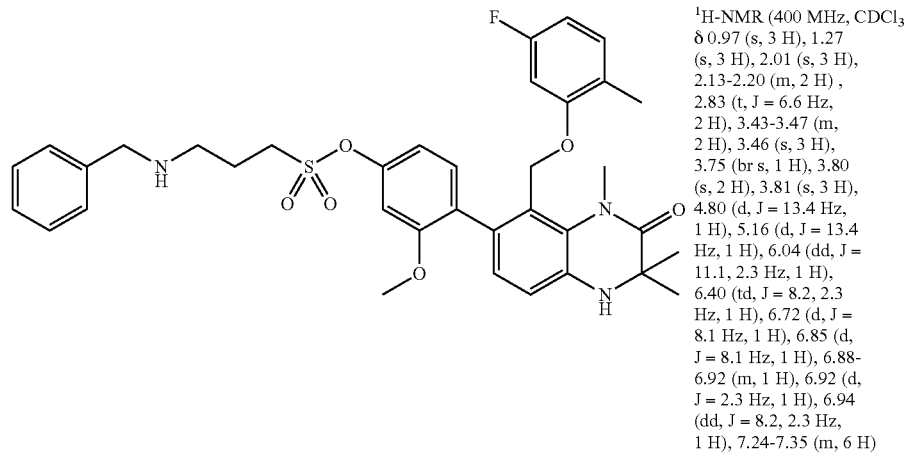

¹H-NMR (400 MHz, CDCl₃)
δ 0.97 (s, 3 H), 1.27 (s, 3 H), 2.01 (s, 3 H), 2.13-2.20 (m, 2 H), 2.83 (t, J = 6.6 Hz, 2 H), 3.43-3.47 (m, 2 H), 3.46 (s, 3 H), 3.75 (br s, 1 H), 3.80 (s, 2 H), 3.81 (s, 3 H), 4.80 (d, J = 13.4 Hz, 1 H), 5.16 (d, J = 13.4 Hz, 1 H), 6.04 (dd, J = 11.1, 2.3 Hz, 1 H), 6.40 (td, J = 8.2, 2.3 Hz, 1 H), 6.72 (d, J = 8.1 Hz, 1 H), 6.85 (d, J = 8.1 Hz, 1 H), 6.88-6.92 (m, 1 H), 6.92 (d, J = 2.3 Hz, 1 H), 6.94 (dd, J = 8.2, 2.3 Hz, 1 H), 7.24-7.35 (m, 6 H)

Using any compounds among Compound No. 1-40 and commercially available compounds, the following Compounds No. 3-2 to 3-5 were obtained by a method similar to that of Compound No. 3-1.

8-(5-Fluoro-2-methylphenoxymethyl)-7-[2-methoxy-4-(3-propylaminopropylsulfonyloxy)phenyl]-1,3,3-trimethyl-3,4-dihydro-1H-quinoxalin-2-one (Compound No. 3-2)

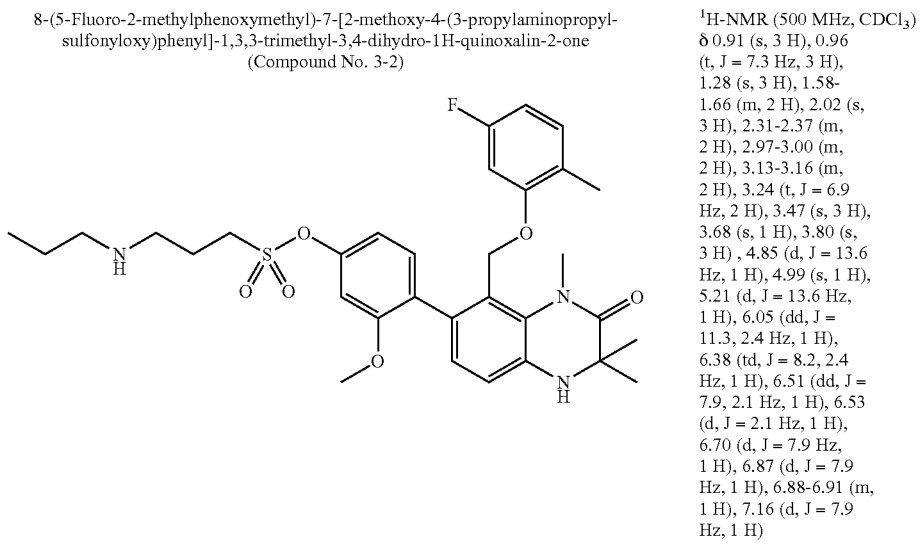

¹H-NMR (500 MHz, CDCl₃)
δ 0.91 (s, 3 H), 0.96 (t, J = 7.3 Hz, 3 H), 1.28 (s, 3 H), 1.58-1.66 (m, 2 H), 2.02 (s, 3 H), 2.31-2.37 (m, 2 H), 2.97-3.00 (m, 2 H), 3.13-3.16 (m, 2 H), 3.24 (t, J = 6.9 Hz, 2 H), 3.47 (s, 3 H), 3.68 (s, 1 H), 3.80 (s, 3 H), 4.85 (d, J = 13.6 Hz, 1 H), 4.99 (s, 1 H), 5.21 (d, J = 13.6 Hz, 1 H), 6.05 (dd, J = 11.3, 2.4 Hz, 1 H), 6.38 (td, J = 8.2, 2.4 Hz, 1 H), 6.51 (dd, J = 7.9, 2.1 Hz, 1 H), 6.53 (d, J = 2.1 Hz, 1 H), 6.70 (d, J = 7.9 Hz, 1 H), 6.87 (d, J = 7.9 Hz, 1 H), 6.88-6.91 (m, 1 H), 7.16 (d, J = 7.9 Hz, 1 H)

8-(5-Fluoro-2-methylphenoxymethyl)-7-[2-methoxy-4-[3-(morpholin-4-yl)propylsulfonyloxy]phenyl]-1,3,3-trimethyl-3,4-dihydro-1H-quinoxalin-2-one
(Compound No. 3-3)

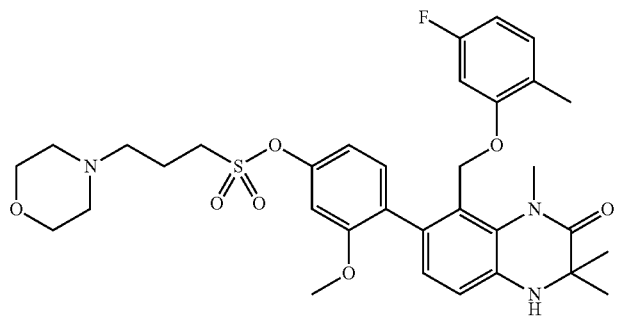 [SMILES: COc1cc(OS(=O)(=O)CCCN2CCOCC2)ccc1-c1ccc2c(c1COc1cc(F)ccc1C)N(C)C(=O)C(C)(C)N2]

$^1$H-NMR (400 MHz, CDCl$_3$) δ 0.97 (s, 3 H), 1.28 (s, 3 H), 2.01 (s, 3 H), 2.13-2.20 (m, 2 H), 2.45 (t, J = 4.6 Hz, 4 H), 2.52 (t, J = 6.7 Hz, 2 H), 3.41-3.45 (m, 2 H), 3.46 (s, 3 H), 3.70 (t, J = 4.6 Hz, 4 H), 3.75 (s, 1 H), 3.84 (s, 3 H), 4.80 (d, J = 13.5 Hz, 1 H), 5.17 (d, J = 13.5 Hz, 1 H), 6.04 (dd, J = 11.2, 2.4 Hz, 1 H), 6.40 (td, J = 8.3, 2.4 Hz, 1 H), 6.73 (d, J = 8.0 Hz, 1 H), 6.85 (d, J = 8.0 Hz, 1 H), 6.89-6.93 (m, 1 H), 6.93 (d, J = 2.3 Hz, 1 H), 6.96 (dd, J = 8.1, 2.3 Hz, 1 H), 7.33 (d, J = 8.1 Hz, 1 H)

8-(5-Fluoro-2-methylphenoxymethyl)-7-[2-methoxy-4-[3-(piperidin-1-yl)propyl-sulfonyloxyphenyl]-1,3,3-trimethyl-3,4-dihydro-1H-quinoxalin-2-one
(Compound No. 3-4)

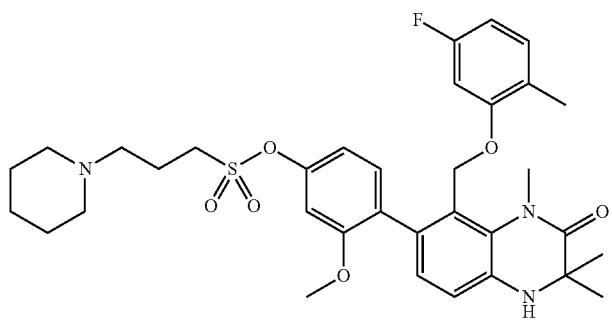 [SMILES: COc1cc(OS(=O)(=O)CCCN2CCCCC2)ccc1-c1ccc2c(c1COc1cc(F)ccc1C)N(C)C(=O)C(C)(C)N2]

$^1$H-NMR (500 MHz, CDCl$_3$) δ 0.97 (s, 3 H), 1.27 (s, 3 H), 1.40-1.45 (m, 2 H), 1.54-1.60 (m, 4 H), 2.01 (s, 3 H), 2.13-2.18 (m, 2 H), 2.37 (br s, 4 H), 2.45 (t, J = 6.7 Hz, 2 H), 3.38-3.42 (m, 2 H), 3.46 (s, 3 H), 3.74 (s, 1 H), 3.84 (s, 3 H), 4.81 (d, J = 13.4 Hz, 1 H), 5.17 (d, J = 13.4 Hz, 1 H), 6.05 (dd, J = 11.0, 2.4 Hz, 1 H), 6.40 (td, J = 8.2, 2.4 Hz, 1 H), 6.72 (d, J = 7.9 Hz, 1 H), 6.85 (d, J = 7.9 Hz, 1 H), 6.89-6.92 (m, 1 H), 6.93 (d, J = 2.1 Hz, 1 H), 6.97 (dd, J = 8.2, 2.1 Hz, 1 H), 7.32 (d, J = 8.2 Hz, 1 H)

8-(5-Fluoro-2-methylphenoxymethyl)-7-[2-methoxy-4-[3-[N-(2-methylaminoethyl)-N-methylamino]propylsulfonyloxylphenyl]-1,3,3-trimethyl-3,4-dihydro-1H-quinoxalin-2-one
(Compound No. 3-5)

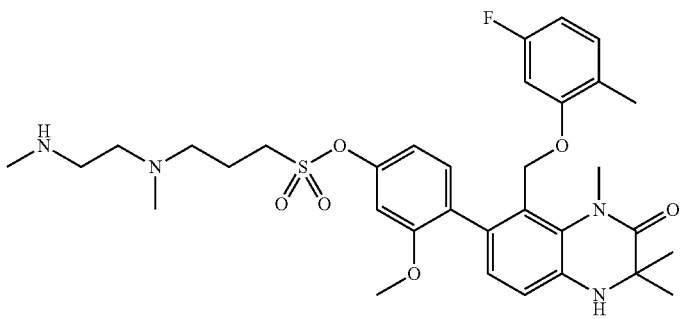

$^1$H-NMR (500 MHz, CDCl$_3$) δ 0.97 (s, 3 H), 1.27 (s, 3 H), 2.01 (s, 3 H), 2.12-2.18 (m, 2 H), 2.23 (s, 3 H), 2.44 (s, 3 H), 2.51 (t, J = 6.0 Hz, 2 H), 2.54 (t, J = 6.6 Hz, 2 H), 2.65 (t, J = 6.0 Hz, 2 H), 3.39-3.42 (m, 2 H), 3.46 (s, 3 H), 3.74 (s, 1 H), 3.84 (s, 3 H), 4.81 (d, J = 13.4 Hz, 1 H), 5.17 (d, J = 13.4 Hz, 1 H), 6.05 (dd, J = 11.3, 2.4 Hz, 1 H), 6.40 (td, J = 8.2, 2.4 Hz, 1 H), 6.72 (d, J = 8.1 Hz, 1 H), 6.86 (d, J = 8.1 Hz, 1 H), 6.89-6.92 (m, 1 H), 6.93 (d, J = 2.4 Hz, 1 H), 6.96 (dd, J = 8.2, 2.4 Hz, 1 H), 7.32 (d, J = 8.2 Hz, 1 H)

Preparation Examples

Hereinafter, typical preparation examples of the present compound are shown.

1) Tablet (in 150 mg)

| | |
|---|---:|
| Present compound | 1 mg |
| Lactose | 100 mg |
| Cornstarch | 40 mg |
| Carboxymethyl cellulose calcium | 4.5 mg |
| Hydroxypropyl cellulose | 4 mg |
| Magnesium stearate | 0.5 mg |

A tablet of the above-mentioned formulation is coated with 3 mg of a coating agent (for example, a coating agent which is used conventionally such as hydroxypropylmethyl cellulose, macrogol or a silicone resin), whereby an objective tablet can be obtained. In addition, a desired tablet can be obtained by appropriately changing the kind and/or amount of the present compound and additives.

2) Capsule (in 150 mg)

| | |
|---|---:|
| Present compound | 5 mg |
| Lactose | 135 mg |
| Carboxymethyl cellulose calcium | 4.5 mg |
| Hydroxypropyl cellulose | 4 mg |
| Magnesium stearate | 1.5 mg |

A desired capsule can be obtained by appropriately changing the kind and/or amount of the present compound and additives.

3) Eye Drop (in 100 mL)

| | |
|---|---:|
| Present compound | 100 mg |
| Sodium chloride | 900 mg |
| Polysorbate 80 | 500 mg |
| Sodium hydroxide | q.s. |
| Hydrochloric acid | q.s. |
| Sterile purified water | q.s. |

A desired eye drop can be obtained by appropriately changing the kind and/or amount of the present compound and additives.

Pharmacological Test

1. Evaluation Test for Binding Activity to GR

In order to evaluate a binding activity to GR, a receptor competitor assay was carried out by a fluorescence polarization method. In the assay, a GR competitor assay kit (manufactured by Invitrogen, cat No. P2816) was used, and a procedure was carried out according to the protocol attached to the kit. Hereinafter, the specific method will be described.

(Preparation of Reagents)

GR screening buffer: A buffer containing 10 mM potassium phosphate (pH 7.4), 20 mM sodium molybdate ($Na_2MoO_4$), 0.1 mM ethylene diamine tetraacetic acid (EDTA), 5 mM dithiothreitol (DTT), 0.1 mM stabilizing peptide and 2% dimethylsulfoxide was prepared.

4×GS1 solution: Fluormone™ GS1, which is a fluorescent glucocorticoid ligand, was diluted with GR screening buffer, whereby a 4 nM solution was prepared.

4×GR solution: Recombinant human GR was diluted with GR screening buffer, whereby a 16 nM solution was prepared.

(Preparation of Test Compound Solution)

After a test compound was dissolved in dimethylsulfoxide, the resulting solution was diluted with GR screening buffer, whereby a 20 µM test compound solution was prepared.

(Test Method and Measurement Method)

1) The test compound solution was added in an amount of 10 µL into each well of a 384-well plate, and then, 4×GS1 solution and 4×GR solution were added in an amount of 5 µL into each well, respectively.

2) The plate was incubated in a dark place at room temperature for 2 to 4 hours.

3) By using a multimode plate reader, Analyst™ HT (manufactured by LJL Biosystems), fluorescence polarization of each well was measured. As the blank, a well containing GR screening buffer in place of the test compound and 4×GS1 solution was used.

4) The same procedure as that in the above 1) to 3) was carried out except that GR screening buffer was used in place of the test compound solution, and the obtained result was taken as the negative control.

5) The same procedure as that in the above 1) to 3) was carried out except that 2 mM dexamethasone was used in place of the test compound solution, and the obtained result was taken as the positive control.

(Calculation Equation of GR Binding Ratio)

A GR binding ratio (%) was calculated from the following equation.

GR binding ratio (%)=100×[1−(fluorescence polarization of test compound solution−fluorescence polarization of positive control solution)/(fluorescence polarization of negative control solution−fluorescence polarization of positive control solution)]

(Test Results and Discussion)

The Compounds No. 1-1 to 1-44, 2-1 to 2-7, and 3-1 to 3-5 were used as test compounds, and then all of those compounds showed the GR binding rate of 80% or more.

2. Evaluation Test for GR Agonist Activity

In order to evaluate a GR agonist activity of the present compound, the inhibitory effects on the IL-6 production induced by lipopolysaccharide (LPS) in human corneal epithelial cells. IL-6 levels in the conditioned medium were measured using the HTRF human IL-6 Kit (boehringer-Ingelheim, Cat No. 62IL6PEB), and the procedure was carried out according to the protocol attached to the kit. Hereinafter, the specific method will be described.

(Preparation of Reagents)

LPS solution: After LPS was dissolved in phosphate buffer solution (hereinafter referred to as PBS(−)), the resulting solution was diluted with 10% FBS-DMEM/F12 medium, whereby a 1 µg/mL LPS solution was prepared.

(Preparation of Test Compound Solution and Dexamethasone (hereinafter referred to as DEX) Solution)

After a test compound was dissolved in dimethylsulfoxide (hereinafter referred to as DMSO), the resulting solution was diluted with 10% FBS-DMEM/F12 medium, whereby a 100 µM test compound solution was prepared. A 100 µM DEX solution was prepared by the same method, and the inhibitory ratio of IL-6 production of DEX was evaluated to use for calculating efficacy (% DEX).

(Used Cell and Method of Cell Culture)

Used cell: SV40-immortalized human corneal epithelial cells (HCE-T) (RIKEN)

Passaging Method:
1) Subconfluent HCE-T cells were rinsed with PBS(−), and treated with trypsin-EDTA solution to detach cells.
2) Trypsin was inactivated by adding SHEM medium (supplemented hormone epithelial medium. DMEM/Ham's F12 containing 15% FBS, 5 μg/mL insulin, 0.1 μg/mL choleratoxin, 10 ng/mL human EGF, 40 μg/mL gentamicin) to the flasks.
3) The above cell suspension was collected, and centrifuged at 1000 rpm for 5 minutes to obtain precipitate cells.
4) The cells were resuspended in SHEM medium and dispensed into new culture flasks, and the flasks were incubated in a $CO_2$ incubator (temperature: 37° C., $CO_2$ concentration: 5%).

(Test Method and Measurement Method)
1) HCE-T cells were harvested, and seeded at $2.0 \times 10^4$ cells/0.1 mL/well in a 96-well plate.
2) After incubation overnight, the medium was removed and a 80 μL of new 10% FBS-DMEM/Ham's F12 medium was added into each well.
3) A 10 μL of test compounds solution was added into each well.
4) A 10 μL of LPS solution was added into each well.
5) As a negative control, a 10 μL of 10% FBS-DMEM/Ham's F12 medium was added into each well instead of a test compound solution and a LPS solution.
6) As a positive control, a 10 μL of 10% FBS-DMEM/Ham's F12 medium containing 1% DMSO was added into each well instead of a test compound solution.
7) After 4 hours incubation, supernatants were collected and IL-6 levels in the supernatants were quantitated using the HTRF human IL-6 Kit.
8) The inhibition ratio of IL-6 production (%) was calculated according to the following equation.

(Calculation Equation of the Inhibition Ratio of IL-6 Production)
The inhibition ratio of IL-6 production (%) was calculated according to the following equation.

The inhibition ratio of IL-6 production (%)=100×{1−(IL-6 level in each group−mean value of IL-6 level in negative control)/(mean value of IL-6 level in positive control−mean value of IL-6 level in negative control)} (%)

Furthermore, the inhibition ratio of IL-6 production (efficacy (% DEX)) was also calculated according to the following equation.

Efficacy(% DEX)=100×{(mean value of IL-6 inhibition in compound-treated group)/(mean value of IL-6 inhibition in DEX-treated group)} (%)

(Results and Discussion)
As an example of the test results, the IL-6 production inhibitory effect (% DEX) of the test compounds (Compound No. 1-1, Compound No. 1-2, Compound No. 1-3, Compound No. 1-5, Compound No. 1-6, Compound No. 1-7, Compound No. 1-11, Compound No. 1-12, Compound No. 1-13, Compound No. 1-14, Compound No. 1-15, Compound No. 1-16, Compound No. 1-17, Compound No. 1-19, Compound No. 1-20, Compound No. 1-21, Compound No. 1-22, Compound No. 1-23, Compound No. 1-24, Compound No. 1-30, Compound No. 1-31, Compound No. 1-32, Compound No. 1-35, Compound No. 1-36, Compound No. 1-37, Compound No. 1-38, Compound No. 1-39, Compound No. 1-40, Compound No. 1-41, Compound No. 1-42, Compound No. 1-43, Compound No. 1-44, Compound No. 2-2, Compound No. 2-5, Compound No. 2-6, Compound No. 2-7, Compound No. 3-1, Compound No. 3-2, Compound No. 3-3) are shown in Table I.

TABLE I

| Test Compound | IL-6 inhibition (% DEX) |
|---|---|
| Compound No. 1-1 | 92 |
| Compound No. 1-2 | 91 |
| Compound No. 1-3 | 70 |
| Compound No. 1-5 | 88 |
| Compound No. 1-6 | 86 |
| Compound No. 1-7 | 94 |
| Compound No. 1-11 | 99 |
| Compound No. 1-12 | 100 |
| Compound No. 1-13 | 100 |
| Compound No. 1-14 | 86 |
| Compound No. 1-15 | 88 |
| Compound No. 1-16 | 91 |
| Compound No. 1-17 | 83 |
| Compound No. 1-19 | 88 |
| Compound No. 1-20 | 74 |
| Compound No. 1-21 | 71 |
| Compound No. 1-22 | 99 |
| Compound No. 1-23 | 83 |
| Compound No. 1-24 | 85 |
| Compound No. 1-30 | 74 |
| Compound No. 1-31 | 76 |
| Compound No. 1-32 | 90 |
| Compound No. 1-35 | 79 |
| Compound No. 1-36 | 72 |
| Compound No. 1-37 | 74 |
| Compound No. 1-38 | 94 |
| Compound No. 1-39 | 80 |
| Compound No. 1-40 | 84 |
| Compound No. 1-41 | 85 |
| Compound No. 1-42 | 81 |
| Compound No. 1-43 | 82 |
| Compound No. 1-44 | 88 |
| Compound No. 2-2 | 86 |
| Compound No. 2-5 | 74 |
| Compound No. 2-6 | 82 |
| Compound No. 2-7 | 94 |
| Compound No. 3-1 | 78 |
| Compound No. 3-2 | 70 |
| Compound No. 3-3 | 85 |

As shown in Table I, the present compound showed an excellent IL-6 production inhibitory effect. Therefore, along with the result of the above-mentioned 1 (Binding Activity to GR), the present compound is useful as a GR agonist, and a therapeutic agent for the diseases to which GR agonists such as steroids are effective, especially the inflammatory diseases (bone-joint disorders, ocular inflammatory diseases and the like).

3. Inhibitory Effect on the Vascular Hyper-Permeability in Allergic Conjunctivitis Model In order to evaluate anti-allergic effect of the present compound, the inhibitory effect on the vascular hyper-permeability in allergic conjunctivitis model in mice was examined. This effect was calculated based on dye leakages of vehicle-treated group (control group) and test compound-treated group.

(Preparation of Test Compound Suspension)
By adding 0.5% polysorbate 80/saline to the test compound, a 1% (W/V) test compound suspension was prepared.

(Procedure of Allergic Conjunctivitis Model and Evaluating Method)
1) Ovalbumin absorbed on aluminum hydroxide gel was dissolved in saline (20 μg ovalbumin/mL), and male BALB/c mice, 6 weeks old, were actively sensitized to the antigen by intraperitoneal injections of 500 μL of it.
2) On the 6th day from sensitization, sensitized mice were boosted by additional intraperitoneal injections of 500 μL ovalbumin absorbed on aluminum hydroxide gel (20 μg ovalbumin/mL).

3) On the 11th day, 12th day, 13th day, 14th day and 15th day from the first sensitization, allergic conjunctivitis were induced by instillations to the right eyes of the mice of 2 μg of 50% glycerol solution containing 15% (W/V) ovalbumin.

4) 2 μg of test compound suspension per eye was instilled to the right eye of the above mice 15 min, 1 hr and 3 hrs before ovalbumin instillation (three times) on the 15th day from sensitization. In vehicle-treated group (control group), the mice were instilled with 0.5% polysorbate 80/saline in substitution for test compound suspension.

5) Just before ovalbumin instillation on the 15th day from sensitization, all animals received a tail intravenous injection of 0.1% Evans blue dye. The right periocular tissues of the mice, which were the leaked parts of dye, were collected 30 min after ovalbumin instillation. The dye was extracted from the tissues with the dye extraction liquid. Then the absorbance of the dye extract was measured. The dye leakage was calculated from the absorbance value, and the inhibition ratio of the vascular hyper-permeability of test compound-treated group was calculated according to calculation equation 1.

The inhibition ratio of the vascular hyper-permeability of test compound-treated group (%)=(1−$Ax/Ao$)×100　　(Calculation Equation 1)

Ao: Dye leakage in vehicle-treated group (control group)
Ax: Dye leakage in test compound-treated group (Test Results and Discussion)

As an example of the test results, the inhibition ratio of the vascular hyper-permeability of test compounds (Compound No. 1-1, Compound No. 1-2, Compound No. 1-5, Compound No. 1-11, Compound No. 1-12, Compound No. 1-16, Compound No. 1-22, Compound No. 1-23, Compound No. 1-44, Compound No. 2-6, Compound No. 2-7) are shown in table II.

TABLE II

| Test Compound | The inhibition ratio of the vascular hyper-permeability (%) |
|---|---|
| Compound No. 1-1 | 36 |
| Compound No. 1-2 | 37 |
| Compound No. 1-5 | 30 |
| Compound No. 1-11 | 20 |
| Compound No. 1-12 | 15 |
| Compound No. 1-16 | 18 |
| Compound No. 1-22 | 21 |
| Compound No. 1-23 | 10 |
| Compound No. 1-44 | 22 |
| Compound No. 2-6 | 13 |
| Compound No. 2-7 | 35 |

(The values were the mean value of 6 eyes, 6 animals.)

As shown in Table II, the present compound has inhibitory effect on the vascular hyper-permeability. Therefore, the present compound is useful as a therapeutic agent for anterior ocular inflammatory diseases, especially allergic ocular diseases such as allergic conjunctivitis.

4. Evaluation Test for Inhibitory Effect on Choroidal Neovascularization

The choroidal neovascularization (CNV) model in rats is known as one of the popular methods for evaluating the CNV inhibitory effect of drugs. This method is reported in Graefe's Arch. Cli. Exp. Ophthalmol., 235, 313-319 (1997). According to this method, the CNV examinations were performed to evaluate the CNV inhibitory effect of test compounds by comparing the incidence rates of CNV in vehicle group (control group) with test compound-treated groups.

(Preparation of Test Compound Suspension)

For eye drop administration, a 1% (w/v) test compound suspension was prepared by adding 0.5% polysorbate 80/saline to the test compound. For subconjunctival injection, a 20 mg/mL test compound suspension was prepared by adding 0.5% hydrogenated castor oil/saline to the test compound.

(Procedure of Laser Induced Choroidal Neovascularization Model in Rats)

1) Brown Norway male rats (7-8 weeks) were anesthetized with intramuscular injection (1 mL/kg) of the mixed solution (5% ketamine HCl:2% xylazine HCl=7:1).

2) After mydriasis using tropicamide phenylephrine hydrochloride eye drops (trade name Mydrin P), laser photocoagulation of bruch's membrane in rats was performed with krypton laser photocoagulation machine. Laser irradiation was performed at 8 points per eye avoiding thick retinal blood vessels in ocular fundus and focusing on the depth of retina. The conditions were 100 μm spot size, 100 mW power, 0.1 second duration.

3) After laser photocoagulation, photographs of ocular fundus were taken and the laser photocoagulation (laser irradiation) points were confirmed.

(Test Method and Measurement Method)

1) In case of eye drops administration, a test compound suspension was administrated four times a day from laser irradiation day (the 1st day) to the 8th day. In case of subconjunctival injection, a 50 μL test compound suspension was injected into conjunctivae just after laser irradiation.

2) In vehicle group (control group), 0.5% polysorbate 80/saline or 0.5% hydrogenated castor oil/saline was used instead of a test compound suspension. And the test was performed according to the method 1). These results were adopted as a control.

(Evaluation Method)

1) 7 days after laser irradiation, 0.1 mL of 10% fluorescein was injected into rat tail vein and fluorescein angiography was performed.

2) When the fluorescent leakage was not detected in the fluorescent angiography, the spot was judged to be a negative spot. When the fluorescent leakage was detected, the spot was judged to be a positive spot. When the fluorescent leakage was detected as a little leakage, two spots were counted as one positive spot.

3) The neovascular incidence rate was calculated according to the equation 1. According to the equation 2, the ratio of neovascular incidence rate in test compound group to vehicle group was calculated.

Neovascular incidence rate (%)=(Positive spots/all spots)×100　　(Equation 1)

Angiogenic inhibition ratio in test compound group (%)=(1−$Ax/Ao$)×100　　(Equation 2)

Ao: Neovascular incidence rate in vehicle group (control group)
Ax: Neovascular incidence rate in test compound group (Test Result and Discussion)

As an example of the test results, angiogenic inhibition ratios (%) of the test compounds (compound 1-1, compound 1-13, compound 1-38, compound 1-43, compound 2-2) are shown in Table III.

TABLE III

| Test Compound | Angiogenic inhibition ratio (%) |
|---|---|
| Compound 1-1 | 31 |
| Compound 1-13 | 38 |

TABLE III-continued

| Test Compound | Angiogenic inhibition ratio (%) |
|---|---|
| Compound 1-38 | 33 |
| Compound 1-43 | 18 |
| Compound 2-2 | 41 |

(Each value was the mean value of 7-8 eyes in 4 rats)

As shown in Table III, the present compound inhibits the neovascularization compared with vehicle and has the inhibitory effect of choroidal neovascularization. Therefore, the present compound is useful as a therapeutic agent for posterior eye inflammatory disease, especially age-related macular degeneration, diabetic retinopathy and diabetic macular edema and the like.

5. Evaluation Test for Inhibitory Effect on Inflammation on Joint and the Like.

The inhibitory effect for paw edema using carrageenan-induced paw edema model in rats is known as one of the general methods for testing the inhibitory effect on inflammation on the joint and the like. Therefore, the inhibitory effect of the present compound for paw edema was carried out, the inhibition rate of paw edema was calculated, and then the anti-inflammatory effect of the present compound was evaluated based on the rate. The concrete method of the test is described below.

(Preparation of Test Compound Suspension)

A 2 mg/mL test compound suspension was prepared by adding 1% methyl cellulose (base) to the test compound.

(Procedure)

1) The weight and right hind paw volume of female Lewis rat (8~10 weeks) were measured before drug administration.

2) The test compound suspension was administered at 10 mg/kg to the test compound group. Meanwhile, 1% methyl cellulose was administered orally at 5 mL/kg to the sham-operation group and vehicle group (control group).

3) After 30 minutes from oral administration, 0.1 mL of a 1% w/v carrageenan/distilled water solution was subcutaneously injected into right foot pad. 0.1 mL of distilled water was subcutaneously injected for sham-operation group.

4) The right hind paw volume was measured 3 hr after injection of carrageenan or distilled water.

(Formulation Concerning Estimation of Drug Activity)

The increase ratio of paw volume (%)=100×(right hind paw volume 3 hr after injection of carrageenan or distilled water (mL)−right hind paw volume before the test compound administration (mL))/right hind paw volume before the test compound administration (mL)     (Calculation Equation 1)

The inhibition ratio of paw edema (%)=100−100×(the increase ratio of paw volume of each test compound group (%)−the increase ratio of paw volume of sham-operation group (%))/(the increase of paw volume of vehicle group (%)−the increase of paw volume of sham-operation group (%))     (Calculation Equation 2)

(Test Results and Discussion)

As an example of the test results, the inhibitory ratios (%) of the test compounds (Compound No. 1-6, Compound No. 1-7, Compound No. 1-13, Compound No. 1-32, Compound No. 1-38, Compound No. 1-42, Compound No. 2-2, Compound No. 2-5 and Compound No. 2-7) on carrageenan-induced paw edema are shown in table IV

TABLE IV

| Test Compound | Inhibition ratio of paw edema (%) |
|---|---|
| Compound No. 1-6 | 63 |
| Compound No. 1-7 | 43 |
| Compound N0. 1-13 | 67 |
| Compound No. 1-32 | 61 |
| Compound No. 1-38 | 50 |
| Compound No. 1-42 | 52 |
| Compound No. 2-2 | 51 |
| Compound No. 2-5 | 40 |
| Compound No. 2-7 | 52 |

As shown in table IV, the present compound showed an excellent inhibitory effect on paw edema. Therefore, the present compound is useful as a therapeutic agent for inflammatory bone-joint disorders such as rheumatoid arthritis.

INDUSTRIAL APPLICABILITY

The glucocorticoid receptor agonists in this invention are useful as therapeutic agents for the ocular inflammatory diseases and/or the inflammatory bone-joint disorders, and useful as therapeutic agents for the inflammatory diseases on anterior ocular segment such as keratitis, keratoconjunctivitis, conjunctivitis, blepharitis, dry eye syndrome (dry eye), allergic conjunctivitis, anterior uvetis, inflammation on anterior ocular segment after operation and inflammation by rejection of eye organization transplant; therapeutic agents for the inflammatory diseases on posterior ocular segment such as age-related macular degeneration, diabetic retinopathy, diabetic macular edema, neovascular maculopathy, spasmodic epimacular membarane, proliferative vitreoretinopathy, pigmentary degeneration of the retina, central vein of retina obstruction, central artery of retina obstruction, branch retinal vein occlusion, branch retinal artery occlusion, inflammation or degeneration caused by retinal detachment or injury (including surgical operation), retinitis, uvetis, scleritis, optic neuritis, and/or therapeutic agents for the inflammatory bone-joint disorders such as rheumatoid arthritis, juvenile rheumatoid arthritis (includes still's disease), osteoarthritis, osteoporosis, spondylarthritis.

The invention claimed is:

1. A method for treating an ocular inflammatory disease comprising administering to a patient in need thereof a therapeutically effective amount of a compound represented by the following formula (1) or a salt thereof:

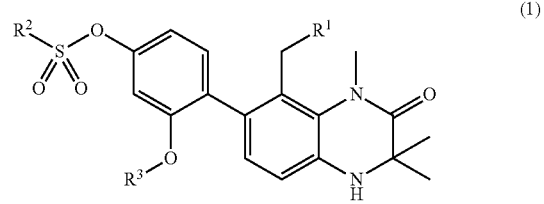

(1)

$R^1$ represents the following formula (2a), (3a), (4a) or (5a);

(2a)

-continued

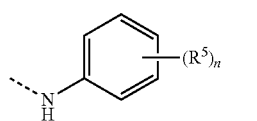   (3a)

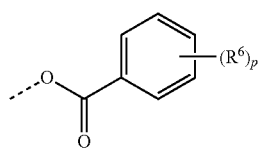   (4a)

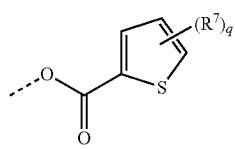   (5a)

R² represents a lower alkyl group which may have a substituent, a lower cycloalkyl group which may have a substituent or an aralkyl group which may have a substituent;
R³ represents a lower alkyl group;
R⁴, R⁵, R⁶ or R⁷ represents a halogen atom, a lower alkyl group which may have a substituent, a hydroxyl group, a lower alkoxy group which may have a substituent, a cyano group or a nitro group;
m, n, p or q represents 0, 1 or 2;
in the case where m, n, p or q is 2, each R⁴, R⁵, R⁶ or R⁷ may be the same or different.

2. The method according to claim 1, wherein in the formula (1),
R¹ represents the following formula (2a), (3a), (4a) or (5a);

(2a)

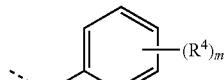

(3a)

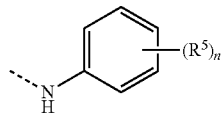

(4a)

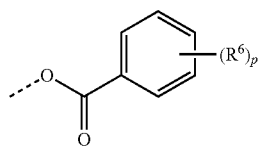

(5a)

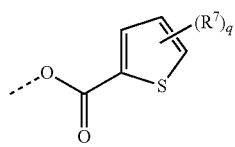

R² represents a lower alkyl group which may have a substituent, a lower cycloalkyl group which may have a substituent or an aralkyl group which may have a substituent;
R³ represents a lower alkyl group;
R⁴ represents a halogen atom, a lower alkyl group, a lower alkoxy or a nitro group;

R⁵ represents a halogen atom, a lower alkyl group, or a lower alkoxy group;
R⁶ represents a lower alkyl group or a lower alkoxy group;
R⁷ represents a halogen atom or a lower alkyl group;
m, n or p represents 1 or 2;
in the case where m, n or p is 2, each R⁴, R⁵ or R⁶ may be the same or different;
q represents 0 or 1.

3. The method according to claim 1, wherein in the formula (1),
R¹ represents the following formula (2b-1), (2b-2), (2b-3), (3b-1), (3b-2), (4b-1) or (5b-1);

(2b-1)

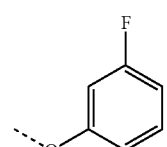

(2b-2)

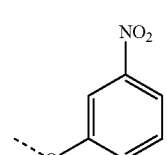

(2b-3)

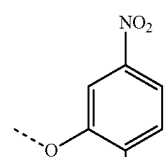

(3b-1)

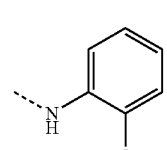

(3b-2)

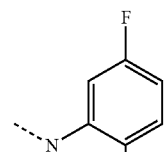

(4b-1)

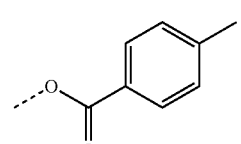

(5b-1)

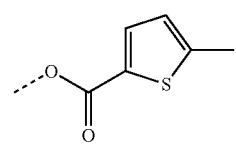

R² represents a lower alkyl group which may have a substituent, a lower cycloalkyl group which may have a substituent or an aralkyl group which may have a substituent;

R³ represents a methyl group.

4. A method for treating an ocular inflammatory disease comprising administering to a patient in need thereof a therapeutically effective amount of a compound selected from the group consisting of 8-(5-Fluoro-2-methylphenoxymethyl)-7-(2-methoxy-4-methylsulfonyloxyphenyl)-1,3,3-trimethyl-3,4-dihydro-1H-quinoxalin-2-one, 8-(5-Fluoro-2-methylphenoxymethyl)-7-(2-methoxy-4-propylsulfonyloxyphenyl)-1,3,3-trimethyl-3,4-dihydro-1H-quinoxalin-2-one, 7-(2-Methoxy-4-methylsulfonyloxyphenyl)-8-(5-methylthiophen-2-ylcarbonyloxymethyl)-1,3,3-trimethyl-3,4-dihydro-1H-quinoxalin-2-one, 7-(4-Benzylsulfonyloxy-2-methoxyphenyl)-8-(5-fluoro-2-methylphenoxymethyl)-1,3,3-trimethyl-3,4-dihydro-1H-quinoxalin-2-one, 7-(4-Butylsulfonyloxy-2-methoxyphenyl)-8-(5-fluoro-2-methylphenoxymethyl)-1,3,3-trimethyl-3,4-dihydro-1H-guinoxalin-2-one, 7-(4-Ethylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-(4-isopropylsulfonyloxy-2- methoxyphenyl)-1,3,3-trimethyl-3,4-dihydro-1H-quinoxalin-2-one, 7-[4-(3-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(4-methylbenzylsulfonyloxy)phenyl]-1,3,3-trimethyl-3,4-dihydro-1H-quinoxalin-2-one, 7-[4-(4-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5, -Fluoro-2-methylphenoxymethyl)-7-(4-isobutylsulfonyloxy2-methoxyphenyl)-1,3,3-trimethyl-3,4-dihydro-1H-quinoxalin-2-one, 8-(5-Fluoro-2-methylphenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-fluoro-2-methylphenoxymethyl)-1,3,3-trimethyl-3,4-dihydro-1H-quinoxalin-2-one, 7-[4-(2-Chlorobenzylsulfonyloxy)-2-methoxyphenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(2-methylbenzylsulfonyloxy)phenyl]-1,3,3-trimethyl-3,4-dihydro-1H-quinoxalin-2-one, 7-(4-Cyclopentylsulfonyloxy-2-methoxyphenyl)-8-(5-fluoro-2-methylphenoxymethyl)-1,3,3-trimethyl-3,4-dihydro-1H-quinoxalin-2-one, 7-(4-Cyclohexylsulfonyloxy-2-methoxyphenyl)-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(3-methylbenzylsulfonyloxy)phenyl]-1,3,3-trimethyl-3,4-dihydro-1H-quinoxalin-2-one, 7-(4-Cyclopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-[2-Methoxy-4-(3,3,3-trifluoropropylsulfonyloxy)phenyl]-8-(5-methylthiophen-2-ylcarbonyloxymethyl)-1,3,3-trimethyl-3,4-dihydro-1H-quinoxalin-2-one, 7-(4-Isobutylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-propylsulfonyloxyphenyl)-8-(5-methylthiophen-2-ylcarbonyloxymethyl)-1,3,3-trimethyl-3,4-dihydro-1H-quinoxalin-2-one, 7-(4-Isopropylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(4-Cyclopentylsulfonyloxy-2-methoxyphenyl)-8-(5-methylthiophen-2-ylcarbonyloxymethyl)-1,3,3-trimethyl-3,4-dihydro-1H-quinoxalin-2-one, 7-(2-Methoxy-4-methylsulfonyloxyphenyl)-8-(2-methoxy-5-nitrophenoxymethyl)-1,3,3-trimethyl-3,4-dihydro-1H-quinoxalin-2-one, 8-(2-Methoxy-5-nitrophenoxymethyl)-7-[2-methoxy-4-(3,3,3-trifluoropropylsulfonyloxy)phenyl]-1,3,3-trimethyl-3,4-dihydro-1H-quinoxalin-2-one, 7-(4-Isobutylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopentylsulfonyloxy-2-methoxyphenyl)-8-(2-methoxy-5-nitrophenoxymethyl)-1,3,3-trimethyl-3,4-dihydro-1H-quinoxalin-2-one, 7-(4-Isopropylsulfonyloxy-2-methoxyphenyl)-8-(2-methoxy-5-nitrophenoxymethyl)-1,3,3-trimethyl-3,4-dihydro-1H-quinoxalin-2-one, 7-(4-Cyclopropylsulfonyloxy-2-methoxyphenyl)-8-(2-methoxy-5-nitrophenoxymethyl)-1,3,3-trimethyl-3,4-dihydro-1H-quinoxalin-2-one, 8-(2-Methoxy-5-nitrophenoxymethyl)-7-(2-methoxy-4-propylsulfonyloxyphenyl)-1,3,3-trimethyl-3,4-dihydro-1H-quinoxalin-2-one, 7-(4-Cyclopropylsulfonyloxy-2-methoxyphenyl)-8-(2-methyl-5-nitrophenoxymethyl)-1,3,3-trimethyl-3,4-dihydro-1H-quinoxalin-2-one, 7-[2-Methoxy-4-(3,3,3-trifluoropropylsulfonyloxy)phenyl]-8-(2-methyl-5-nitrophenoxymethyl)-1,3,3-trimethyl-3,4-dihydro-1H-quinoxalin-2-one, 7-(4-Isobutylsulfonyloxy-2-methoxyphenyl)-8-(2-methyl-5-nitrophenoxymethyl)-1,3,3-trimethyl-3,4-dihydro-1H-quinoxalin-2-one, 7-(4-Isopropylsulfonyloxy-2-methoxyphenyl)-8-(2-methyl-5-nitrophenoxymethyl)-1,3,3-trimethyl-3,4-dihydro-1H-quinoxalin-2-one, 7-(2-Methoxy-4-methylsulfonyloxyphenyl)-8-(2-methyl-5-nitrophenoxymethyl)-1,3,3-trimethyl-3,4-dihydro-1H-quinoxalin-2-one, 7-(4-Cyclopentylsulfonyloxy-2-methoxyphenyl)-8-(2-methyl-5-nitrophenoxymethyl)-1,3,3-trimethyl-3,4-dihydro-1H-quinoxalin-2-one, 7-(2-Methoxy-4-propylsulfonyloxyphenyl)-8-(2-methyl-5-nitrophenoxymethyl)-1,3,3-trimethyl-3,4-dihydro-1H-quinoxalin-2-one, 7-(2-Methoxy-4-propylsulfonyloxyphenyl)-8-(4-methyl-benzoyloxymethyl)-1,3,3-trimethyl-3,4-dihydro-1H-quinoxalin-2-one, 7-[4-(3-Chloropropylsulfonyloxy)-2-methoxyphenyl]-8-(5-fluoro-2-methylphenoxymethyl)-1,3,3-trimethyl-3,4-dihydro-1H-quinoxalin-2-one, 7-(4-Chloromethylsulfonyloxy-2-methoxyphenyl)-8-(5-fluoro-2-methylphenoxymethyl)-1,3,3-trimethyl-3,4-dihydro-1H-quinoxalin-2-one, 7-(4-Cyclopropylsulfonyloxy-2-methoxyphenyl)-8-(5-fluoro-2-methylphenylaminomethyl)-1,3 3-trimethyl-3,4-dihydro-1H-quinoxalin-2-one, 7-(4-Cyclopentylsulfonyloxy-2-methoxyphenyl)-8-(5-fluoro-2-methylphenylaminomethyl)-1,3,3-trimethyl-3,4-dihydro-1H-quinoxalin-2-one, 8-(5-Fluoro-2-methylphenylaminomethyl)-7-(2-methoxy-4-propylsulfonyloxyphenyl)-1,3,3-trimethyl-3,4-dihydro-1H-quinoxalin-2-one, 7-(2-Methoxy-4-methylsulfonyloxyphenyl)-8-(2-methoxyphenylaminomethyl)-1,3,3-trimethyl-3,4-dihydro-1H-quinoxalin-2-one, 7-(4-Cyclopropylsulfonyloxy-2-methoxyphenyl)-8-(2-methoxyphenylaminomethyl)-1,3,3-trimethyl-3,4-dihydro-1H-quinoxalin-2-one, 8-(2-Methoxyphenylaminomethyl)-7-[2-methoxy-4-(3,3,3-trifluoropropylsulfonyloxy)phenyl]-1,3,3-trimethyl-3,4-dihydro-1H-quinoxalin-2-one, 7-(4-Isobutylsulfonyloxy-2-methoxyphenyl)-8-(2-methoxyphenylaminomethyl)-1,3,3-trimethyl-3,4-dihydro-1H-quinoxalin-2-one, 7-(4-Isopropylsulfonyloxy-2-methoxyphenyl)-8-(2-methoxyphenylaminomethyl)-1,3,3-trimethyl-3,4-dihydro-1H-quinoxalin-2-one, 7-(4-Cyclopentylsulfonyloxy-2-methoxyphenyl)-8-(2-methoxyphenylaminomethyl)-1,3,3-trimethyl-3,4-dihydro-1H-quinoxalin-2-one, 8-(2-Methoxyphenylaminomethyl)-7-(2-methoxy-4-propylsulfonyloxyphenyl)-1,3,3-trimethyl-3,4-dihydro-1H-quinoxalin-2-one, 7-[4-(3-Benzylaminopropylsulfonyloxy)-2-methoxy-phenyl]-8-(5-fluoro-2-methylphenoxymethyl)-1,3,3-trimethyl-3,4-dihydro-1H-quinoxalin-2-one, 8-(5-Fluoro-2-methylphenoxymethyl)-7-[2-methoxy-4-(3-propylaminopropylsulfonyloxy)phenyl]-1,3,3-trimethyl-3,4-dihydro-1H-quinoxalin-2-one, 8-(5-Fluoro-2-methylphenoxymethyl)-7-[2-methoxy-4-[3-(morpholin-4-yl)propylsulfonyloxy]phenyl]-1,3,3-trimethyl-3,4-dihydro-1H-quinoxalin-2-one, 8-(5-Fluoro-2-methylphenoxymethyl)-7-[2-methoxy-4-[3-(piperidin-1-yl)propylsulfonyloxyphenyl]-1,3,3-trimethyl-3,4-dihydro-1H-quinoxalin-2-one, and 8-(5-Fluoro-2-methylphenoxymethyl)-7-[2-methoxy-4-[3-[N-(2-methylaminoethyl)-N-methylamino]propylsulfonyloxy]phenyl]-1,3,3-trimethyl-3,4-dihydro-1H-quinoxalin-2-one, or a salt thereof.

5. The method according to claim 1, wherein the ocular inflammatory disease is an inflammatory disease of the anterior segment of an eyeball.

6. The method according to claim 1, wherein the ocular inflammatory disease is dry eye syndrome or allergic conjunctivitis.

7. The method according to claim 1, wherein the ocular inflammatory disease is an inflammatory disease of the posterior segment of an eyeball.

8. The method according to claim 1, wherein the ocular inflammatory disease is age-related macular degeneration, diabetic retinopathy or diabetic macular edema.

* * * * *